(12) United States Patent
Bar et al.

(10) Patent No.: US 11,051,959 B2
(45) Date of Patent: *Jul. 6, 2021

(54) INTRAVASCULAR ANEURYSM TREATMENT DEVICE AND METHODS

(71) Applicant: INSPIREMD, LTD., Tel Aviv (IL)

(72) Inventors: Eli Bar, Moshav Megadim (IL); Asher Holzer, Raanana (IL); Ofir Paz, Rishon Lezion (IL)

(73) Assignee: INSPIREMD, LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,339

(22) Filed: Nov. 6, 2015

(65) Prior Publication Data

US 2016/0058589 A1    Mar. 3, 2016

Related U.S. Application Data

(63) Continuation of application No. 12/791,008, filed on Jun. 1, 2010, now Pat. No. 10,070,976, which is a
(Continued)

(51) Int. Cl.
*A61F 2/07* (2013.01)
*A61F 2/90* (2013.01)
(Continued)

(52) U.S. Cl.
CPC .............. *A61F 2/90* (2013.01); *A61F 2/0063* (2013.01); *A61F 2/07* (2013.01); *A61F 2/82* (2013.01);
(Continued)

(58) Field of Classification Search
CPC .................. A61F 2/07; A61F 2002/823; A61F 2002/077; A61F 2002/075; A61F 2/90;
(Continued)

(56) References Cited

U.S. PATENT DOCUMENTS 4,164,045 A    8/1979    Bokros et al.
4,300,244 A    11/1981   Bokros
(Continued)

FOREIGN PATENT DOCUMENTS

CN    1414840 A    4/2003
EP    0839506 A1   5/1998
(Continued)

OTHER PUBLICATIONS

European Patent Application No. 07827227.5, Search report from European Patent Office dated Feb. 25, 2013.
(Continued)

*Primary Examiner* — Brian E Pellegrino
(74) *Attorney, Agent, or Firm* — Kligler & Associates Patent Attorneys Ltd

(57) ABSTRACT

An intravascular device configured to treat an aneurysm that includes a support structure including metal struts configured to be positioned in a body lumen and defining a central fluid passage that extends axially along the support structure, and a knitted mesh cover disposed over an exterior thereof and across a radial arc and along a length of the support structure sufficient to exceed an opening of an aneurysm to be treated, and the cover includes a polymer fiber having a diameter of at least 40 nanometers to 30 microns and apertures therethrough, the apertures being sized to prevent blood from passing through the device to prevent further expansion of the aneurysm. Devices including apertures that are at least 20 microns and sized to minimize or prevent an aneurysm-filling material from exiting the aneurysm through the knitted mesh cover and support structure, and methods of stenting, are also encompassed.

22 Claims, 29 Drawing Sheets

Related U.S. Application Data continuation of application No. 12/513,851, filed as application No. PCT/IL2007/001442 on Nov. 21, 2007, now abandoned.

(60) Provisional application No. 60/860,486, filed on Nov. 22, 2006.

(51) Int. Cl.

| | |
|---|---|
| *A61L 31/14* | (2006.01) |
| *A61L 31/16* | (2006.01) |
| *A61F 2/82* | (2013.01) |
| *C08G 63/00* | (2006.01) |
| *C08G 63/06* | (2006.01) |
| *C08G 63/08* | (2006.01) |
| *C08G 63/40* | (2006.01) |
| *C08G 73/02* | (2006.01) |
| *C08G 79/04* | (2006.01) |
| *A61F 2/00* | (2006.01) |
| *A61L 31/02* | (2006.01) |
| *A61L 31/04* | (2006.01) |
| *A61L 31/06* | (2006.01) |
| *A61L 31/10* | (2006.01) |
| *A61F 2/89* | (2013.01) |

(52) U.S. Cl.
CPC .......... *A61L 31/022* (2013.01); *A61L 31/048* (2013.01); *A61L 31/06* (2013.01); *A61L 31/10* (2013.01); *A61L 31/146* (2013.01); *A61L 31/148* (2013.01); *A61L 31/16* (2013.01); *C08G 63/00* (2013.01); *C08G 63/06* (2013.01); *C08G 63/08* (2013.01); *C08G 63/40* (2013.01); *C08G 73/02* (2013.01); *C08G 79/04* (2013.01); *A61F 2/89* (2013.01); *A61F 2002/0086* (2013.01); *A61F 2002/075* (2013.01); *A61F 2002/823* (2013.01); *A61F 2210/0004* (2013.01); *A61F 2210/0076* (2013.01); *A61F 2240/001* (2013.01); *A61F 2250/0023* (2013.01); *A61F 2250/0067* (2013.01); *A61L 2300/604* (2013.01); *A61L 2300/606* (2013.01); *A61L 2420/02* (2013.01); *Y10T 29/49964* (2015.01)

(58) Field of Classification Search
CPC ....... A61F 2250/0023; A61B 17/12118; A61B 17/12113
USPC ...................................................... 606/200
See application file for complete search history.

(56) References Cited

U.S. PATENT DOCUMENTS

| | | |
|---|---|---|
| 4,321,711 A | 3/1982 | Mano |
| 4,425,908 A | 1/1984 | Simon |
| 4,723,549 A | 2/1988 | Wholey et al. |
| 4,832,688 A | 5/1989 | Sagae et al. |
| 4,865,017 A | 9/1989 | Shinozuka |
| 4,873,978 A | 10/1989 | Ginsburg |
| 4,969,891 A | 11/1990 | Gewertz |
| 4,990,156 A | 2/1991 | Lefebvre |
| 4,998,539 A | 3/1991 | Delsanti |
| 5,019,090 A | 5/1991 | Pinchuk |
| 5,122,154 A | 6/1992 | Rhodes |
| 5,152,777 A | 10/1992 | Goldberg et al. |
| 5,171,233 A | 12/1992 | Amplatz et al. |
| 5,192,286 A | 3/1993 | Phan et al. |
| 5,236,447 A | 8/1993 | Kubo et al. |
| 5,330,482 A | 7/1994 | Gibbs et al. |
| 5,366,504 A | 11/1994 | Anderson et al. |
| 5,382,261 A | 1/1995 | Palmaz |
| 5,383,887 A | 1/1995 | Nadal |
| 5,403,341 A | 4/1995 | Solar |
| 5,421,955 A | 6/1995 | Lau et al. |
| 5,443,499 A | 8/1995 | Schmitt |
| 5,470,313 A | 11/1995 | Crocker et al. |
| 5,486,183 A | 1/1996 | Middleman et al. |
| 5,569,295 A | 10/1996 | Lam |
| 5,591,228 A | 1/1997 | Edoga |
| 5,713,948 A | 2/1998 | Uflacker |
| 5,769,884 A | 6/1998 | Solovay |
| 5,788,979 A | 8/1998 | Alt et al. |
| 5,824,037 A | 10/1998 | Fogarty et al. |
| 5,827,324 A | 10/1998 | Cassell et al. |
| 5,833,651 A | 11/1998 | Donovan et al. |
| 5,843,116 A | 12/1998 | Crocker et al. |
| 5,843,161 A | 12/1998 | Solovay |
| 5,851,231 A | 12/1998 | Wolff |
| 5,871,536 A * | 2/1999 | Lazarus ............... A61F 2/07 623/1.13 |
| 5,871,538 A | 2/1999 | Dereume |
| 5,908,448 A | 6/1999 | Roberts et al. |
| 5,919,225 A | 7/1999 | Lau et al. |
| 5,941,896 A | 8/1999 | Kerr |
| 5,951,599 A | 9/1999 | McCrory |
| 5,984,955 A | 11/1999 | Wisselink |
| 6,007,543 A | 12/1999 | Ellis et al. |
| 6,015,430 A | 1/2000 | Wall |
| 6,015,432 A | 1/2000 | Rakos et al. |
| 6,027,517 A | 2/2000 | Crocker et al. |
| 6,030,414 A | 2/2000 | Taheri |
| 6,042,597 A | 3/2000 | Kveen et al. |
| 6,066,167 A | 5/2000 | Lau et al. |
| 6,077,273 A | 6/2000 | Euteneuer et al. |
| 6,096,027 A | 8/2000 | Layne |
| 6,152,144 A | 11/2000 | Lesh et al. |
| 6,176,875 B1 | 1/2001 | Lenker et al. |
| 6,245,089 B1 | 6/2001 | Daniel et al. |
| 6,254,627 B1 | 7/2001 | Freidberg |
| 6,261,320 B1 | 7/2001 | Tam et al. |
| 6,263,880 B1 | 7/2001 | Parker et al. |
| 6,306,162 B1 | 10/2001 | Patel |
| 6,340,364 B2 | 1/2002 | Kanesaka |
| 6,348,065 B1 | 2/2002 | Brown et al. |
| 6,357,104 B1 | 3/2002 | Myers |
| 6,361,558 B1 | 3/2002 | Hieshima et al. |
| 6,369,039 B1 | 4/2002 | Palasis et al. |
| 6,371,962 B1 | 4/2002 | Ellis et al. |
| 6,383,171 B1 | 5/2002 | Gifford et al. |
| 6,432,129 B2 | 8/2002 | Dicaprio |
| 6,436,132 B1 | 8/2002 | Patel et al. |
| 6,447,796 B1 | 9/2002 | Vook et al. |
| 6,451,051 B2 | 9/2002 | Drasler et al. |
| 6,461,381 B2 | 10/2002 | Israel et al. |
| 6,464,722 B2 | 10/2002 | Israel et al. |
| 6,468,230 B2 | 10/2002 | Muni et al. |
| 6,488,701 B1 | 12/2002 | Nolting et al. |
| 6,488,703 B1 | 12/2002 | Kveen et al. |
| 6,506,203 B1 | 1/2003 | Boyle et al. |
| 6,540,773 B2 | 4/2003 | Dong |
| 6,554,855 B1 | 4/2003 | Dong |
| 6,602,285 B1 | 8/2003 | Von Oepen et al. |
| 6,616,682 B2 | 9/2003 | Joergensen et al. |
| 6,635,081 B2 * | 10/2003 | Khosravi ............... A61F 2/07 623/1.13 |
| 6,641,607 B1 | 11/2003 | Hossainy et al. |
| 6,645,239 B1 | 11/2003 | Park et al. |
| 6,656,204 B2 | 12/2003 | Ambrisco et al. |
| 6,669,717 B2 | 12/2003 | Marotta et al. |
| 6,669,961 B2 | 12/2003 | Kim et al. |
| 6,673,814 B2 | 1/2004 | Joshi et al. |
| 6,676,695 B2 | 1/2004 | Solem |
| 6,682,554 B2 | 1/2004 | Oepen et al. |
| 6,702,849 B1 | 3/2004 | Dutta et al. |
| 6,712,834 B2 | 3/2004 | Yassour et al. |
| 6,712,842 B1 | 3/2004 | Gifford, III et al. |
| 6,755,856 B2 | 6/2004 | Fierens et al. |
| 6,802,851 B2 | 10/2004 | Jones et al. |
| 6,808,533 B1 | 10/2004 | Goodwin et al. |
| 6,818,014 B2 | 11/2004 | Brown et al. |

(56) References Cited

U.S. PATENT DOCUMENTS

| | | | |
|---|---|---|---|
| 6,827,731 B2 | 12/2004 | Armstrong et al. |
| 6,835,189 B2 | 12/2004 | Musbach et al. |
| 6,893,457 B2 | 5/2005 | Dong |
| 6,902,522 B1 | 6/2005 | Walsh et al. |
| 6,918,920 B1 | 7/2005 | Wang et al. |
| 6,919,100 B2 | 7/2005 | Narayanan |
| 6,929,658 B1 | 8/2005 | Freidberg et al. |
| 6,932,832 B2 | 8/2005 | Patel et al. |
| 6,939,374 B2 | 9/2005 | Banik et al. |
| 6,939,375 B2 | 9/2005 | Sirhan et al. |
| 6,939,376 B2 | 9/2005 | Shulze et al. |
| 6,953,476 B1 | 10/2005 | Shalev |
| 6,981,986 B1 | 1/2006 | Brown et al. |
| 6,997,946 B2 | 2/2006 | Girton et al. |
| 7,011,676 B2 | 3/2006 | Dong |
| 7,037,330 B1 | 5/2006 | Rivelli, Jr. et al. |
| 7,041,129 B2 | 5/2006 | Rourke et al. |
| 7,077,859 B2 | 7/2006 | Sirhan et al. |
| 7,083,644 B1 | 8/2006 | Moroni |
| 7,118,585 B2 | 10/2006 | Addis |
| 7,163,554 B2 | 1/2007 | Williams et al. |
| 7,198,636 B2 | 4/2007 | Cully et al. |
| 7,198,638 B2 | 4/2007 | Dong |
| 7,264,631 B2 | 9/2007 | Dicarlo |
| 7,306,618 B2 | 12/2007 | Demond et al. |
| 7,306,623 B2 | 12/2007 | Watson |
| 7,320,697 B2 | 1/2008 | Demond et al. |
| 7,341,598 B2 | 3/2008 | Davidson et al. |
| 7,402,174 B2 | 7/2008 | Dong |
| 7,419,696 B2 | 9/2008 | Tuch |
| 7,435,254 B2 | 10/2008 | Chouinard et al. |
| 7,491,225 B2 | 2/2009 | Weber et al. |
| 7,604,650 B2 | 10/2009 | Bergheim |
| 7,641,680 B2 | 1/2010 | Palmas et al. |
| 7,666,221 B2 | 2/2010 | Escano |
| 7,722,634 B2 | 5/2010 | Panetta et al. |
| 7,806,919 B2 | 10/2010 | Bloom et al. |
| 7,811,314 B2 | 10/2010 | Fierens et al. |
| 7,815,763 B2 | 10/2010 | Fierens et al. |
| 7,854,760 B2 | 12/2010 | Molaei et al. |
| 7,867,247 B2 | 1/2011 | Pal et al. |
| 7,909,862 B2 | 3/2011 | Garrison et al. |
| 7,927,364 B2 | 4/2011 | Fierens et al. |
| 7,927,365 B2 | 4/2011 | Fierens et al. |
| 7,972,350 B2 | 7/2011 | McHale et al. |
| 7,996,993 B2 | 8/2011 | Gray et al. |
| 8,012,192 B2 | 9/2011 | Eidenschink et al. |
| 8,043,323 B2 | 10/2011 | Holzer et al. |
| 8,088,157 B2 | 1/2012 | Fierens et al. |
| 8,097,015 B2 | 1/2012 | Devellian |
| 8,109,987 B2 | 2/2012 | Kaplan et al. |
| 8,257,384 B2 | 9/2012 | Bates |
| 8,409,237 B2 | 4/2013 | Galdonik et al. |
| 8,435,285 B2 | 5/2013 | Shank et al. |
| 8,961,586 B2 | 2/2015 | Holzer et al. |
| 9,132,003 B2 | 9/2015 | Bar et al. |
| 10,058,440 B2 | 8/2018 | Bar et al. |
| 10,070,977 B2* | 9/2018 | Holzer ................. A61F 2/07 |
| 2002/0022860 A1 | 2/2002 | Borillo et al. |
| 2002/0111668 A1 | 8/2002 | Smith |
| 2002/0128679 A1 | 9/2002 | Turovskiy et al. |
| 2003/0100945 A1 | 5/2003 | Yodfat et al. |
| 2003/0176884 A1 | 9/2003 | Berrada et al. |
| 2004/0019373 A1* | 1/2004 | Casey, II ................. A61F 2/07 |
| | | 623/1.13 |
| 2004/0030377 A1 | 2/2004 | Dubson et al. |
| 2004/0068314 A1 | 4/2004 | Jones et al. |
| 2004/0267347 A1 | 12/2004 | Cervantes |
| 2005/0038503 A1 | 2/2005 | Greenhalgh et al. |
| 2005/0049680 A1 | 3/2005 | Fischell et al. |
| 2005/0163954 A1 | 7/2005 | Shaw |
| 2005/0187140 A1 | 8/2005 | Hunter et al. |
| 2005/0222607 A1 | 10/2005 | Palmer et al. |
| 2006/0009835 A1 | 1/2006 | Osborne et al. |
| 2006/0259137 A1 | 11/2006 | Artof et al. |
| 2007/0043428 A1 | 2/2007 | Jennings et al. |
| 2007/0204455 A1 | 9/2007 | Knott et al. |
| 2007/0208374 A1 | 9/2007 | Boyle et al. |
| 2007/0213805 A1* | 9/2007 | Schaeffer ................. A61F 2/07 |
| | | 623/1.13 |
| 2007/0270902 A1 | 11/2007 | Slazas et al. |
| 2008/0023346 A1 | 1/2008 | Vonderwalde |
| 2009/0012598 A1 | 1/2009 | Abbate et al. |
| 2009/0069880 A1 | 3/2009 | Vonderwalde et al. |
| 2009/0138070 A1 | 5/2009 | Holzer et al. |
| 2010/0056907 A1 | 3/2010 | Rappaport et al. |
| 2010/0204772 A1 | 8/2010 | Holzer et al. |
| 2010/0241214 A1 | 9/2010 | Holzer et al. |
| 2010/0324651 A1 | 12/2010 | Holzer et al. |
| 2010/0324664 A1 | 12/2010 | Holzer et al. |
| 2015/0374486 A1 | 12/2015 | Dickinson et al. |

FOREIGN PATENT DOCUMENTS

| | | |
|---|---|---|
| EP | 2074967 A1 | 7/2009 |
| WO | WO 198809683 A1 | 12/1988 |
| WO | WO 199929262 A1 | 6/1999 |
| WO | WO 200130266 A | 5/2001 |
| WO | WO 2003018079 A1 | 3/2003 |
| WO | WO 2003022325 A2 | 3/2003 |
| WO | WO 2006010130 A1 | 1/2006 |
| WO | WO 2006116636 A1 | 11/2006 |
| WO | WO 2006126182 A2 | 11/2006 |
| WO | WO 2007067451 A2 | 6/2007 |
| WO | WO 2008047367 A2 | 4/2008 |
| WO | WO 2008047368 A2 | 4/2008 |
| WO | WO 2008047369 A2 | 4/2008 |
| WO | WO 2008062414 A2 | 5/2008 |
| WO | 2009076350 A1 | 6/2009 |

OTHER PUBLICATIONS

European Patent Application No. 07827228.3, Search report from European Patent Office dated Mar. 8, 2013.

European Patent Application No. 07827415.6, Search report from European Patent Office dated Feb. 13, 2013.

Fayad et al., "Clinical Imaging of the High-Risk or Vulnerable Atherosclerotic Plaque," American Heart Association, Circulation Research, vol. 89, pp. 305-316, Aug. 17, 2001.

Haj et al., "Acquired Haemophilia A May be Associated with Clopidogrel," *British Medical Journal*, vol. 329, p. 323, Aug. 7, 2004.

International Application PCT/IB2011/055758, Written Opinion and International Search Report from International Searching Authority, dated May 14, 2012.

International Patent Application PCT/IL07/01253, Written Opinion and International Search Report from International Searching Authority, dated Jun. 13, 2008.

International Patent Application PCT/IL07/01254, Written Opinion and International Search Report from International Searching Authority, dated Sep. 30, 2008.

International Patent Application PCT/IL07/01255, Written Opinion and International Search Report from International Searching Authority, dated Sep. 25, 2008.

International Patent Application PCT/IL07/01442, Written Opinion and International Search Report from International Searching Authority, dated Aug. 27, 2008.

Liistro et al., "Late Acute Thrombosis After Paclitaxel Eluting Stent Implantation," *HEART Medical Journal*, vol. 86, pp. 262-264. Sep. 2001.

Nguyen et al., "Resistance to Clopidogrel: A Review of the Evidence," *Journal of the American College of Cardiology*, vol. 45, No. 8, pp. 1157-1164, Apr. 19, 2005.

Zakarija et al., "Clopidogrel-Associated TTP: An Update of Pharmacovigilance Efforts Conducted by Independent Researchers, Pharmaceutical Suppliers, and the Food and Drug Administration," *STROKE—Journal of American Heat Association*, vol. 35, pp. 533-537, Jan. 5, 2004.

CA Application # 3,013,758 Office Action dated Sep. 4, 2020.

(56) References Cited

OTHER PUBLICATIONS

IN Application # 201717011537 Office Action dated Sep. 22, 2020.
EP Application # 17195180.9 Office Action dated Oct. 30, 2020.
U.S. Appl. No. 16/260,427 Office Action dated May 10, 2021.

* cited by examiner

INTRAVASCULAR ANEURYSM TREATMENT DEVICE AND METHODS

CROSS-REFERENCE TO RELATED APPLICATIONS

This application is a continuation of U.S. patent application Ser. No. 12/791,008, filed Jun. 1, 2010, which is a continuation of U.S. patent application Ser. No. 12/513,851, filed May 6, 2009, which is a national stage of PCT/IL2007/001442, filed Nov. 21, 2007, which claims the benefit of U.S. Provisional Patent Application No. 60/860,486, filed Nov. 22, 2006, the disclosure of each of which is hereby incorporated herein by express reference thereto.

FIELD OF THE INVENTION

The present invention, in some embodiments thereof, relates to intravascular aneurysm treatment devices and methods and, more particularly, but not exclusively, to stent jackets designed to substantially reduce platelet aggregation, thus decreasing, even eliminating dependence on a platelet aggregation reducers.

BACKGROUND

Stents are now implanted in more than 70% of all percutaneous coronary revascularization procedures and routinely used in peripheral stenotic vasculature, for example stenotic carotid vessels and stenotic organ vasculature.

A typical stent is typically formed with large, mesh-like, apertures that damage surrounding stenotic vessel tissue during stent expansion. During the first two days following stent placement a layer of endothelial cells grows over the stent frame and the vessel, including the damaged tissue. The endothelial cells produce nitrites that prevent emboli and associated sequelae in all but 0.8% of a stent-recipient population.

While improving local circulation over the short term, stents do not remove the long-term danger of blockage in the very stenotic tissue that the stents treat as the damaged tissue is prone to form new scar tissue that protrude through the stent mesh, leading to vessel blockage, referred to as restenosis.

Tubular jackets comprising a polymer having small apertures are often deployed with a stent to prevent restenosis through the larger stent apertures. While often preventing restenosis, jacketed stents cause a significant increase in other life-threatening hazards. Groups of cells in the endothelial tissue coating polymer stent jackets are often unstable, presenting a lifetime risk of developing clumps comprising multiple endothelial cells that freely float through the circulation.

Platelets are sticky, irregularly shaped, disk-like blood-born bodies that promote blood clotting and readily sense, aggregate around, and stick to, clumps of free-floating endothelial cells. An embolism of aggregated platelets and endothelial cells presents a health threat that can form at any time following jacketed stent implantation; causing an estimated 2% of all jacketed stent recipients to eventually develop necrosis of vital organs and/or die.

Drug eluting jacketed stents, while reducing restenosis more than non-eluting jacketed stents, may pose and even greater threat of embolitic death than non-drug eluting stents.

("Late Acute Thrombosis After Paclitaxel Eluting Stent Implantation": F. Liistro; Heart; September 2001; Vol. 86, pages 262-264).

The tremendous and constant threat of emboli from jacketed stents has resulted in lifetime administration of prophylactic active pharmaceutical ingredients (APIs) including Clopidogrel Bisulfate, herein Clopidogrel, a platelet aggregation-reducing API marketed as Plavix® by Sanofi-Aventis and Bristol-Myers Squibb.

Clopidogrel administration is not hazard-free. Clopidogrel is associated with many side effects, including ulcers, skin rashes, syncope (temporary loss of consciousness), myelotoxicity (bone marrow damage), and TTP (thrombotic thrombocytopenic purpura), characterized by spontaneous, formation of assemblyic thrombi that form emboli. The death rate from TTP, even with immediate diagnosis and aggressive treatment, is approximately 30%.

("Clopidogrel-Associated TTP: An Update of Pharmacovigilance Efforts Conducted by Independent Researchers, Pharmaceutical Suppliers, and the Food and Drug Administration"; Zakarija, M D, et al; Stroke, February 2004, pages 533-537).

Moreover, Clopidogrel may not prevent life-threatening emboli as current data shows that up to 30% of Clopidogrel recipients fail to develop sufficiently reduced platelet aggregation.

("Resistance To Clopidogrel: A Review Of The Evidence": Nguyen MSc, Pharm, et al; Journal of the American College of Cardiology; 19 Apr. 2005; Vol. 45, Issue 8, pages 1157-1164).

Moreover, conditions such as hereditary antithrombin deficiency (HD), are that not responsive to platelet aggregate prophylactic APIs such as Clopidogrel. HD patients receiving Clopidogrel pose a unique at-risk population as HD is often diagnosed only following a serious embolitic event.

Further, people stricken with Auto Immune Deficiency Syndrome (AIDS) may actually develop hemophilia as a result of Clopidogrel administration. Within the AIDS population, a sub-population particularly at risk for developing hemophilia includes individuals having low CCR5 (CCR5 Delta 32 homozygous genotype), which is resistant to infection with HIV-1.

Additionally those at risk for acquiring hemophilia appear to be in the population group of immune-suppressed individuals, including geriatrics diabetics and those in the early stages of an HIV infection.

("Acquired Haemophilia May Be Associated With Clopidogrel" Montaser Haj et al; British Medical Journal August 2004; pages 329:323).

In addition to the health hazards affecting the above-noted population groups, there are significant risks to every jacketed stent recipient receiving lifetime Clopidogrel.

To prevent excessive bleeding in conjunction with virtually any surgery, Clopidogrel administration must be ceased for a significant period of time both pre-operatively and post-operatively. As a result, patients and surgeons are presented with a Hobson's choice of ceasing Clopidogrel administration and risking death from emboli or continuing Clopidogrel and risking embolism-free bleeding, hemorrhage and death.

In general, jacketed stents, while aiding in preventing restenosis, are associated with many significant, as yet unsolved, problems that can result in death.

There is thus a widely recognized need for a stent jacket that does not require the administration of a platelet aggregation reducing API and it would be highly advantageous to have, a stent devoid of the above limitations.

SUMMARY

An intravascular device configured to treat an aneurysm, which includes a support structure including metal struts configured to be positioned in a body lumen and defining a central fluid passage that extends axially along the support structure, and a knitted mesh cover disposed over an exterior of the support structure, wherein the cover extends across a radial arc and along a length of the support structure sufficient to exceed an opening of an aneurysm to be treated and the cover includes a polymer fiber having a diameter of at least 40 nanometers to 30 microns arranged to provide apertures through the cover which apertures are at least 20 microns and are sized to minimize or prevent an aneurysm-filling material from exiting the aneurysm through the knitted mesh cover and support structure into the central fluid passage.

In one embodiment, the aneurysm-filling material includes one or more coils. In another embodiment, a porous structure is disposed over the aneurysm-filling material to increase the surface area of the aneurysm-filling material. In yet a further embodiment, the device minimizes or prevents the aneurysm-filling material from protruding from the aneurysm into the central fluid passage. In a preferred embodiment, a second knitted mesh cover is disposed out of phase over the knitted mesh cover to further minimize or prevent the aneurysm-filling material from protruding from the aneurysm.

In another embodiment, the apertures have a diameter of more than 100 microns to below 300 microns. In a further embodiment, the apertures have a minimum center dimension of approximately 150 microns by 200 microns. In yet another embodiment, the nominal aperture size is no greater than 200 microns. In a further embodiment, the aperture diameter is smaller than 100 microns. In yet another embodiment, the nominal aperture size is no greater than 50 microns. In various embodiments, the device further minimizes or prevents embolism-causing debris from entering the central fluid passage.

In a second aspect, the disclosure encompasses an intravascular device configured to treat an aneurysm, which includes a support structure including metal struts configured to be positioned in a body lumen and defining a central fluid passage that extends axially along the support structure; and a knitted mesh cover disposed over an exterior of the support structure, wherein the cover extends across a radial arc and along a length of the support structure sufficient to exceed an opening of an aneurysm to be treated and the cover includes a polymer fiber having a diameter of at least 40 nanometers to 30 microns arranged to provide apertures through the cover, the apertures being sized to prevent blood from passing through the device to prevent further expansion of the aneurysm.

In one embodiment, the device promotes clot formation within the aneurysm. In another embodiment, the knitted mesh cover does not extend across the entire support structure to avoid restricting blood flow to a branching vessel. In yet a further embodiment, the knitted mesh cover has smaller apertures on an aneurysm-facing side of the support structure to restrict blood flow therethrough relative to larger apertures on an opposite side of the support structure to permit blood flow to a branching vessel. In yet a further embodiment, the knitted mesh cover prevents embolism-causing debris from entering the lumen from an aneurysm.

In a third aspect, the disclosure encompasses an intravascular device configured to treat an aneurysm, which includes at least one knitted mesh structure configured to be positioned in a body lumen and defining a central fluid passage that extends axially along the body lumen, wherein the structure extends across a radial arc of the lumen and along a length of the lumen sufficient to exceed an opening of an aneurysm to be treated, and the structure includes a polymer fiber having a diameter of at least 40 nanometers to 30 microns arranged to provide apertures through the structure, the apertures being sized to prevent blood from passing through the device to prevent further expansion of the aneurysm, wherein structure is formed of a self-expanding material that provides sufficient radial force to hold itself in place against the aneurysm. In one embodiment, the radial pressure applied to the body lumen by the knitted mesh structure is equivalent to about 1 atmosphere.

In a fourth aspect, the disclosure encompasses a method of treating an aneurysm which includes positioning the intravascular device of claim 1 adjacent to an aneurysm in a body lumen of a patient in need of aneurysm therapy. In one embodiment, the aneurysm is a cerebral aneurysm.

In further aspects, the disclosure also encompasses the following: A stent assembly that includes a stent configured to be positioned in a body lumen, and a knitted stent jacket including an expansible mesh structure having a coverage area of less than 25%, having approximate aperture diameters greater than 20 micrometers, and surrounding an external surface of the stent and coaxially associated therewith, wherein the stent assembly elutes an amount of an active pharmaceutical agent. In one embodiment, the active pharmaceutical agent is eluted from the stent. In another embodiment, the active pharmaceutical agent is eluted from a coating disposed over a portion of the stent. In yet another embodiment, the active pharmaceutical agent is time-released according to a predetermined treatment schedule. In one embodiment, the treatment schedule covers a period of 8 hours to a plurality of months. In a different embodiment, the active pharmaceutical agent is eluted from the knitted stent jacket. In yet a further embodiment, the active pharmaceutical agent is eluted from a coating on the expansible mesh structure. In another embodiment, the coaxial association includes the knitted stent jacket being sewed, adhered, glued, folded, or sutured to the stent. In one preferred embodiment, the coaxial association is that the knitted stent jacket is sutured to the stent.

In one embodiment, a proximal portion of the knitted stent jacket is attached to a proximal portion of the stent. In a preferred embodiment, a distal portion of the stent jacket is attached to a distal portion of the stent. In another preferred embodiment, the amount of active pharmaceutical agent eluted includes a therapeutically effective amount. In yet another embodiment, the active pharmaceutical agent is eluted from the stent, a coating on the stent, the knitted stent jacket, a coating on the knitted stent jacket, or any combination thereof. In yet a further embodiment, a second, different active pharmaceutical agent is eluted from the stent, a coating on the stent, the knitted stent jacket, a coating on the knitted stent jacket, or any combination thereof. In yet another embodiment, the mesh structure is formed from a polymer component including one or more poly lactic-co-polyglycolic ("PLGA"), polycaprolactone ("PCL"), polygluconate, polylactic acid-polyethylene oxide, poly(hydroxybutyrate), polyanhydride, poly-phosphoester, poly(amino acids), poly-L-lactide, poly-D-lactide, polyglycolide, or poly(alpha-hydroxy acid) co-polymer(s), polyethylene terephthalate, or any combination thereof. In one preferred embodiment, the mesh structure includes a single polymer fiber or a plurality of individual polymer fibers. In another preferred embodiment, the polymer is elastic, biocompatible, and hemocompatible. In another embodiment, the knitted stent jacket includes a mesh of knit fibers each having diameter from approximately 7 to 40 micrometers. In a different embodiment, the expansible mesh structure includes a retracted state and a deployed state, and further wherein the expansible mesh structure defines apertures having a minimum center dimension of 150 micrometers to 200 micrometers in the deployed state. In one preferred embodiment, the expansible mesh structure includes a retracted state and a deployed state, and further wherein the expansible mesh structure defines apertures having a minimum center dimension of 150 micrometers to 180 micrometers in the deployed state.

In one embodiment, the active pharmaceutical agent includes a liposome, a steroid, a statin, an anticoagulant, gemcitabine, zolimus or zotarolimus, sirolimus, taxol/paclitaxel, or a combination thereof. In another embodiment, the active pharmaceutical agent includes zolimus, sirolimus, taxol/paclitaxel, or a combination thereof. In a further embodiment, the active pharmaceutical agent includes an anti-proliferative agent, an antithrombotic agent, and anti-oxidant, a growth factor inhibitor, a collagen inhibitor, a liposome, a steroid or corticosteroid, a statin, endothelial cell seeds, a hydrogel containing endothelial cells, or a combination thereof. In one preferred embodiment, the anti-proliferative agent is present and includes sirolimus, zolimus or zotarolimus, a taxane, tacrolimus, everolimus, vincritine, viblastine, a HMG-CoA reductase inhibitor, doxorubicin, colchicine, actinomycin D, mitomycin C, cyclosporine, mycophenolic acid, triazolopyrimidine, or a combination thereof; wherein the antithrombotic agent is present and includes heparin, a heparin-like dextran derivative, acid citrate dextrose, coumadin, warfarin, streptokinase, anistreplase, tissue plasminogen activator (tPA), urokinase, abciximab, or a combination thereof; wherein the growth factor inhibitor is present and includes tranilast, angiopeptin, or a combination thereof; wherein the steroid or corticosteroid is present and includes cortisone, prednisolone, or both; wherein the statin is present and includes simvastatin, lovastatin, or a combination thereof; or any combination of the foregoing.

In one embodiment, the stent assembly includes 1 microgram to 200 micrograms of each pharmaceutical agent. In another embodiment, the mesh of the knitted stent jacket includes 1 microgram to 200 micrograms of each pharmaceutical agent. In one specific embodiment, the stent has a surface that includes around 1 µg/mm$^2$ of taxol. In one embodiment, the active pharmaceutical agent includes a 'limus drug at a concentration of 10 µg/mm$^2$ to 80 µg/mm$^2$. In another embodiment, the active pharmaceutical agent includes a 'limns drug at a concentration of 80 µg/mm$^2$ to 140 µg/mm$^2$. In a further embodiment, the knitted stent jacket is uncoated.

In one preferred embodiment, the stent includes a metal alloy coated with a biodegradable polymer, biostable polymer, bioresorbable polymer, or a combination thereof. In another preferred embodiment, the stent includes a biodegradable material. In one embodiment, the biodegradable material includes a polymer. In yet another embodiment, the biodegradable material includes a metal alloy.

The disclosure also encompasses, in a second aspect, a stent assembly, including a stent configured to be positioned in a body lumen, which stent includes a metal alloy coated with a bioresorbable polymer, biostable polymer, biodegradable polymer, or a combination thereof; and a knitted stent jacket including an expansible mesh structure having a coverage area of less than 25% and surrounding an external surface of the stent, where a distal and a proximal portion of the stent jacket is attached to a distal and proximal aspect of the stent, wherein the stent elutes a therapeutically effective amount of an active pharmaceutical agent including zolimus or zotarolimus, sirolimus, taxol/paclitaxel, or a combination thereof. In one preferred embodiment, the mesh structure is formed from a polymer component including one or more poly lactic-co-polyglycolic ("PLGA"), polycaprolactone ("PCL"), polygluconate, polylactic acid-polyethylene oxide, poly(hydroxybutyrate), polyanhydride, poly-phosphoester, poly(amino acids), poly-L-lactide, poly-D-lactide, polyglycolide, or poly(alpha-hydroxy acid) co-polymer(s), polyethylene terephthalate, or any combination thereof.

According to another aspect of the present invention there is provided a method of stenting, including: implanting a stent assembly in a vessel of a subject, the stent assembly, including: a stent jacket, including an expansible mesh structure, formed of fibers of a diameter between about 7 micrometers and about 18 micrometers, the diameter having a property of forming a substantially stable layer of endothelial cells, covering the fibers, thus reducing platelet aggregation, and an expansible stent, operatively associated with the stent jacket. The method further includes administering to the subject an active pharmaceutical ingredient (API) including a platelet aggregation reducer for a shortened time period, not exceeding six months, the shortened time period being a consequence of the property.

In embodiments, the shortened time period does not exceed five months.

In embodiments, the shortened time period does not exceed four months.

In embodiments, the shortened time period does not exceed three months.

In embodiments, the shortened time period does not exceed two months.

In embodiments, the shortened time period does not exceed one month.

In embodiments, during the shortened time period, the subject displays a reaction to the platelet aggregation reducer, and further including eliminating the administration of the platelet aggregation reducer.

In embodiments, the reaction is selected from the group consisting of ulcers, skin rashes, syncope, myelotoxicity and thrombotic thrombocytopenic purpura (TTP).

In embodiments, during the shortened time period, the subject displays a condition requiring eliminating administration of the platelet aggregation reducer, the condition from the group of conditions including: unresponsiveness to a platelet aggregate reducing API, an antithrombin deficiency, hereditary antithrombin deficiency (HD), immune depression, low CCR5 Delta 32 homozygous genotype (CCR5), acquired hemophilia, Immune Deficiency Syndrome (AIDS), and HIV.

According to an aspect of the present invention there is provided a method of stenting, including implanting a stent assembly in a vessel of a subject, the stent assembly, including a stent jacket, including an expansible mesh structure, formed of fibers of a diameter between about 7 micrometers and about 18 micrometers, the diameter having a property of forming a substantially stable layer of endothelial cells, covering the fibers, thus reducing platelet aggregation, and an expansible stent, operatively associated with the stent jacket. The method further includes eliminating drug administration to the subject in consequence of the property.

In embodiments, the diameter is between about 10 micrometers and about 15 micrometers.

In embodiments, the diameter is between about 11 micrometers and about 14 micrometers.

In embodiments, the diameter is between about 12 micrometers and about 13 micrometers.

In embodiments, the diameter is between about 12.5 micrometers. In embodiments, the mesh is formed as a single knit. In embodiments, the fiber is formed from multiple filaments.

In embodiments, the expansible mesh structure includes a retracted state and a deployed state, and further wherein in the deployed state, the expansible mesh structure defines apertures, having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow.

In embodiments, the minimum center dimension is greater than about 200 micrometers.

In embodiments, the fibers are formed of a material, which encourages stable adherence of endothelial cells to the fibers.

In embodiments, the material is selected from the group consisting of: stainless steel, nitinol, titanium, gold, a biostable polymer, and a natural polymer.

According to an aspect of the present invention there is provided a method of stenting, including: implanting a stent assembly in a vessel of a subject, the stent assembly, including a stent jacket, including an expansible mesh structure, having a retracted state and a deployed state, and further wherein in the deployed state, the expansible mesh structure defines apertures, having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow, and an expansible stent, operatively associated with the stent jacket. The method further includes administering to the subject an active pharmaceutical ingredient (API) including a platelet aggregation reducer for a shortened time period, not exceeding six months, the shortened time period being a consequence of the minimum center dimension.

In embodiments, the shortened time period does not exceed five months.

In embodiments, the shortened time period does not exceed four months.

In embodiments, the shortened time period does not exceed three months.

In embodiments, the shortened time period does not exceed two months.

In embodiments, the shortened time period does not exceed one month.

In embodiments, during the shortened time period, the subject displays a reaction to the platelet aggregation reducer, and further including eliminating the administration of the platelet aggregation reducer.

In embodiments, the reaction is selected from the group consisting of ulcers, skin rashes, syncope, myelotoxicity and TTP.

In embodiments, during the shortened time period, the subject displays a condition requiring eliminating administration of the platelet aggregation reducer, the condition from the group of conditions including: unresponsiveness to a platelet aggregate reducing API, an antithrombin deficiency, HD, immune depression, low CCR5, acquired hemophilia, AIDS, HIV.

According to an aspect of the present invention there is provided a method of stenting, including implanting a stent assembly in a vessel of a subject, the stent assembly, including a stent jacket, including an expansible mesh structure, having a retracted state and a deployed state, and further wherein in the deployed state, the expansible mesh structure defines apertures, having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow, and an expansible stent, operatively associated with the stent jacket. The method further includes eliminating drug administration to the subject, in consequence of the minimum center dimension.

In embodiments, wherein the minimum center dimension is greater than about 200 micrometers.

In embodiments, wherein the expansible mesh structure is formed of fibers of a diameter between about 7 micrometers and about 18 micrometers, the diameter having a property of forming a substantially stable layer of endothelial cells, covering the fibers, thus reducing platelet aggregation.

In embodiments, the diameter is between about 10 micrometers and about 15 micrometers.

In embodiments, the diameter is between about 11 micrometers and about 14 micrometers.

In embodiments, the diameter is between about 12 micrometers and about 13 micrometers.

In embodiments, the diameter is between about 12.5 micrometers.

In embodiments, the mesh is formed as from single fiber. In embodiments, the fibers are formed from multiple filaments.

In embodiments, the fibers are formed of a material, which encourages stable adherence of endothelial cells to the fibers.

In embodiments, the material is selected from the group consisting of: stainless steel, nitinol, titanium, gold, a biostable polymer, and a natural polymer.

According to an aspect of the present invention there is provided a stent assembly, including: a stent jacket, including an expansible mesh structure, formed of fibers of a diameter between about 10 micrometers and about 15 micrometers, the diameter having a property of forming a substantially stable layer of endothelial cells, covering the fibers, thus reducing platelet aggregation, and an expansible stent, operatively associated with the stent jacket.

In embodiments, the diameter is between about 11 micrometers and about 14 micrometers.

In embodiments, the diameter is between about 12 micrometers and about 13 micrometers.

In embodiments, the diameter is between about 12.5 micrometers.

In embodiments, the mesh is formed as a single knit. In embodiments, the fibers are formed from multiple filaments.

In embodiments, the expansible mesh structure includes a retracted state and a deployed state, and further wherein in the deployed state, the expansible mesh structure defines apertures, having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow.

In embodiments, the minimum center dimension is greater than about 200 micrometers.

In embodiments, the fibers are formed of a material, which encourages stable adherence of endothelial cells to the fibers.

In embodiments, the material is selected from the group consisting of: stainless steel, nitinol, titanium, gold, a biostable polymer, and a natural polymer.

According to an aspect of the present invention there is provided a stent assembly, including: a stent jacket, including an expansible mesh structure, having a retracted state and a deployed state, and further wherein in the deployed state, the expansible mesh structure defines apertures, having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow, and an expansible stent, operatively associated with the stent jacket.

In embodiments, the minimum center dimension is greater than about 200 micrometers.

In embodiments, the expansible mesh structure is formed of fibers of a diameter between about 7 micrometers and about 18 micrometers, the diameter having a property of forming a substantially stable layer of endothelial cells, covering the fibers, thus reducing platelet aggregation.

In embodiments, the diameter is between about 10 micrometers and about 15 micrometers.

In embodiments, the diameter is between about 11 micrometers and about 14 micrometers.

In embodiments, the diameter is between about 12 micrometers and about 13 micrometers.

In embodiments, the diameter is between about 12.5 micrometers. In embodiments, the mesh is formed as a single knit. In embodiments, the fibers are formed from multiple filaments.

In embodiments, the fibers are formed of a material, which encourages stable adherence of endothelial cells to the fibers.

In embodiments, the material is selected from the group consisting of: stainless steel, nitinol, titanium, gold, a biostable polymer, and a natural polymer.

Unless otherwise defined, all technical and/or scientific terms is used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Exemplary non-limiting embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

Figure 1:
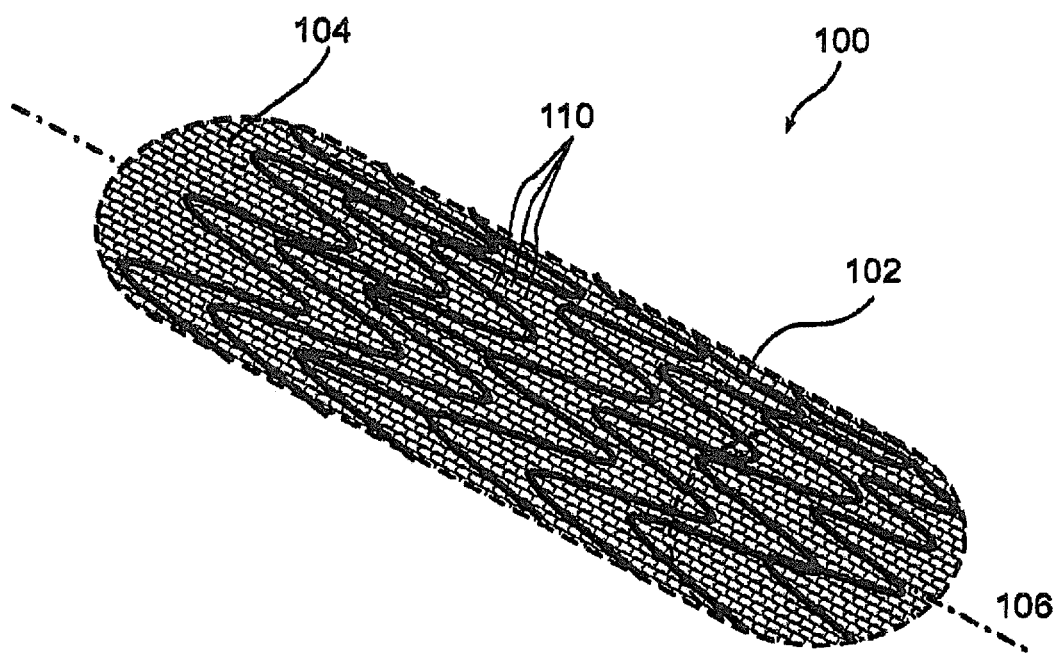
FIG. 1 is a perspective view of an enhanced stent apparatus, in an open, non-crimped mode, in accordance with an exemplary embodiment of the invention.

The instant application is divided into a number of labeled sections which generally include, in order, descriptions of apparatuses (e.g. porous structures, stents, etc.), materials and methods for manufacturing the apparatuses, the usage of pharmaceuticals with the apparatuses and methods of using the apparatuses. It should be understood that the section headings are for clarity only, and are not intended to limit the subject matter described therein. Furthermore, some of the subject matter described in a particular section may belong in more than one section and therefore, some of the material could overlap between sections.

INTRODUCTION

Aspects of the present invention successfully address shortcomings of the prior art by providing a stent assembly having a low-bulk mesh jacket designed to promote a stable layer of endothelial cells.

In accordance with some embodiments of the present invention, the mesh comprises a fiber having a low diameter that allows each endothelial cell to fully cover and overlap each fiber, thereby forming a layer of endothelial cells that adhere to tissue on either side of the fiber. The thus formed endothelial layer is substantially stable with a substantially reduced tendency to break away and form emboli.

In accordance with some embodiments of the present invention, the mesh fiber comprises material that encourages adherence of endothelial cells, thereby encouraging endothelial layer stability.

In accordance with some embodiments of the present invention, the mesh is not secondarily processed for example with a chemical coating that may diminish endothelial adherence. Additionally, the absence of chemical coatings serves to maintain low bulk fibers and fiber junctions, where a first fiber passes over or under a second fiber-another feature that contributes to endothelial layer stability.

In accordance with some embodiments of the present invention, each mesh fiber is spaced a distance from a neighboring fiber thereby preventing a single endothelial cell from adhering to more than one fiber, thereby reducing the chance that endothelial cells will break free of the stent, for example as a result of natural stent pulsation during blood flow.

In accordance with some embodiments of the present invention, the stent jacket optionally comprises a mesh that is knitted. In accordance with some embodiments of the present invention, the stent jacket mesh is optionally formed from a single fiber or a single group of fibers.

Overview of Enhanced Stent Apparatus

The present invention, in some embodiments thereof, relates to stent assemblies, as presented in PCT Patent Application PCT/IB2006/051874, the disclosure of which is hereby incorporated herein by express reference thereto.

In an exemplary embodiment of the invention, an apparatus is provided which includes a porous structure and, optionally, an underlying support element, such as a stent (wherein underlying means the porous structure is between the support element and a lumen wall).

In some exemplary embodiments of the invention, an enhanced stent apparatus, including the porous structure and a stent, is used to treat stenosis and/or restenosis. In some exemplary embodiments of the invention, the enhanced stent apparatus furnishes at least one of a multiplicity of benefits over a conventional arterial stent. For example, the enhanced stent apparatus is optionally used to prevent plaque from getting into the blood stream to cause embolism, since the porous structure is made with small enough apertures (sizes indicated below) to hold detached plaque in place. In an embodiment of the invention, use of a porous structure replaces the use of an embolism protection device during stent implantation. Optionally, the "umbrella" type embolism protection device is not used. Optionally, the porous structure is used in conjunction with an embolism protection device for enhanced protection over the method of using an embolism protection device during the implantation of a conventional arterial stent. In an embodiment of the invention, the enhanced stent apparatus delivers more comprehensive pharmacological assistance to a treated area than conventional stents. In some embodiments of the invention, the enhanced stent apparatus is optimized to encourage endothelial cell growth and/or migration.

FIG. 1 shows a perspective view of an enhanced stent apparatus 100, in an exemplary embodiment of the invention. A support element 102 is designed and constructed to expand a blood vessel in a radial fashion from a central axis 106 of the enhanced stent apparatus 100. Optionally, support element 102 is tubular in shape. In some exemplary embodiments of the invention, support element 102 is constructed of a flexible, biocompatible material. Optionally, support element 102 is constructed of stainless steel, nitinol, and/or cobalt chromium and/or other metal alloys (e.g. magnesium alloy). Optionally, support element 102 is constructed of polymer either biostable or bioresorbable. In some exemplary embodiments of the invention, support element 102 is a vascular stent, such as those made by Cordis®, Boston Scientific® and/or Medtronic®, for example.

Figure 2:
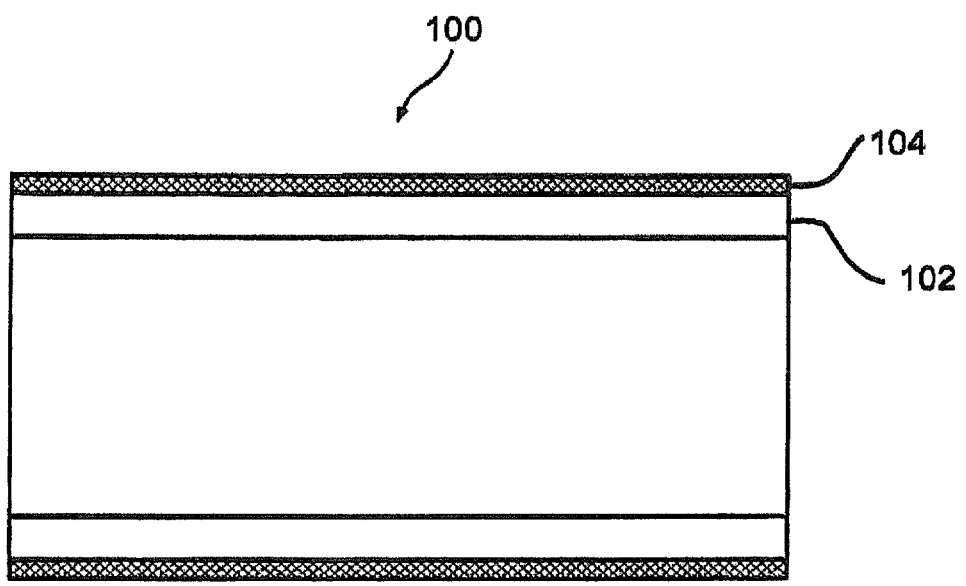
FIG. 2 is a cross-sectional side view of an enhanced stent apparatus, in accordance with an exemplary embodiment of the invention.

In an exemplary embodiment of the invention, support element 102 is covered by at least one porous structure 104. Optionally, support element 102 acts as a support structure for porous structure 104, for example to provide radial support and or to maintain a desired shape of porous structure 104. FIG. 2, shows a cross-sectional view of an enhanced stent apparatus. In this embodiment, support element 102 supplies structural support to porous structure 104, which is located on the exterior of support element 102.

In some exemplary embodiments of the invention, porous structure 104 is laid on the exterior of support element 102 and thereby overlaps gaps in support element 102 (making the aperture sizes of the device as a whole smaller, for example 150 microns), since conventional stent construction usually results in multiple gaps in the structure of the stem, typically several millimeters. In other exemplary embodiments of the invention, porous structure 104 covers only a portion of support element 102. For example, only a portion of support element 102 is covered to avoid restricting luminal flow to a branching vessel.

Figure 10:
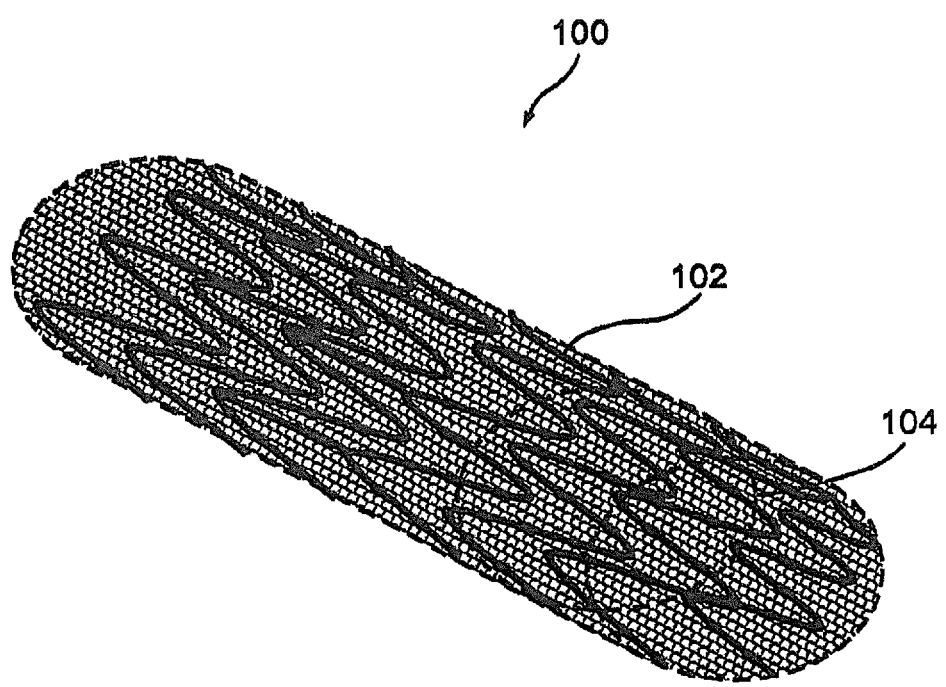
FIG. 10 is a perspective view of an enhanced stent apparatus, wherein porous structure is longer than the support element, in accordance with an exemplary embodiment of the invention.

In some exemplary embodiments of the invention, porous structure 104 extends past at least one end of support element 102. This can, for example, better treat the inside surface of a blood vessel at an edge of enhanced stent apparatus 100, where it is more likely to have restenosis. In an exemplary embodiment of the invention, porous structure 104 pads and/or treats trauma caused by the edge of support element 102 by extending past at least one end of support element 102. Optionally, porous structure 104 extends no more than 1 mm past the end of support element 102. Optionally, porous structure 104 extends over 1 mm past the end of support element 102. Optionally, porous structure 104 extends past only one end or both ends (as shown in FIG. 10) of support element 102.

In some exemplary embodiments of the invention, porous structure 104 is attached to support element 102 to prevent porous structure 104 from unraveling and/or causing tissue irritation and/or avoiding dislodgment of the porous structure from the support element during deployment. Optionally, the end of porous structure 104 is folded over the end of support element 102 and attached, providing padding to a potentially trauma causing edge. Optionally, the end of porous structure 104 is folded under itself and is held folded due to the pressure between the support element and the lumen. In an embodiment of the invention, a treatment, such as heat, is used to make the fold sharp and/or permanent.

It should be understood that while an exemplary configuration of enhanced stent apparatus is shown in FIGS. 1 and 2, other configurations could possibly be used, including: a porous structure 104 over a pharmaceutical eluting support element; a pharmaceutical eluting porous structure over a support element 102; a pharmaceutical to eluting porous structure over a pharmaceutical eluting support element; a support element in between at least two porous structures, optionally some or all eluting pharmaceuticals; and, an enhanced stent comprised of a plurality of layers which exhibit different optional characteristics such as degradation time and/or pharmaceutical elution. It should be understood that any of the above configurations include biodegradable and/or bioresorbable materials. Optionally, configurations are chosen for specific treatment regimens indicated by the condition of the patient.

In some exemplary embodiments of the invention, porous structure 104 is used to control the local pressure exerted by the enhanced stent apparatus on the body lumen wall. For example, by increasing or decreasing the coverage area of the porous structure as it at least partially covers the stent, the pressure exerted by the enhanced stent apparatus per unit area can be altered. In some embodiments of the invention, modification of the coverage area considers factors such as the stiffness of support element 102 and the geometry and/or coverage area of the support struts of support element 102.

In an embodiment of the invention, pressure control is used to reduce the likelihood of the enhanced stent apparatus causing plaque to break off of the lumen wall. In some embodiments of the invention, pressure control is used to reduce tissue trauma typically caused by stent implants, thereby enhancing protection against stenosis/restenosis. Furthermore, in some embodiments of the invention, support element 102 struts which could not be used previously due to the likelihood of trauma to the lumen tissue can optionally be used in combination with porous structure 104.

In some exemplary embodiments of the invention, bile ducts are treated using at least a porous structure as described herein. For example, the bile ducts often become congested with debris (e.g. cholesterol) which restricts flow. Treatment of the bile ducts using enhanced stent apparatus may increase the diameter of the bile ducts, improving their operation.

It is known that varying types of body lumens possess varying surface textures, both varying from each other, and sometimes within one type of lumen. Thus, in some exemplary embodiments of the invention, different porous structures with varying surface texture configurations are manufactured and/or used depending on the interior surface texture of a lumen being treated. For example, peaks and valleys in a body lumen are fitted with counter peaks and valleys of a porous structure (i.e. porous structure counter peak goes into lumen valley and porous structure counter valley accepts lumen peak). Optionally, the counter peaks and valleys are of the same magnitude as the peaks and valleys found in the lumen being treated.

It should be understood that the aperture size, the porous structure thickness, the fiber thickness (or French), and/or the coverage area are varied for different applications. For example when treating the carotids, debris of more than 100 microns should be prevented from reaching the brain, thus the porous structure is designed such that when stent is expanded, usually to about 8 millimeters, the majority of aperture sizes are less than 100 microns. As another example, when treating the coronaries larger debris (>100 microns) is not as problematic, while the endotheliazation process and the non-restriction of flow to side branches is more important. Thus for coronary artery applications, when the support element 102 is in an expanded position, usually about 3 millimeters in diameter, the apertures in the porous structure are optionally larger than 100 microns and below 300 microns. In some embodiments of the invention, the rate of endothelium cell growth over porous structure may be modified by increasing and/or decreasing fiber thickness and porous structure thickness.

Figure 8:
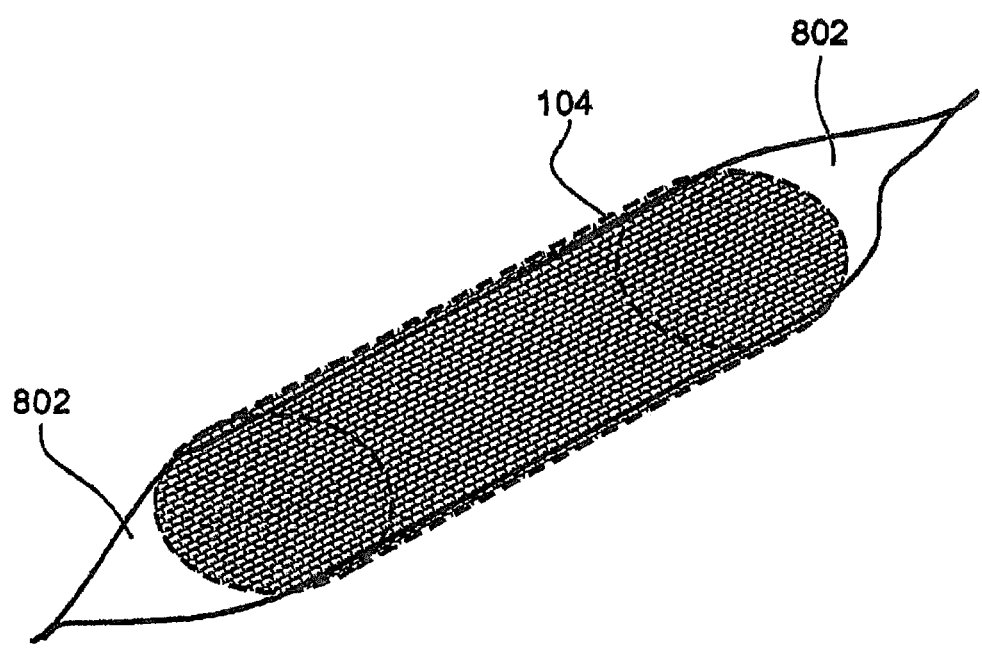
FIG. 8 is a perspective view of an enhanced stent apparatus on an angioplasty balloon, in accordance with an exemplary embodiment of the invention.

In some exemplary embodiments of the invention, porous structure 104 is used with a balloon expandable support element 102. In some exemplary embodiments of the invention, porous structure 104 is placed directly on an expandable balloon 802 without or with support element 102, for example as shown in FIG. 8. In some exemplary embodiments of the invention, the balloon catheter may extend past a proximal and/or distal end of support element 102. It is optionally desirable to provide porous structure 104 which extends past the end of support element 102 to provide a buffer between the balloon and the blood vessel, and optionally to provide pharmaceutical treatment to regions to which the underlying support element 102 does not extend, but may be exposed to the balloon.

In an exemplary embodiment of the invention, porous structure 104 is under 100 microns in thickness. In some exemplary embodiments of the invention, the porous structure is less than 30 microns thick. Optionally, the porous structure is less than 10 microns in thickness. For example, the porous structure is less than 5 microns or 1 micron thick. Porous structure 104 is optionally comprised of at least one fine, thread-like fiber. In some exemplary embodiments of the invention, porous structure 104 is comprised of at least one fiber that is 40 nm to 40 microns thick. Optionally, to the fiber thickness is similar to or less than the diameter of an endothelial cell to encourage endothelial cell growth between fibers and/or around at least one fiber. In an exemplary embodiment of the invention, a super-fiber is used to construct porous structure 104, wherein the super-fiber is made of multiple fibers braided together. Optionally, super-fibers are used to enhance the strength of porous structure 104.

In an exemplary embodiment of the invention, the fibers of porous structure 104 are spun and/or knitted and/or woven and/or braided to provide structure to and apertures 110 in porous structure 104. Optionally, the porous structure is woven in an even pattern. Optionally, the porous structure is constructed so that the fibers are randomly positioned in porous structure 104. Optionally, polymer fibers are used to construct porous structure 104. Optionally, polymer coverings are applied to porous structure 102 and/or support element 102. Exemplary porous structure manufacture is described in more detail in the "Methods of Manufacture" section below.

In an exemplary embodiment of the invention, the polymer covered porous structure 104 is optionally made out of a closed interlocked design and/or an open interlocked design, or semi open design, similar to typical support element 102 designs. The open interlocked design has an advantage when side branching is needed. When treating a junction of two blood vessels, there is sometimes a need to introduce one stent through the side of another one. An open interlocked design allows such a procedure, and when the porous structure is made of metal mesh, an open interlocked design is utilized in order to allow easy side branching stents. Optionally, using a biodegradable polymer coating on a non-biodegradable support element 102 leaves the support element 102 embedded after the biodegradable polymer has degraded.

In an exemplary embodiment of the invention, porous structure 104 is crimped to a small diameter while still maintaining its flexibility, to enable successful maneuverability through a patient's blood vessels to the site where enhanced stent apparatus 100 is to be implanted. In an exemplary embodiment of the invention, porous structure 104 is expandable to enable expansion of porous structure 104 with support element 102 upon deployment at a treatment site within a patient's blood vessel. Optionally, expansion of porous structure 104 along the longitudinal axis matches the expansion of support element 102 along the longitudinal axis.

Figure 9:
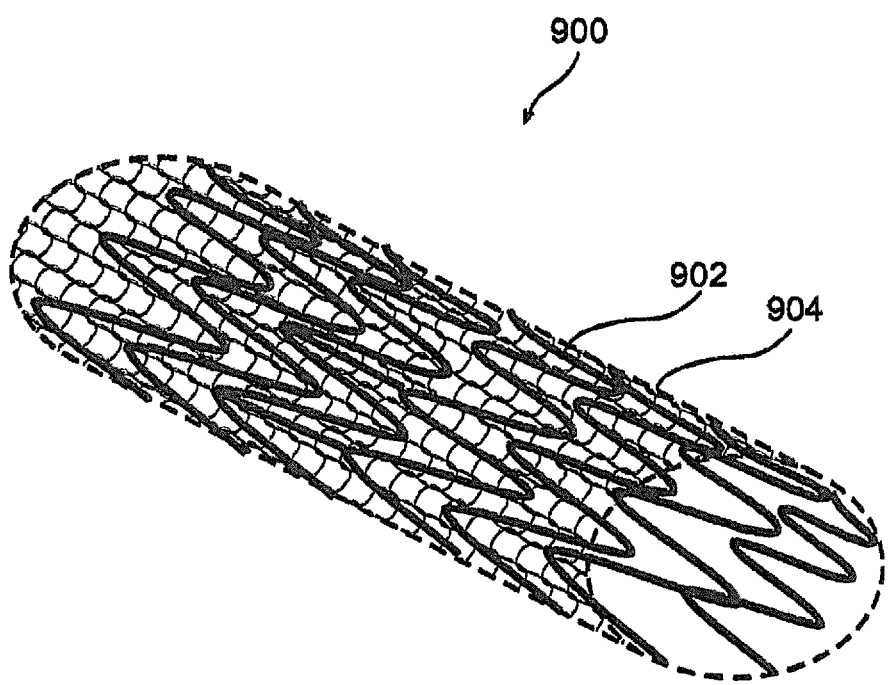
FIG. 9 is a perspective view of an enhanced stent apparatus, provided with longitudinal non-stretchable wires, and horizontal stretchable elastomers in accordance with an exemplary embodiment of the invention.

In an exemplary embodiment of the invention, at least porous structure 104 is expandable without significant foreshortening or elongation of the length of porous structure 104. Optionally, porous structure 104 expands differently than support element 102, for example using sliding connections described herein. As described elsewhere herein, in a knitted embodiment of porous structure 104, expansion occurs at least partially as a result of the knitted structure, and not necessarily because of the elasticity of the fiber used in constructing porous structure 104. In an embodiment of the invention, at least one fiber which comprises porous structure 104 is provided with slack during manufacture to provide additional fiber material when porous structure 104 expands. FIG. 9 shows a perspective view of an enhanced stent apparatus 900. Enhanced stent apparatus 900 is provided with non-stretchable wires 902, and stretchable elastomer fibers 904, in accordance with an exemplary embodiment of the invention. Such an embodiment assists with the preservation of overall apparatus 900 length while allowing expandability and flexibility during implantation.

In an exemplary embodiment of the invention, an enhanced stent apparatus is provided which is comprised of at least an expandable support element and an expandable porous structure. The support element is optionally a stent, examples of which are known in the art for providing treatment to a wide range of body lumens. In an embodiment of the invention, the porous structure has structure which resembles to fishing net. In an embodiment of the invention, the porous structure is knitted from a fiber approximately 15-20 microns in diameter, has a coverage area of less than 20%, and which has aperture sizes approximately 150×200 microns. In some embodiments of the invention, the porous structure is at least temporarily attached to support struts of the support element by stitching. Optionally, the stitches are loose, allowing the porous structure to slide on the support struts, for example to provide extra expandability as described herein with respect to FIG. 16. In some embodiments of the invention, the stitching is biodegradable. In some embodiments of the invention, the support element and/or the porous structure are adapted to elute pharmaceutical agents into the body lumen being treated.

In some embodiments of the invention, different characteristics of the enhanced stem apparatus are chosen based on the intended use or treatment to be rendered. For example, aperture sizes are optionally chosen based on a desire to provide embolic shower protection against debris of a certain size. As another example, coverage area is optionally selected for modifying local pressure on the lumen being treated. Many of these characteristics are interrelated, as described herein and shown in FIG. 15, for example.

In an embodiment of the invention, porous structure 104 is flexible to allow the lumen to naturally change its diameter, to account for pressure changes in the lumen and/or to respond to muscular activity. In some embodiments of the invention, the porous structure 104 divided into a plurality of semi-independent sectors, which react differently to stimuli within or from the lumen. Optionally, the sectors are used to prevent banding of the lumen across the entire length of the porous structure 104.

Exemplary Characteristics and Performance of Porous Structure

Manufacturing techniques, described in more detail below, such as knitting which provide slack to individual fibers, or sections, of porous structure 104, enable porous structure 104 to optionally expand upon deployment up to 10 times its diameter at insertion (insertion diameter is described in more detail below), in an embodiment of the invention. For example, in coronary applications porous structure 104 may expand from 1 mm to 3 mm in diameter. In other examples, porous structure 104 may expand from 2 mm to 8 mm in carotid applications, while in brain applications porous structure 104 may expand from 0.3 mm to 2.5 mm. These numbers are approximate and are by way of example only. In an embodiment of the invention, expansion of porous structure 104 is effectuated in at least one of three ways: 1) the knitted/braided/woven structure of porous structure 104 (including slack in the fibers and curly fibers); 2) the fiber from which the porous structure 104 is made is at least slightly elastic; 3) sliding connections (described below) between porous structure 104 and support element 102 permit shifting of porous structure 104 during expansion with respect to support element 102, within certain limits. In an embodiment of the invention, the fiber from which porous structure 104 is made is comprised of between 2% and 80% of non-elastic materials. In some embodiments of the invention, the elastic material of the fiber from which porous structure 104 is made allows for expansion up to 1000% its original size.

Figure 12:
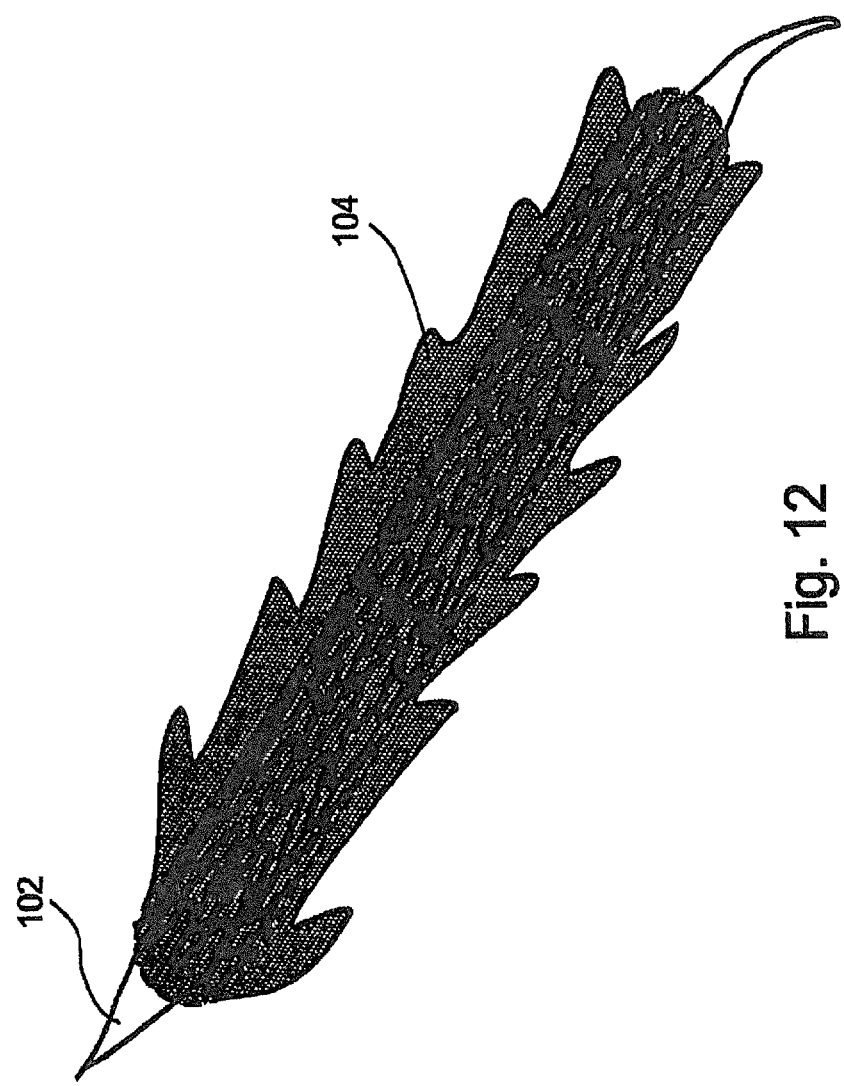
FIG. 12 is a perspective view of a porous structure significantly greater in diameter than an at least partially deflated balloon wherein the porous structure is folded on itself for insertion into a lumen, in accordance with an exemplary embodiment of the invention.

In some exemplary embodiments of the invention, porous structure 104 exhibits a high durability when subjected to twisting, turning, compression and/or elongation, which allows porous structure 104 to withstand the delivery process through the patient's vasculature to a treatment site. In an embodiment of the invention, porous structure 104 is loosely attached to the balloon at several locations and folded for insertion into a lumen, such as depicted in FIG. 12; such a configuration is optionally used in conjunction with supportive element 102. The folded porous structure 104 provides a reduced diameter apparatus for easier insertion into body lumens of the patient. As described below, porous structure 104 is at least temporarily fastened to balloon to prevent porous structure 104 from becoming dislodged during implantation.

In some exemplary embodiments of the invention, 20% of the total area of porous structure 104 is comprised of apertures having an approximate diameter no greater than 50, 200 or more than 200 microns in an expanded configuration. It is recognized that during the course of manufacturing the porous structure, for example with certain manufacturing techniques like electrospinning and/or knitting, apertures created within the porous structure may overlap. This overlap effectively creates an aperture size which is smaller than specified. However, in some exemplary embodiments of the invention, the effective, nominal aperture size is no greater than 50, 200 or more than 200 microns in diameter. In some embodiments of the invention, aperture sizes are selected to encourage endothelial cell overgrowth at a certain rate.

Figure 7:
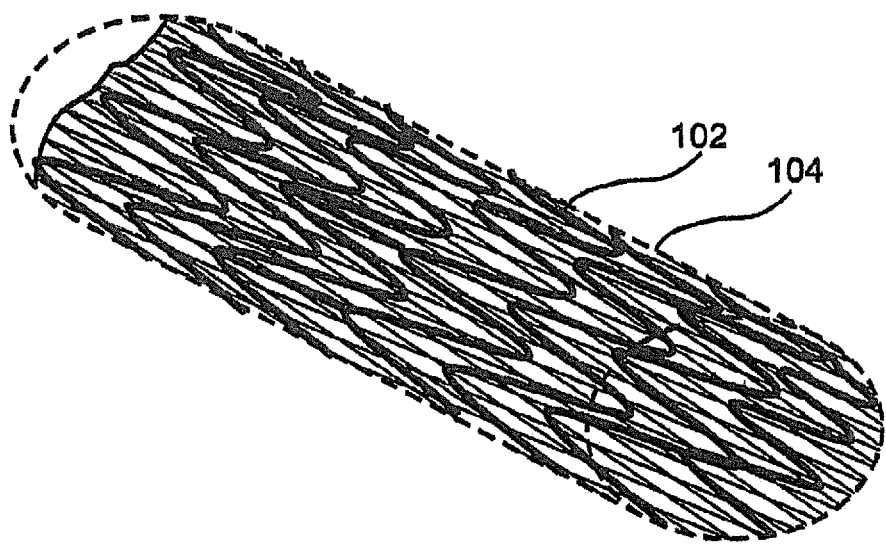
FIG. 7 is a perspective view of a braided porous structure enhanced stent apparatus, in accordance with an exemplary embodiment of the invention.

It should be noted that shapes of apertures are likely to vary at least somewhat as a result of manufacture and/or desired properties of porous structure 104. For example, in a knitted porous structure, apertures are most likely to be roughly square. In contrast, use of a weaving technique to manufacture porous structure likely produce square and/or rectangular shaped apertures whereas a braided porous structure is likely to exhibit quadrilateral shaped apertures, such as in FIG. 7. In describing an approximate "diameter" of an aperture, it should be recognized that all, some or none of the apertures will be actual circles, squares, rectangles and/or quadrilaterals capable of simplistic area measurement using diameter. Therefore, description using diameter is merely an approximation to convey exemplary aperture sizes. For example, "diameter" could be the distance between two parallel sides of a quadrilateral, such as a square or rectangle.

In some parts of the following description, aperture sizes described herein are in reference to their size upon porous structure deployment in a lumen. In other parts, the sizes refer to the aperture sizes when crimped. Sometimes, the aperture sizes described herein refer to their size in a state intermediate a crimped and deployed configuration. In context, it should be easily perceived which of the above configurations applies, however, in the event it is not clear the aperture sizes could be considered as applying to expanded, crimped or intermediate configurations. When a fiber diameter is referred to, it relates to the fiber used to construct the porous structure 104. For example, if porous structure 104 is constructed from a super-fiber comprised of a bundle of 10 fibers each 2 microns in diameter, the overall super-fiber diameter is about 20 microns. Furthermore, it should be understood that references to fiber diameter are for approximation and convenience only and does not imply that the fiber is necessarily round. Optionally, fiber sizes are measured in French sizes, for example 0.003 Fr.

Figure 15:
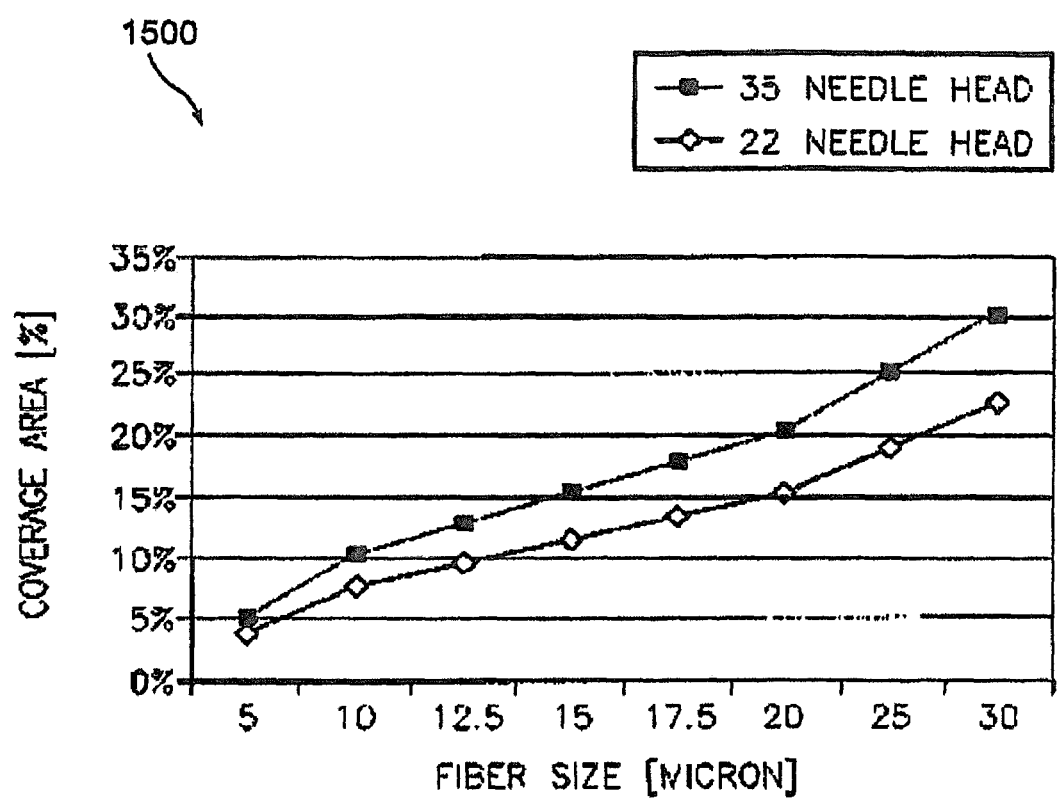
FIG. 15 is a graph showing fiber thickness vs. percentage of porous structure surface area that is structure, in accordance with an exemplary embodiment of the invention.

Referring to FIG. 15, a graph 1500 is shown which correlates fiber thickness of porous structure with percentage of the coverage area of a support element, for a porous structure with a fishing net type configuration. It can be seen that the general trend is that as the fiber sizes get thinner, the amount of porous structure surface area dedicated to structure is reduced. In an embodiment of the invention, it is desirable to have under 25% coverage area. Optionally, porous structure 104 exhibits less than 20% coverage area. In an embodiment of the invention, the coverage area of the porous structure is adapted to be minimized while still performing an intended lumen treating function, such as those described herein. In some embodiments of the invention, the coverage area of porous structure 104 is minimized in order to avoid undesirable clinical side effects. For example, lumen tissue irritation and pyrogenic effects are considerations for minimizing the coverage area and optionally other characteristics such as aperture size, porous structure thickness and/or fiber thickness, of porous structure 104.

Figure 22:
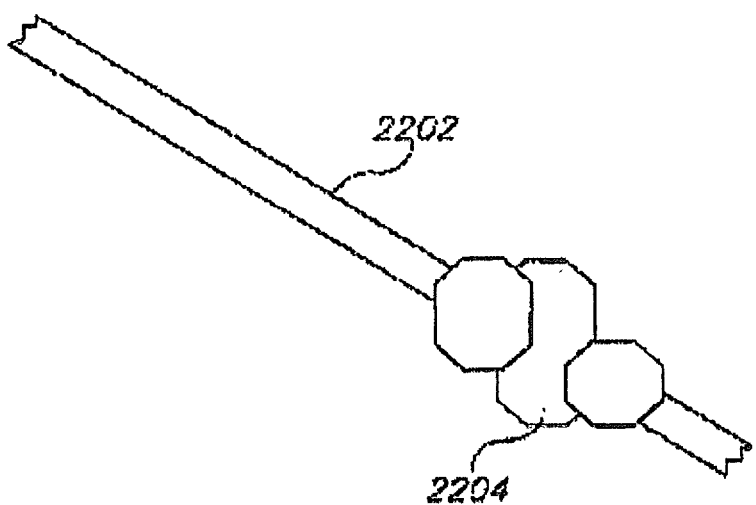
FIG. 22 is cross sectional view of a porous structure with an endothelium cell layer overgrowing it, in accordance with an exemplary embodiment of the invention.

In some exemplary embodiments of the invention, the proportion of structure to apertures of porous structure 104, fiber size and/or apertures are sized in order to allow easy diffusion through porous structure 104 and to facilitate growth of endothelial cells. Since the fiber 2202 diameters used in construction of porous structure 104 are on the order of the size of the endothelial cells 2204, or smaller, as shown in FIG. 22, the integrity of the cells grown over the porous structure will be much better than what is achieved in the prior art. An individual cell, statistically, will have a firm connection to the blood vessel wall, since it is of the same order or larger than the fiber diameter, thus anchoring itself, in an embodiment of the invention, in more than one location to its native basalamina intimal layer and enabling better growth conditions. It is thus expected that the chance of late or sub-acute thrombosis can be reduced over what is currently achieved when treatment is performed using a pharmaceutical eluting stent. In addition, porous structure 104 effectively acts as an embolic shower protection device, holding detached plaque in place, preventing it from traveling from the vessel wall into the blood stream. It should be noted that porous structure 104 is configured, accounting for fiber thickness, porous structure thickness and/or aperture size such that endothelial cells will overgrow porous structure 104, and optionally support element 102, in order to secure the enhanced stent in place and/or insulate the foreign material of support element 102 and/or porous structure 104 from the bloodstream. In an exemplary embodiment of the invention, endothelial cell layer overgrowth of porous structure 104 is established within hours of implantation. In an embodiment of the invention, overgrowth is accomplished within this time frame due to characteristics of porous structure 104 as they relate to endothelial cells, for example, the overall thickness being on the same order of or smaller, than an individual endothelial cell. In some embodiments of the invention, it is conceived that a patient's average stay in the hospital after a stenting procedure can be reduced as a result of the speed of endotheliazation using enhanced stent apparatus. In addition, the speed and efficacy of pharmaceutical treatment can expected to be enhanced as a result of the rapid endotheliazation over at least porous structure 104 of enhanced stent apparatus 100.

Figure 23:
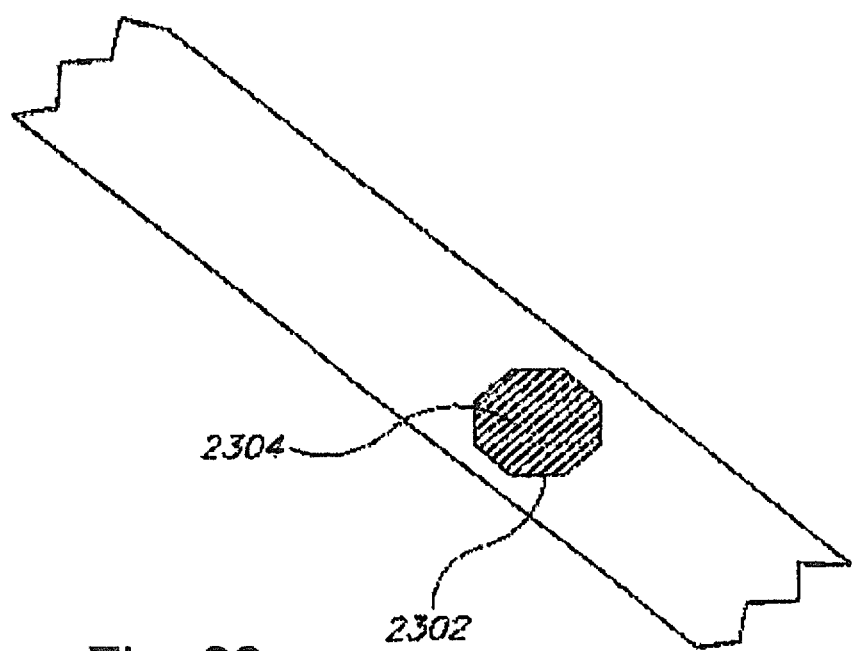
FIG. 23 is an illustration of a prior art situation in which a clump of endothelial cells detaches from a stent strut.

FIG. 23 shows a disadvantage of using prior art drug eluting stents wherein a clump of endothelium cells have become detached from the stent strut 2304, revealing an exposed "island" 2302 of the stent. Sometimes a clump falls off strut 2304 due to poor adhesion of the endothelium cells to the polymer coating of the strut 2304. Contributing to this poor adhesion, the stent strut 2304 is typically an order of magnitude larger than a single endothelium cell, thereby necessitating the creation of a large endothelium cell bridge to cross the strut. The exposed island 2302 can serve as a seed for thrombosis development. In some embodiments of the invention, porous structure 104 is constructed to reduce the likelihood of endothelial cells falling from the porous structure, thereby reducing the chance of development of late or sub-acute thrombosis and exposure of support element 102 to substances within the lumen. For example, endothelial cell retention is optionally encouraged by constructing porous structure 104 from at least one fiber of a thickness and with aperture sizes (to permit growth of endothelial cell therethrough), such as described herein. Optionally, endothelial cells are encouraged to remain on the porous structure by using a fiber layer of a thickness such as those described herein. Optionally, the linear nature of a single fiber porous structure 104, such as shown in FIG. 22, reduces the possibility of a large clump of endothelial cells becoming dislodged. In an embodiment of the invention, porous structure 104, optionally imbued with a pharmaceutical, is placed on the interior of a bare metal or drug eluting support element in order to reduce the thrombogenicity of the support element. For example, by encouraging endothelial cell growth thereover and/or by reducing the exposed surface area of the support element by covering a portion of it up.

As suggested above, using a thin fiber whose thickness is similar to, or smaller than, the diameter of an endothelial cell enables an endothelial cell layer to grow over porous structure 104 while still being closely tied to the basal intima layer at least at two points of the endothelial cell, one point on each side of porous structure 104. In an embodiment of the invention, the anchoring effect of this basal intima layer on the endothelial cell layer reduces the chance of parts of the endothelial cell layer breaking off and entering the lumen. This, in effect, reduces the chances of embolism in the patient and/or also reduces the likelihood of foreign bodies (e.g. the stent and the porous structure) coming into contact and reacting with the contents of the lumen being treated. In the event that a clump of several endothelium cells fall from porous structure 104, exposing a piece of the fiber, it is believed that there is a reduced chance of harm to the patient since the linear, single endothelial cell width geometry is not as thrombogenic as that shown in FIG. 23, where a clump of endothelial cells at least several cells in diameter has fallen off. In addition, the re-endotheliazation will be faster on an exposed porous structure 104 than on the exposed strut 2304 for at least the reason that in the case of the porous structure 104, an endothelial cell layer is formed when just one endothelial cell overgrows the endothelial cell sized fiber used to construct the porous structure. In contrast, endothelial cell layer overgrowth is only accomplished after multiple endothelial cells have covered the exposed island.

In an embodiment of the invention, the reduced risk of late or sub-acute thrombosis by using porous structure 104 for pharmaceutical elution optionally allows for a duration and/or dosage reduction in the use of anti-coagulants by the patient.

In some exemplary embodiments of the invention, fiber thickness, porous structure thickness and/or aperture size are all separately varied depending on the application of porous structure 104 and the needs of the patient. For example, in the coronary arteries it is sometimes helpful to provide for good pharmaceutical dispersion. In such an example, fibers comprising porous structure 104 are optionally located closer together in order to allow for more complete transmission of a pharmaceutical to patient.

In some exemplary embodiments, when large molecule drugs, which have a poor diffusion into the tissue, are used to fight restenosis, the porous structure can be soaked and/or imbued with an appropriate drug in order to better diffuse it. The maximum concentrations of most of the drugs used are rather limited due to side effects and over toxicity, and at the same time the concentration is not enough in order to allow the optimum pharmacokinetics in areas not covered by the stent struts. The porous structure mesh, having a better geometrical cover of the stent area, provides a better and more optimum pharmacokinetics to the whole area covered by the stent. For example, when high Dalton-large molecule drugs are used, or when liposomes are the carriers of the treatment agents, or when the stereo-chemical structure of the drug is large and/or complicated, and/or when the drug is hydrophobic, relatively even distribution of the drug is highly desirable. In some exemplary embodiments of the invention, pharmacokinetics are also optimized because the drug is located on/in the fibers of porous structure 104, and is covered and sealed within an endothelium layer, which helps the drug from being washed away by the blood.

In some exemplary embodiments of the invention, such as in a bypass vein graft, side branching is not an issue, therefore aperture sizes are optionally made smaller, but not so small as to prevent endothelial cell growth therethrough. In another exemplary embodiment of the invention, such as in the carotid arteries, side branching is not generally considered a problem, but catching debris is. Therefore, in some exemplary embodiments of the invention, the aperture sizes of porous structure 104 are decreased to as little as 20 microns in diameter. In other applications, the aperture size can be increased to 50, 100, 200 or even more then 200 microns, depending on the application of enhanced stent apparatus 100.

In some exemplary embodiments of the invention, a plurality of porous structures is used. Optionally, at least one porous structure is located on the interior of support element 102, inside the lumen of support element 102. Optionally, more than one porous structure is located on the exterior surface of support element 102. In some exemplary embodiments of the invention, at least some of the porous structures located on support element 102 are configured to be "in-phase" where the apertures of the porous structures coincide with one another. Optionally, the porous structures are "out-of-phase" where the apertures are configured to not coincide with one another. In an exemplary embodiment of the invention, an "out-of-phase" configuration is used to improve contact surface area between porous structures and the lumen interior surface. In an embodiment of the invention, increased contact surface area can improve pharmacokinetics, reduce local pressure exerted by porous structure 104 on the lumen wall, improve embolic shower protection and/or realize other advantageous effects. In some exemplary embodiments of the invention, porous structure 104 is constructed in the same shape and pattern as support element 102, but on a smaller scale.

Exemplary Materials of Manufacture

It should be noted that in some exemplary embodiments of the invention, a stretchable and/or expandable porous structure 104 is desired. Therefore, in some embodiments of the invention, materials are chosen which are either a) stretchable and/or b) can be used to manufacture a porous structure which is stretchable (e.g. a knitted structure). In some exemplary embodiments of the invention, biodegradable (i.e. are broken down by the body) and/or bioresorbable (i.e. are absorbed into the body) materials are used. In addition, blends of materials are used in accordance with some embodiments of the invention. In an embodiment of the invention, a material is chosen because it exhibits durability during manufacture, deployment and/or use despite being thin. In an embodiment of the invention, other considerations for the material to be used are their biocompatibility, toxicity, hemocompatibility, and thrombogenicity.

Exemplary materials for manufacturing porous structure 104 include natural-based materials such as modified cellulose and/or collagen. In some embodiments of the invention, metal fibers are used to construct porous structure, optionally constructed of stainless steel, and/or CoCr and/or CoNi alloy among other possibilities. Optionally, the metal fibers used are coated with at least one polymer. In some embodiments of the invention, porous structure is manufactured from a shape memory alloy, such as nitinol. Optionally, carbon fiber is added to porous structure 104 in order to improve strength characteristics of porous structure 104. Optionally, glass fiber is added to porous structure 104 in order to improve strength characteristics of porous structure 104. Optionally, a durable, resorbable and/or degradable fiber is added to porous structure 104 in order to improve strength and durability characteristics of the fiber during manufacture, which is degraded or resorbed or washed away to leave a thinner porous structure 104.

In an embodiment of the invention, some polymer fibers are chosen for use in constructing porous structure 104 because they are elastic, biocompatible, hemocompatible, can be made not to stick to an expandable angioplasty-type balloon catheter, to stick to endothelium tissue, are selectably bio-stable and/or biodegradable, exhibit the requisite mechanical strength, are sterilizable, have a high temperature transformation zone (solid and non-sticky at 37° C.), are capable of hosting an effective amount of pharmaceuticals, and/or can release embedded pharmaceuticals at a controlled rate. In some exemplary embodiments of the invention, other materials which exhibit some or all of these properties are optionally used to construct porous structure 104. Optionally, coatings are put on porous structure 104, comprised of materials which exhibit some or all of these properties.

Polymer fibers are optionally made out of any of the following materials: thermoplastic polymers for example polyethylene terephthalate (PET), polyolefin, oxidized acrylic, PTFE, polyethylene co-vinyl acetate, polyethylene elastomer, PEO-PBT, PEO-PLA, PBMA, polyurethane, Carbosil (PTG product), medical grade polycarbonate urethanes, Nylon, PEEK-Optima, carboxylic acid moiety comprising one or more of a poly acrylic acid, a poly methacrylic acid, a maleic acid, a helonic acid, a taconic acid and/or combinations and/or esters of these monomers, thermoplastic polymers, thermosetic polymers, polyolefin elastomers, polyesters, polyurethanes, polyfluoropolymers, and/or nylon. Optionally, the fibers are constructed of an elastomer. Optionally, the fibers are constructed of a coated fiber with a drug and polymer coating mixed to get a predetermined drug release characteristic, either coating over a metal and/or over a polymer fiber. Optionally, the fibers are constructed of other materials than the exemplary materials listed above. Exemplary polymers which are optionally used for this purpose are manufactured by Cordis®, Surmodix®, Boston Scientific®, Abbott® and Hemoteq® Polymers. Optionally, these polymers are selected for at least one of the reasons specified in the paragraph above. Optionally, the coating is used to facilitate the elution of pharmaceuticals from porous structure 104.

In some embodiments of the invention, the porous structure is made out of a resorbable/degradable polymer such as poly lactic-co-polyglycolic ("PLGA") copolymers, or any other degradable copolymeric combination, such as polycaprolactone ("PCL"), polygluconate, polylactic acid-polyethylene oxide copolymers, poly(hydroxybutyrate), polyanhydride, poly-phosphoester, poly(amino acids), poly-L-lactide, poly-D-lactide, polyglycolide, poly(alpha-hydroxy acid) and combinations thereof.

In some embodiments of the invention, porous structure 104 is comprised of a material which plastically or elastically deforms when a sufficient amount of radial pressure is applied to it, for example by an angioplasty balloon.

Exemplary Methods of Manufacture

Many of the methods and orientations described herein are designed to provide a porous structure which exhibits at least some expandable quality. Porous structure 104 is optionally adapted and constructed to stretch as it is being deployed within the lumen being treated. In some exemplary embodiments of the invention, porous structure 104 is provided with stretchability in order to ease positioning porous structure 104 on a balloon and/or support element 102.

In an exemplary embodiment of the invention, weaving, braiding and/or knitting results in some or all the elasticity of the porous structure being achieved due to the structure of the interlaced and/or crimped and/or textured fibers (curly, slack). This can be achieved by material elongation properties securing the porous structure to the stent. In some exemplary embodiments of the invention, a porous structure is made by combining several interlacing techniques such as knitting over a braided porous structure or braiding over a knitted porous structure. In some embodiments of the invention, multiple layers are combined and/or created using these techniques. In some exemplary embodiments of the invention, a warp knitted porous structure with "laid in" yarns is used. In some exemplary embodiments of the invention, a porous structure is woven using elastomeric or crimped weft to obtain radial elasticity.

In some exemplary embodiments of the invention, the porous structure is manufactured by combining several techniques such as knitting over a braided porous structure or braiding over a knitted porous structure. In some exemplary embodiments of the invention, a weft knitted porous structure with "laid in" yarns is used. In some exemplary embodiments of the invention, a porous structure is woven using elastomeric and/or crimped weft to obtain radial elasticity. Optionally, porous structure is comprised of at least one fiber oriented generally parallel to the support element's longitudinal axis.

In an exemplary embodiment of the invention, a manufactured porous structure is added as a cover to support element 102. Optionally, porous structure 104 is used separately from support element 102, which is optionally not used for stenting. In some exemplary embodiments of the invention, porous structure 104 is manufactured directly onto support element 102.

In an exemplary embodiment of the invention, porous structure 104 is manufactured by a knitting technique known to those of ordinary skill in the knitting art for non-analogous arts, such as clothing manufacturing and textiles. Knitting of porous structure 104 is optionally performed by heads having between 20 and 35 needles. Optionally, the head used has between 30 and 45 needles. Optionally, the head used has between 35 and 80 needles. An example of the effect of head size on the porous structure can be seen in FIG. 15, described above, in which a 22 size head and a 35 size head are graphed. In FIG. 15, the needle gauges are 40.

In some embodiments of the invention, the shape and/or size of the knit is controlled by controlling the tension on the fiber being used for knitting. For example to create a knit with larger eyes, slack is provided to the fiber during knitting. Optionally, the fiber is controlled during knitting to achieve a circular shaped eye when porous structure 104 is expanded. In an embodiment of the invention, pre-tension on the fiber during knitting is approximately 10-20 grams. In some embodiments of the invention, post-tension on the fiber during knitting is 15-25 grams. The stitch length is between 300 and 400 microns, in an exemplary embodiment of the invention. In some embodiments of the invention, the knitting machine is run at a relatively slow speed. For example, the knitting machine is run at 10% of speed capacity using a Lamb Knitting Machine Corp. System Model WK6 with a special modification of speed operation measured by percentage.

In an exemplary embodiment of the invention, a fiber or a super-fiber yarn with a specific fineness, or a range of fineness, between 5 and 100 microns is used to manufacture a knit porous structure. Optionally, yarn with a fineness of 10 to 20 microns is used to manufacture a knit porous structure. Optionally, the yarn is finer than 5 microns. Yarn fineness is often referred to in textile terms by "Tex". This is the weight in grams of 1000 meters of the yarn. In an exemplary embodiment of the invention, yarn ranging from 0.3 Tex to 10 Tex is used to manufacture porous structure. In some embodiments of the invention, a specific yarn fineness is chosen based on the desired porous structure 104 characteristics. For example, a 0.5 Tex yarn using a 22 gauge needle head will, in some embodiments, produce a porous structure with approximately 12% coverage area.

Figure 5:
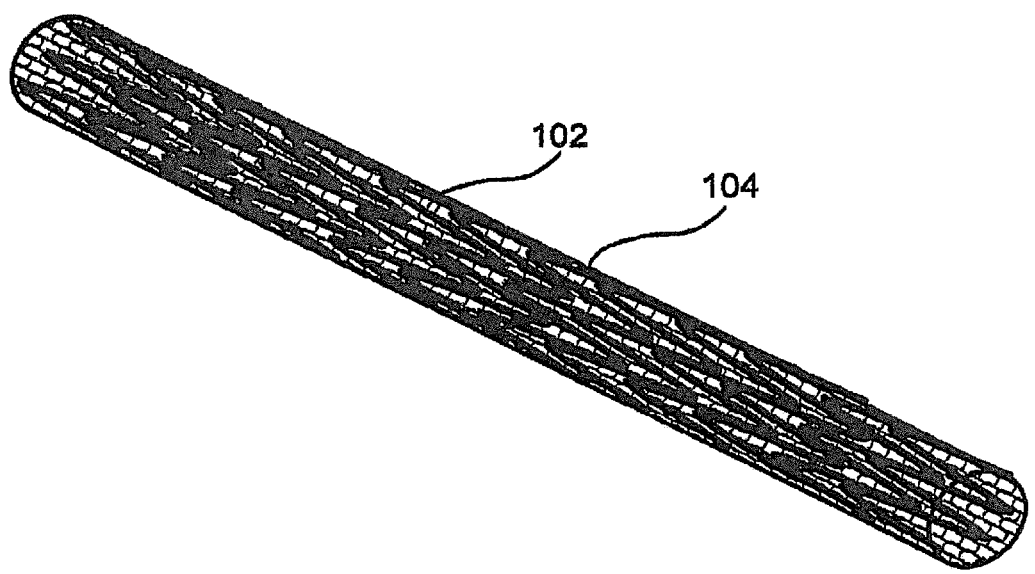
FIG. 5 is a perspective view of an enhanced stent apparatus, in a crimped, closed mode, in accordance with an exemplary embodiment of the invention.
Figure 6B:
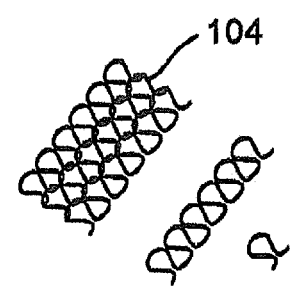
FIG. 6B is a detailed view of a knitted porous structure, in accordance with an exemplary embodiment of the invention.
Figure 6A:
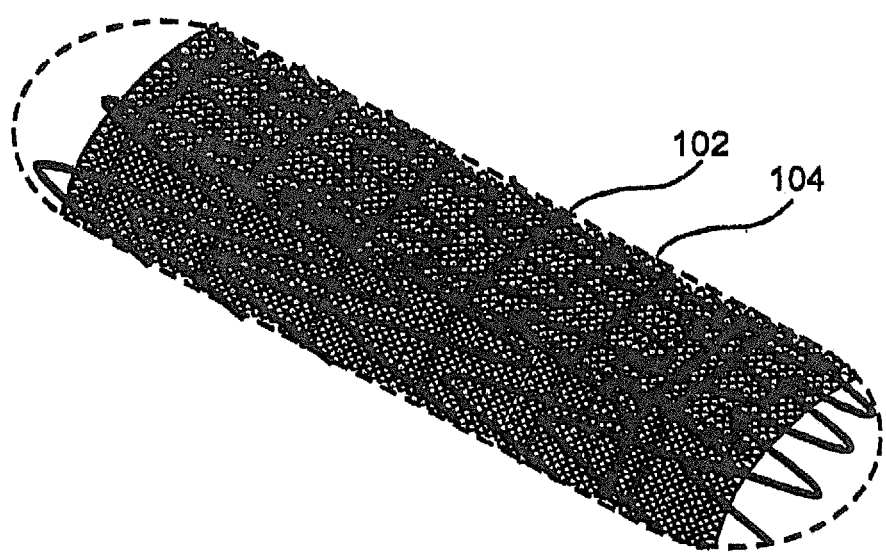
FIG. 6A is a perspective view of a knitted porous structure enhanced stent apparatus in an open mode, in accordance with an exemplary embodiment of the invention.

An exemplary resulting porous structure using the above components and techniques, should have 5 to 50 courses per cm. Optionally, 20 to 45 courses per cm are manufactured. Optionally, a porous structure with 30-35 courses per cm is manufactured. FIG. 5 illustrates a knitted porous structure 104 and support element 102 in a crimped, closed position. FIG. 6A illustrates a knitted porous structure 104 laid on top of a support element 102 in an open position. FIG. 6B shows exemplary knitting in detail.

In another exemplary embodiment of the invention, weaving techniques are used to manufacture porous structure 104. Narrow needle looms as well as conventional narrow looms can be configured to produce woven tubular structures. In weaving, at least two layers of warp yarns are interlaced with intersecting fill yarns.

By carrying the fill yarn alternately back and forth across two layers of warp yarns, a tubular shape is created. The size and shape of the weave are optionally controlled by determining the warp and/or fill density, the interlacing pattern and/or frequency, the yarn tension and/or the yarn dimensions and/or elastic properties. The types of weaves used for a porous structure are optionally any one of "plain", "basket", "twill", "sateen", "leno" and/or "jacquard". Optionally, all of the fibers of porous structure are the same. Alternatively, warp and weft fibers of a weave are not constructed of the same materials. Optionally, different materials are used to take advantage of the inherent properties of the different materials, for example one material may be elastic and a different material may have a high tensile strength. Optionally, warp fibers are coated and/or are pharmaceutical eluting while the weft fibers are not, or vice versa.

In another exemplary embodiment of the invention, braiding techniques are used to manufacture porous structure 104, for example as described in Knitting Technology, D. J. Spencer-ed., Woodhead Publishing Limited, Abington Hall, Abington, Cambridge, CB1 6AH, England, the disclosure of which is incorporated herein by express reference thereto. Braiding machines are optionally used to interlace yarns at a variety of intersecting angles. In braiding, multiple yarns are fed to an interlacing zone. Interlacing is optionally achieved by rotation of the yarn spools or by a reciprocating needle bed. The size and shape of the braid is optionally controlled by the number of yarns, the interlacing pattern and/or angle and/or the yarn dimensions and/or elastic properties. Optionally, all of the fibers of porous structure are the same. Optionally, warp and weft fibers of a braid are not constructed of the same materials, for example where weft fibers are used to provide strength and warp fibers are used to provide stretchability of the braid.

Figure 4:
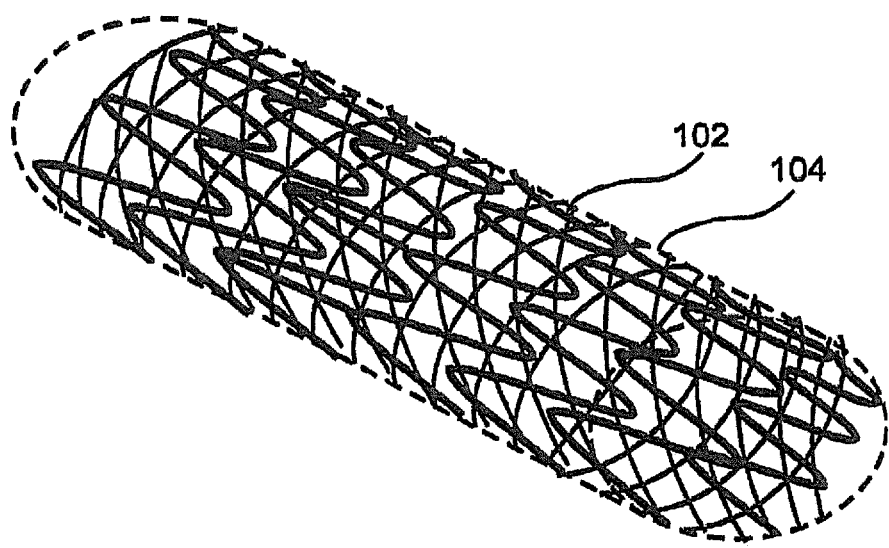
FIG. 4 is a perspective view of an enhanced stent apparatus, with multiple helical coils in an open mode, in accordance with an exemplary embodiment of the invention.

In another exemplary embodiment of the invention, porous structure 104 is manufactured by an electrospinning process. Electrospinning is a technique which utilizes a charged polymer solution (or melt) that is fed through a small opening or nozzle (usually a needle or pipette tip). Because of its charge, the solution is drawn toward a grounded collecting plate (usually a metal screen, plate, or rotating mandrel), typically 5-30 cm away, as a jet. Optionally, support element 102 is placed on a delivery catheter which is used as a mandrel. During the jet's travel, the solvent gradually evaporates, and a charged polymer fiber is left to accumulate on the grounded target. The charge on the fibers eventually dissipates into the surrounding environment. The resulting product is a non-woven fiber porous structure that is composed of tiny fibers with diameters between approximately 40 nanometers and 40 microns (e.g. a felt), depending on the size of the fibers input into the system. If the target is allowed to move with respect to the nozzle position, such as by rotating and/or moving the mandrel along its longer axis, specific fiber orientations (parallel alignment or a random alignment, as examples) can be achieved. In some exemplary embodiments of the invention, porous structure 104 is spun in a helical coil pattern onto the mandrel or support element 102. Optionally, porous structure 104 is comprised of a plurality of helical coil patterns, constructed by moving the mandrel back and forth, such as depicted in FIG. 4. Optionally, porous structure 104 is constructed with fibers oriented substantially parallel to central axis 106. Optionally, porous structure 104 is constructed with fibers oriented substantially perpendicular to central axis 106. Optionally, porous structure 104 is constructed with fibers oriented in a combination of any of the orientations described or suggested herein. The mechanical properties of the porous structure are optionally altered by varying the fiber diameter and orientation depending on the requirements for treating a patient. For example, in some embodiments of the invention, a laser is used to cut specific aperture sizes and/or to ensure that the apertures traverse from the exterior side of porous structure 104 to the interior side of porous structure 104. Optionally, solvent is used to modify aperture sizes.

Optionally, portions of catheter are masked in order to prevent accidental coverage of the delivery catheter by porous structure 104. Optionally, support element 102 is coated with an adhesive and/or a pharmaceutical agent prior to putting the porous structure 104 on the top of support element 102. In some exemplary embodiments of the invention, the material used to produce the porous structure 104 is imbued with pharmaceutical agents. Optionally, pharmaceutical agents are embedded in the material coating the porous structure 104. In an exemplary embodiment of the invention, porous structure 104 is comprised of at least one inner coating proximal to supporting structure 102 which exhibits different properties than an external coating proximal to patient's blood vessel. For example, the inner coating is optionally configured to avoid adhesion to the delivery catheter and/or support structure. Optionally, inner coating is configured to adhere to support element 102, but not to delivery catheter.

In some embodiments of the invention, porous structure 104 is designed to be less sensitive to foreshortening and elongation forces as porous structure 104 expands upon deployment. This is in part due to the knitted nature of porous structure 104, in some embodiments. This property allows porous structure 104 to be secured to support element 102 at its ends, rather than in another location, such as the middle as described in U.S. App. No. 2005/0038503 to Greenhalgh et al., the description of which is incorporated herein by express reference thereto.

In some exemplary embodiments of the invention, a porous structure is manufactured in an at least partially open, wide diameter, condition. In some exemplary embodiments of the invention, the at least partially stretched porous structure is reduced to a smaller diameter, by heat-setting, crimping and/or folding, after manufacture.

Figure 13:
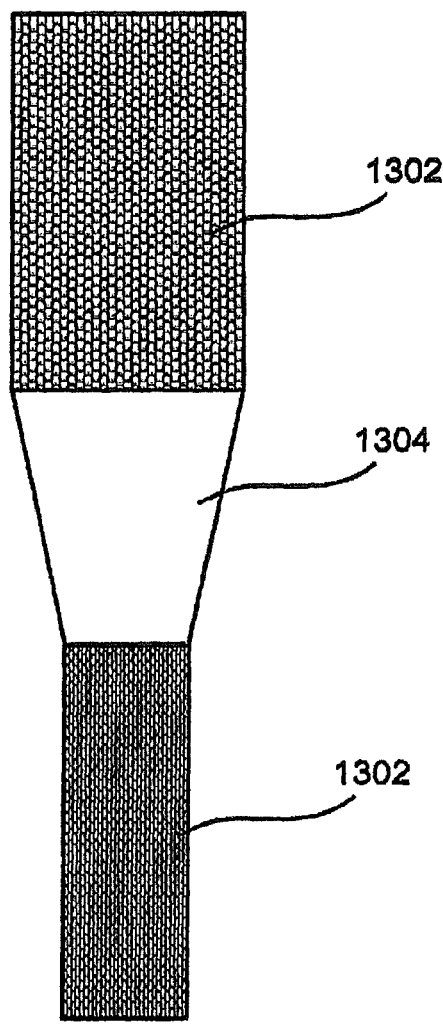
FIG. 13 illustrates the use of a funnel to reduce the diameter of at least a porous structure, in accordance with an exemplary embodiment of the invention.
Figure 14:
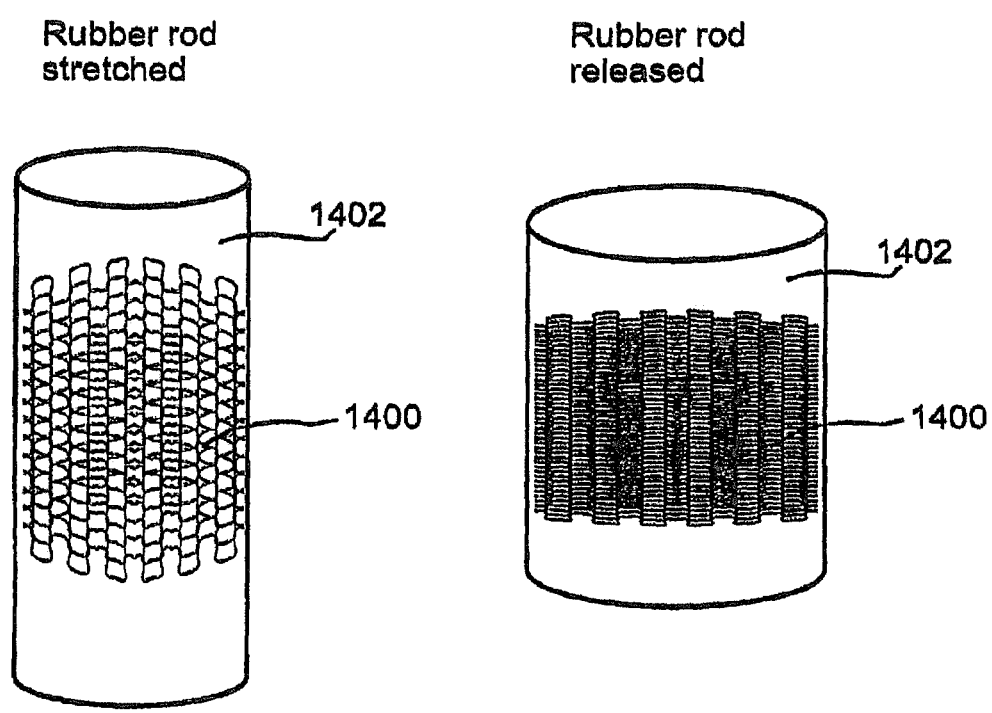
FIG. 14 illustrates using a stretchable rubber tube for manufacturing a compressed porous structure, in accordance with an exemplary embodiment of the invention.

In an embodiment of the invention, the diameter of the at least partially stretched porous structure is reduced mechanically. Optionally, a funnel 1304 shown in FIG. 13, is used to reduce the diameter of the knitted porous structure 1302, during the manufacture the porous structure. A knitted porous structure 1302 is drawn down from the knitting zone into a narrowing bore, funnel 1304. This results in a final porous structure diameter that is controllably smaller than the diameter of the needle bed. FIG. 14, illustrates how a porous structure is manufactured using a stretched rubber tube 1402. In this method, the porous structure 1400 is tightly inserted onto a pre-radially stretched tube 1402, and then the tube is relaxed, compressing the porous structure and creating a smaller aperture sized porous structure, the size of which is controlled by the stretch ratio of the rubber tube.

Figure 11:
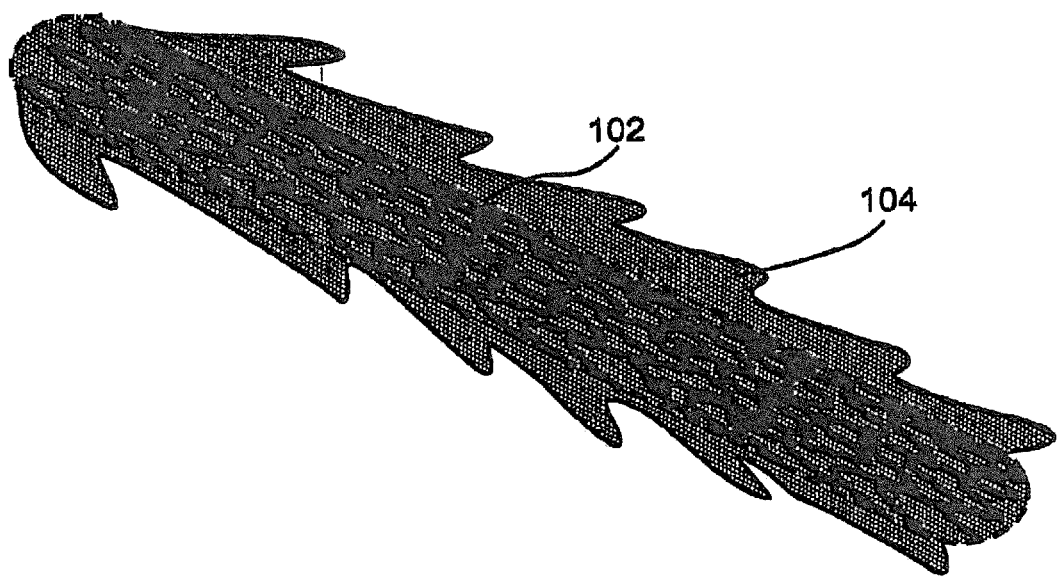
FIG. 11 is a perspective view of an enhanced stent apparatus, wherein porous structure is significantly greater in diameter than a crimped support element, and is folded on itself for insertion into a lumen, in accordance with an exemplary to embodiment of the invention.
Figure 18:
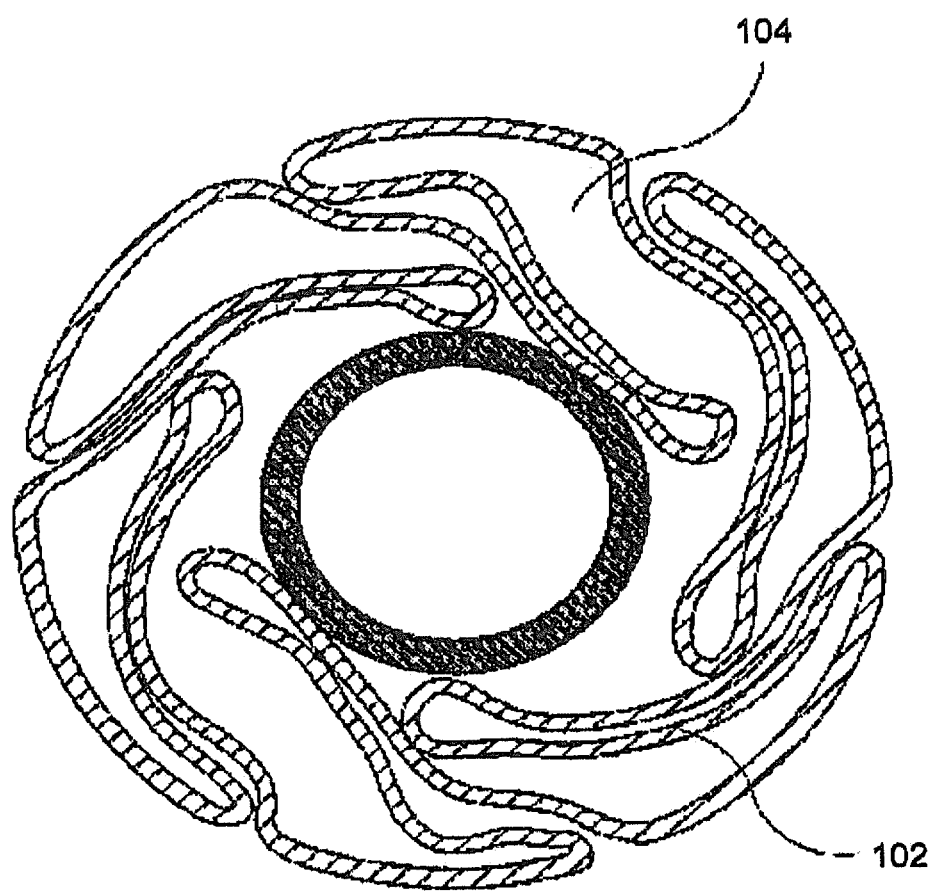
FIG. 18 is a cross-section view of an enhanced stent apparatus showing a porous structure folding technique, in accordance with an exemplary embodiment of the invention.

Referring to FIG. 18, an embodiment is shown in which porous structure 104 is folded in "n" substantially folds, the folds used to reduce the overall diameter of enhanced stent apparatus 100 for easier insertion and navigation through the patient. Optionally, the folds are towards the same direction. In an embodiment of the invention, a folded porous structure 104 is at least temporarily secured to support element 102. FIG. 11 shows an alternate folded configuration from a perspective view.

An additional or alternative embodiment to folding includes heat setting a polymer comprised porous structure 104 to support structure 102. In an embodiment of the invention, heat setting is used when porous structure 104 is comprised of at least one polymer material. Determination of heat setting conditions is related to the polymer's heat transition temperatures, in an embodiment of the invention. Heat setting is performed in the temperature range between $T_g$ and $T_m$ of the polymer. At this range the polymer becomes amorphous and is shrunk to support element 102, establishing an overall enhanced stent apparatus 100 radius that is not much more than the support element 102 radius. For example, porous structure 104 adds less than 10 microns in diameter total to support element 102 which is 1 mm in diameter, in some embodiments of the invention. At $T_m$ the polymer turns into a viscous liquid which loses its mechanical integrity and will stick to support element 102 surface. For example, polyethyleneterephthalate (PET) has a $T_g$ of 70° C. and a $T_m$ of 265° C., therefore the heat set temperature somewhere within that range, in an embodiment of the invention, is 200° C. Using temperatures higher than $T_m$ for heat setting can cause thermal degradation, which results in polymeric chain scission, unzipping of the polymer and/or producing a large array of oligomeric material that changes the mechanical properties of porous structure 104 and/or releases poisonous and/or non-biocompatible materials, causing an inflammatory reaction in the patient. Other exemplary polymers which can be used in heat setting are below in Table 1 (not an exhaustive list):

TABLE 1

Exemplary polymers and temperatures for heat setting

| Material name | $T_g$ | $T_m$ | set temp. |
| --- | --- | --- | --- |
| PP | 18° C. | 165° C. | 140° C. |
| NYLON 6,6 | 80° C. | 256° C. | 210° C. |
| PTFE | 150° C. | 330° C. | 300° C. |
| PVA | 100° C. | 230° C. | 190° C. |
| Polyurethanes | 70° C. | 120° C. | 100° C. |
| PLLA | 60° C. | 175° C. | 100° C. |

Another additional or alternative embodiment to folding includes crimping using at least a crimped support element 102 in combination with porous structure 104. In some embodiments of the invention, porous structure 104 is crimped with support element 102. In an embodiment of the invention, crimping of porous structure 104 and support element 102 is performed when it is desirable to reduce the overall diameter of enhanced stent apparatus 100. For example, a reduced diameter enhanced stent apparatus 100 allows for easier insertion and navigation of the apparatus to the treatment site. In some embodiments of the invention, at least a crimped support element 102 provides an object with relatively stable mechanical properties for more predictable movement during insertion and navigation.

Optionally, porous structure 104 is made on a non-crimped support element 102. A non-crimped support element 102 can be expanded or semi-expanded during manufacture. In an exemplary embodiment of the invention, porous structure 104 and support element 102 are crimped together. Optionally, excess porous structure 104 material, which is created as a result of reducing the profile of support element 102 during crimping, is folded with support element 102, such as shown in FIG. 18. In some exemplary embodiments of the invention, porous structure 104 is made on a crimped or partially crimped support structure 102. When manufacturing a porous structure for placement on an already crimped support structure, consideration may be given to providing a porous structure which is sufficiently stretchable to expand with the radial expansion of the support structure, when implanted at a treatment site within a lumen. In some embodiments of the invention, a porous structure is placed on a support element already positioned on an angioplasty balloon.

In electrospinning embodiments of the invention, the procedure for manufacturing a porous structure on a balloon is similar to manufacturing on a stent or mandrel. For example, varying the motion of the balloon with respect to the electrospinning device allows the manufacture of specific fiber orientations.

Exemplary Methods for Coating a Fiber

Figure 19:
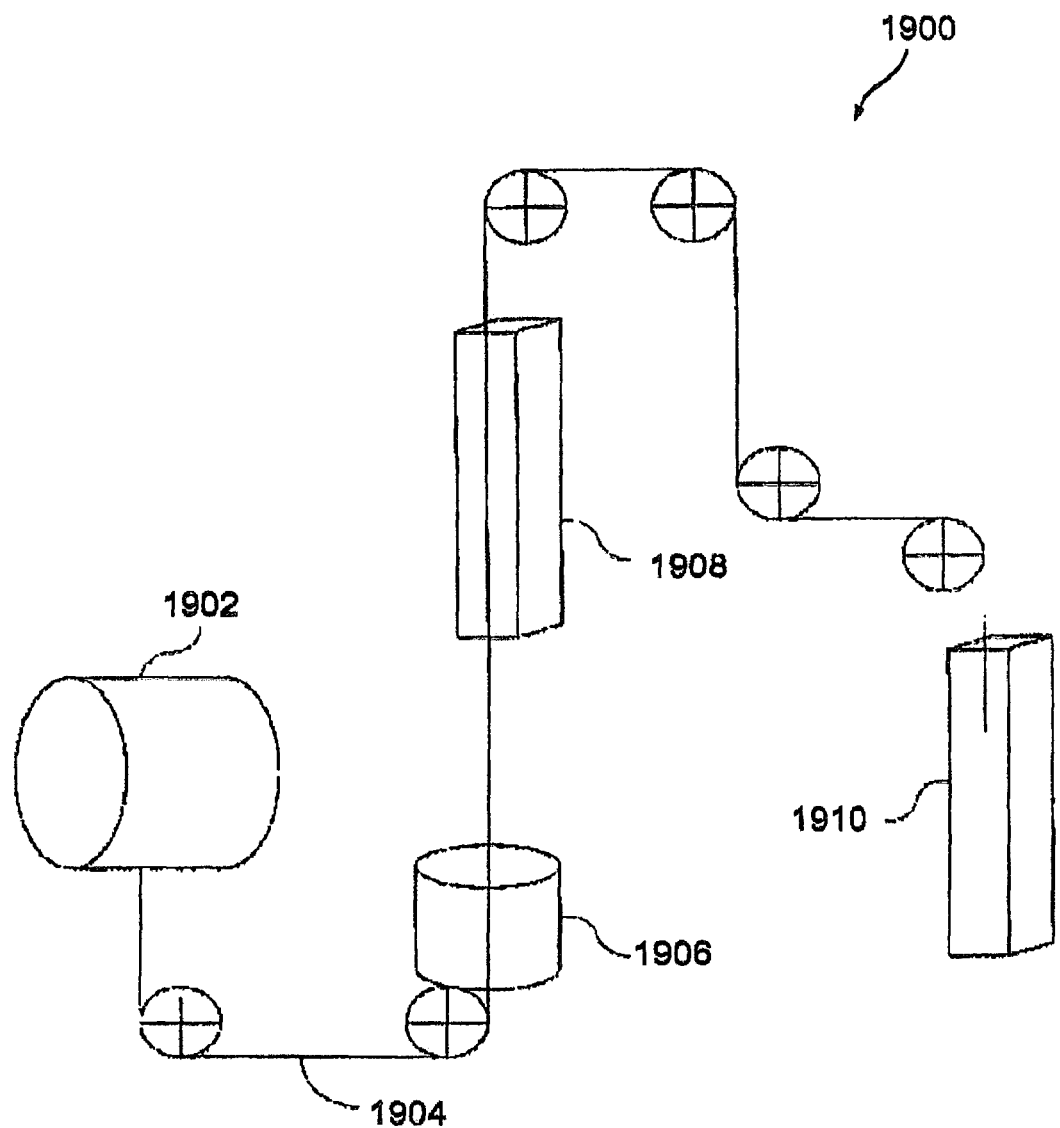
FIG. 19 is a schematic showing a method for manufacturing a porous structure, in accordance with an exemplary embodiment of the invention.

In another exemplary embodiment of the invention, a manufacturing technique is used to coat a fiber that porous structure 104 is comprised of with at least one polymer layer. For example, a dipping technique, shown in FIG. 19, using a biocompatible, hemocompatible, biostable and/or biodegradable polymer dissolved in an organic solvent is utilized to create a dipping solution 1906 for use in coating the fiber comprising porous structure 104. The fiber to be coated is optionally placed in a spool 1902, from which the fiber 1904 is drawn to form porous structure 104. Additives such as drugs, biological components, enzymes, growth factors, and/or any other additive mentioned herein or known in the art, may be incorporated into fiber 1904 during the manufacturing process, for example by placing them in solution 1906 and passing fiber 1904 through solution 1906. In an embodiment of the invention, at least one layer is used in order to control the drug/biological additive's release. For example, more than one solution tank may be provided for fiber 1904 to pass through during manufacture. Fiber 1904 is optionally moved into a drying oven 1908 with an operational temperature range from 37-70° C. (in some embodiments of the invention) depending on the drug used, to dry solution 1906 onto fiber 1904. In an exemplary embodiment of the invention, fiber 1904 is then used by a knitting system to 1910 to manufacture porous structure 104. Optionally, knitting system 1910 is the Lamb Knitting Machine Corp. System Model WK6. Optionally, porous structure 104 is coated with a polymer layer after it has been manufactured.

In some exemplary embodiments of the invention, support element 102 and porous structure 104 are coated with an additional substance. Optionally, the additional substance is a polymer. Optionally, the additional substance is drug eluting. Optionally, the coating is hyaluronic acid. Alternatively or additionally, the coating is hyaluronan. Optionally, a different non-woven technology such as wet and/or dry spinning is used to manufacture porous structure 104. In some embodiments of the invention, additional coatings are added to achieve different effects, for example timed release of pharmaceutical agents and/or release of a plurality of agents at different times.

Exemplary Methods for Mounting Porous Structure to Support Element

In some embodiments of the invention, porous structure 104 is at least temporarily secured to support element 102. Advantages of securing porous structure 104 to support element 102, at least temporarily, include: prevention of unraveling and/or run out of fiber from the porous structure weave, dislodgement and/or slipping of porous structure 104 with respect to support element 102 during insertion, delivery and/or deployment. Optionally, support element 102 and porous structure 104 are not secured together using an adhesive and/or other securing means despite being in a coaxial and proximate relationship in many embodiments.

In some exemplary embodiments of the invention, where support element 102 is optionally coated with a polymer, support element 102 and porous structure 104 are attached together by curing at the same time the polymer support element coating and the polymer comprised porous structure, and/or coated porous structure, thus adhering the polymers together. Optionally, pressure and/or heat is used to adhere a polymer coated support element 102 to a non-coated or polymer coated porous structure 104, for example when they are both hot. In some exemplary embodiments of the invention, porous structure 104 is comprised of two components, an external component and an internal component, relative to support element 102. Upon the simultaneous curing of the external and internal components, the polymers of which both are comprised to adhere together, thereby securing porous structure 104 to support element 102, which is located between the components.

In an exemplary embodiment of the invention, porous structure 104 is secured to support element 102 in order to avoid porous structure migration, but not limit porous structure 104 and/or support element 102 expandability.

In some exemplary embodiments of the invention, an adhesive is used to bond support element 102 and porous structure 104 together. Optionally, porous structure 104 is glued to support element 102 utilizing any natural and/or synthetic biocompatible adhesive, such as cyanocrylate, thermo plastic elastomers, silanes, laminin, albumin and/or fibrinogen and/or PEG-PEG adhesive, and/or polyurethane adhesive and/or any other suitable compatible polymeric material. Optionally, when porous structure 104 is glued to support element 102, wherein the support element 102 is a drug eluting stent, the same polymer as used for the elution of the drug is used for attachment of porous structure 104 to support element 102.

In an embodiment of the invention, porous structure 104 is attached to support element 102 at a plurality of points. Optionally, the plurality of points defines a pattern, such as a line or zigzag of points. Optionally, porous structure 104 compresses onto support element 102 to maintain an attachment to support element 102. Optionally, the porous structure is held in place on support element at least partially by frictional forces. Optionally, porous structure 104 is sewn and/or mechanically entangled onto support element 102. Optionally, heating, pressure, laser welding, UV curing and/or ultrasound are used as techniques to secure porous structure 104 to support element 102. Optionally, a primer, such as parylene, is used on support element 102 prior to adhering porous structure 104 to it in order to enhance cohesion.

Figure 21B:
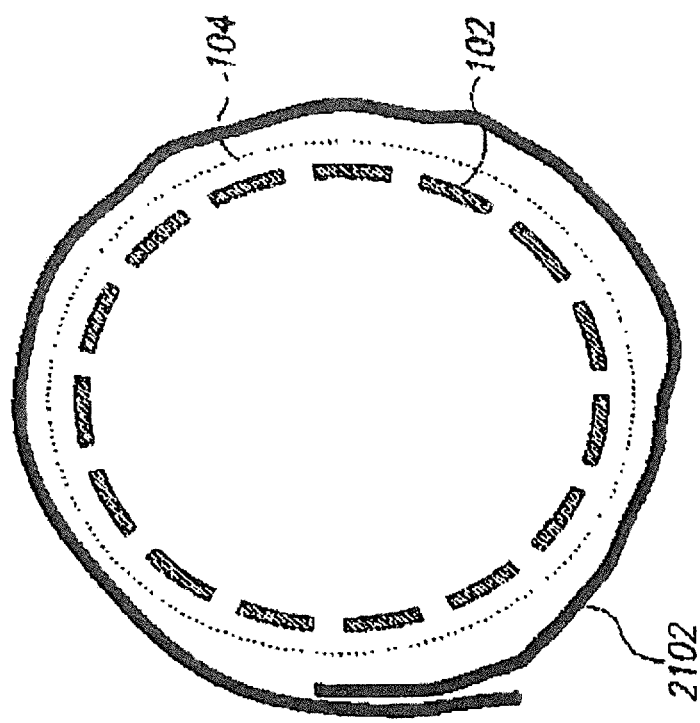
FIG. 21B is a cross-sectional view of a slip ring in a deployed configuration, in accordance with an exemplary embodiment of the invention.
Figure 21A:
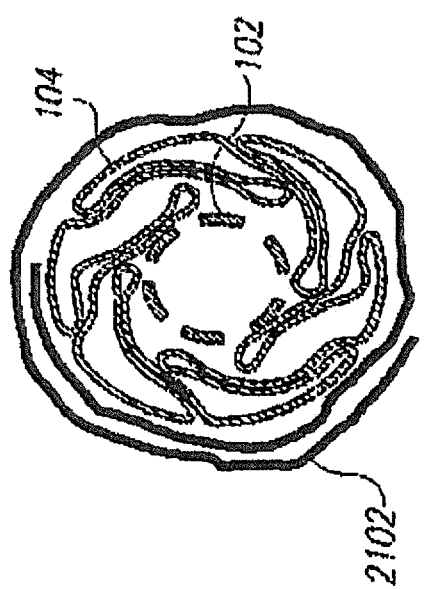
FIG. 21A is a cross-sectional view of a slip ring in a reduced profile configuration, in accordance with an exemplary embodiment of the invention.

In some exemplary embodiments of the invention, elastic and/or expandable o- and/or c-rings are used to hold porous structure 104 on support element 102. Optionally, c-rings are used to avoid hampering expandability of porous structure 104. Optionally, the rings are used to at least temporarily secure and/or apply friction to each end of porous structure 104 to support element 102. Optionally, the rings are coated and/or embedded with pharmaceuticals for elution, such as described herein. Optionally, the rings are constructed of a polymer based material. In some exemplary embodiments of the invention, porous structure 104 is tied to support element 102, optionally using fibers of porous structure 104. In an exemplary embodiment of the invention, a slip ring 2102 is used to secure porous structure 104 to support element 102, as shown in FIGS. 21A and B. Slip ring 2102 is adapted to expand with porous structure 104 and support element 102 when they are expanded upon deployment at a lumen treatment site. Optionally, slip ring 2102 is flexible but is rigid enough to secure porous structure 104 to support element 102. In an embodiment of the invention, slip ring 2102 is coiled around enhanced stent apparatus 100 when it is in a reduced profile configuration such that slip ring 2102 overlaps itself at least partially. Upon deployment, shown in FIG. 21B, support element 102 and porous structure 104 are expanded to provide treatment to the lumen. In an embodiment of the invention, slip ring 2102 expands with them while maintaining sufficient pressure on porous structure 104 to retain it to support element 102. In an embodiment of the invention, the overlapping portion of slip ring 2102 is reduced as a result of the overall increase in diameter of the slip ring 2102. Optionally, slip ring 2102 is comprised of a biodegradable and/or bioresorbable material. In some embodiments of the invention, slip ring 2102 is under 25 microns thick. Optionally, slip ring 2102 is under 15 microns thick. Optionally, slip ring 2102 is under 10 microns thick.

Figure 16:
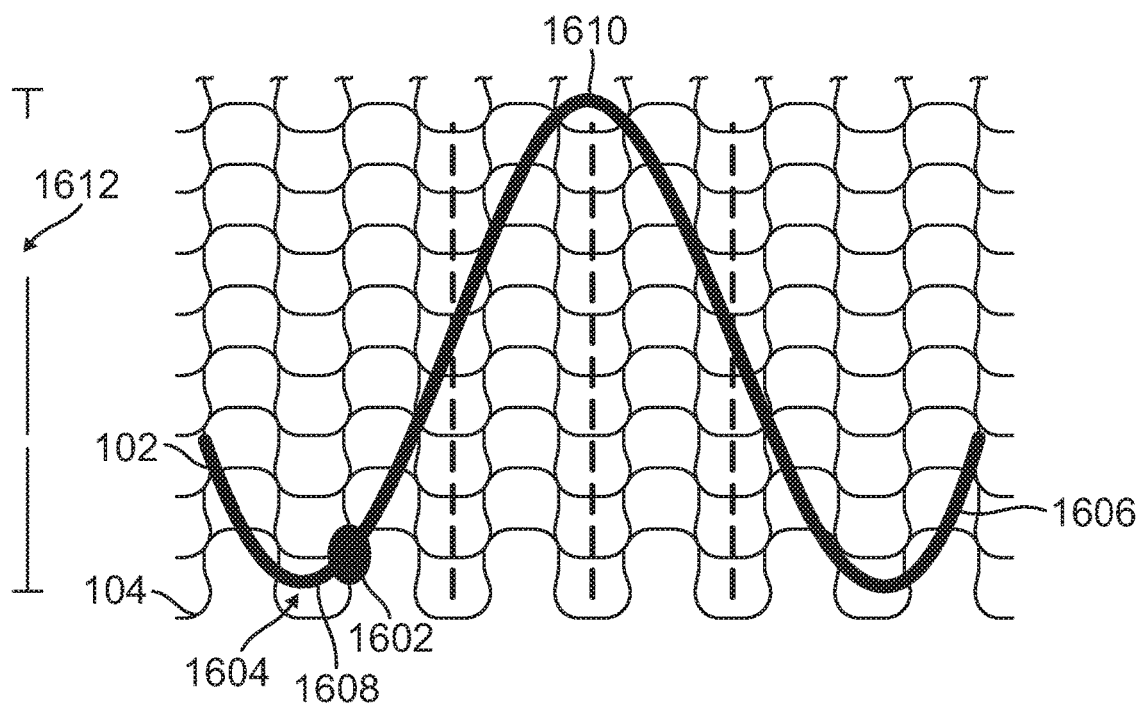
FIG. 16 is a detailed illustration of a threading method for securing a porous structure to a support element, in accordance with an exemplary embodiment of the invention.

Referring to FIG. 16, an embodiment of the invention is shown in which porous structure 104 is attached to support element 102 using a sliding connection 1602. In an exemplary embodiment of the invention, the sliding connection is established by attaching at least one loop 1604 of porous structure 104 to support element 102 in a condition that prevents the two from becoming separated, but is loose enough to allow sliding of porous structure 104 with respect to support element 102. In an embodiment of the invention, a loose stitch is used to attach porous structure 104 to support element 102 in a sliding connection. In an embodiment of the invention, expansion of porous structure 104 is assisted by utilizing the sliding nature of the connection 1602. For example, porous structure 104 is secured to the outermost strut 1606 of support element 102 at its most outlying position 1608. In an embodiment of the invention, on the other side of support element 102 porous structure 104 is also attached to the outermost strut at its most outlying position. When support element 102 and porous structure 104 are expanded during deployment, porous structure 104 is afforded additional expandability, in relation to a pre-expanded configuration, as the sliding connection 1602 moves from the most outlying position 1608 on outermost strut 1606 to an innermost position 1610. The distance 1612, about 1 mm to 6 mm in an embodiment of the invention, from the most outlying position 1608 to innermost position 1610 provides additional expandability to porous structure 104. Optionally, sliding is prevented by securing porous structure 104 to strut 1606 at innermost position 1610 as well as most outlying position 1608. Optionally, sliding is prevented by tightening the connection between the two, for example by providing a tighter stitch.

Figure 17:
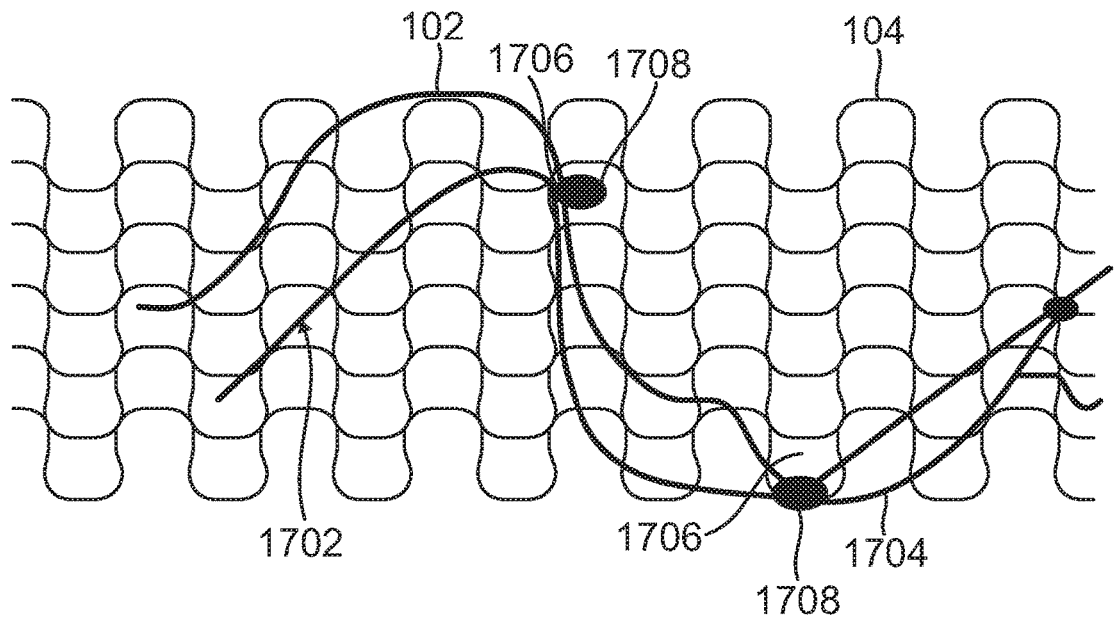
FIG. 17 is a detailed illustration of a knotting method for securing a porous structure to a support element, in accordance with an exemplary embodiment of the invention.

In some embodiments of the invention, porous structure 104 is tied to support element 102 using any one of thumb, square, reef, or double surgeon's knots. Optionally, the at least one fiber used to construct porous structure 104 is used to tie porous structure 104 to support element 102. FIG. 17 shows an exemplary method for attaching porous structure 104 to support element 102 using knotting. It can be seen that a knotting fiber 1702 is used to secure porous structure 104 to support element 102 at various points along a support element strut 1704. Optionally, knotting fiber 1702 is threaded through a plurality of eyes 1706 and over support element strut 1704 wherein a knot 1708 is tied to secure porous structure 104 to support element 102 at least some of the eyes.

As mentioned above, in some embodiments of the invention, securing porous structure 104 to support element 102 is also used to reduce the likelihood of run outs and/or porous structure unraveling. In an embodiment of the invention, run outs and/or porous structure unraveling are to be avoided for at least the reasons of: avoiding porous structure protrusion into the lumen and/or rendering porous structure ineffective for intended treatment of the lumen. In an embodiment of the invention, porous structure 104 is secured to support element 102 at the ends of support element 102, at least some intersections where porous structure 104 and support element 102 overlap, or both and/or every eye at both ends. Any of the methodologies of securing described above are optionally used to secure porous structure 104 to support element 102 to prevent run outs and/or unraveling.

In an exemplary embodiment of the invention, porous structure 104 is treated to supply temporary enhanced adhesion to support element 102 during implantation.

For example, enhanced stent apparatus 100 is optionally dipped in a liquid which causes porous structure 104 to adhere to support element 102. Optionally, this adherence is due to surface tension of the liquid. Optionally, this adherence is due to temporary shrinkage of porous structure 104, which secures it to support element 102 more tightly. In some exemplary embodiments of the invention, temporary cohesion is used to prevent porous structure 104 from slipping off of support element 102 as a result of frictional stress experienced during navigation of the vasculature during implantation.

General Pharmacological Usage

Alternatively or additionally to the physical prevention of debris from entering the bloodstream, porous structure 104 optionally contains pharmaceuticals designed to treat a variety of ailments. In some exemplary embodiments of the invention, pharmaceuticals are optionally provided including one or more pharmacological agents for encouraging cell and/or liposomal growth and/or other endothelial cell growth factors, anti-proliferative, anti-thrombotic, anti-coagulant and/or anti-platelet effects, tissue engineering factors, immunomodulators, antioxidants, antisense oligonucleotides, collagen inhibitors, hydrophobic pharmaceuticals, hydrophilic pharmaceuticals and/or endothelial cell seeding substances. Optionally, pharmacological therapy rendered from a porous structure is used to accelerate vein to artery conversion. Specific examples of pharmaceuticals that are optionally used with porous structure 104 include: anti-proliferative agents like sirolimus, zolimus or zotarolimus (ABT-578®), paclitaxel and other taxanes, tacrolimus, everolimus, vincritine, viblastine, HMG-CoA reductase inhibitors, doxorubicin, colchicine, actinomycin D, mitomycin C, cycloporine, and/or mycophenolic acid, triazolopyrimidine and its derivatives (i.e. Trapidil®, a coronary vasodilating drug); intrapide, glucocorticoids like dexamethasone, methylprednisolone, and/or gamma interferon; antithrombotics like heparin, heparin-like dextran derivatives, acid citrate dextrose, coumadin, warfarin, streptokinase, anistreplase, tissue plasminogen activator (tPA), urokinase and/or abciximab; antioxidants like probucol; growth factor inhibitors like tranilast and/or angiopeptin; antisense oligonucleotides like c-myc and/or c-myb; collagen inhibitors like halofuginone and/or batimistat; liposomes; gemcitabine (i.e. Gemzar®); steroids and corticosteroids for example cortisone and prednisone; cortisone, prednisone; sirolimus (Rapamycin®); statin drugs like lovastatin and/or simvastatin (i.e. Zocor®); VEGF; FGF-2; micro carriers containing endothelial cells; genes; DNA; endothelial cell seeds; and/or hydrogels containing endothelial cells.

Typically, stents (i.e. support elements) which provide pharmaceutical treatment only have the pharmaceutical embedded on the structure of the stent, in particular on the stent struts. This structure is typically minimized in order to provide flexibility and reduce cost, among other reasons. As a result of a minimized support element structure, the struts of the structure are usually spaced widely apart. Thus, when the stent is in situ, and pharmaceuticals are released into the patient from the stent, the pharmaceutical is only diffused from the widely spaced struts. This prevents even distribution of the pharmaceutical over the entire length of the stent. In addition, stent struts are typically large in relation to endothelial cells and therefore formation of a covering endothelial cell layer typically takes on the order of days or weeks, rendering pharmaceutical elution into body tissues delayed and/or ineffective (due to a number of reasons, including the pharmaceutical being washed away by fluids flowing in the lumen before the endothelial cell layer covers the stent).

In contrast, usage of a pharmaceutical enhanced porous structure, such as described herein, to cover the stent, including the struts, provides far more surface area in contact with the inner wall of the patient's blood vessel, thereby enabling more diffusion to take place. In comparison to conventional techniques for stent delivered pharmaceuticals, lower concentrations of pharmaceutical are optionally used with the present invention because of its improved therapy-rendering surface area. In an embodiment of the invention, improved delivery by the presently described invention allows for lower doses of pharmaceutical to be used in order to render the same relative amount of treatment, and reduce the overall dosage needed in order to obtain the same results, thus reducing possible side effects. For example, a currently recommended concentration of taxol on a drug eluting stent is around 1 µg/mm$^2$ of stent surface. In contrast, a concentration of 0.5 µg/mm$^2$ is optionally used with porous structure 104, due to its increased treatment rendering surface area. Optionally, the concentration is less than 0.5 µg/mm$^2$. As another example, typical concentrations of rapamycin and 'limus drugs today are around 140 µg/mm$^2$, however, using the herein described porous structure 104 a concentration of 80 µg/mm$^2$ is optionally used to achieve the same therapeutic effect. In some exemplary embodiments of the invention, as little as 10 µg/mm$^2$ is optionally, used to achieve the same therapeutic effect. In some exemplary embodiments of the invention, concentrations of pharmaceutical embedded on porous structure are up to 15 times less than conventionally used today.

In conventional stents, at the struts, the pharmaceutical may not propagate far enough and/or without effect into the vascular wall, or may overdose a particular section of the vascular wall, without sufficient propagation laterally to the rest of the inner surface where it is needed. Having additional surface area more evenly covering the stent surface area, porous structure 104 can deliver drugs in a more locally homogenous way. Optionally, there is an axial profile change in dosage. Since distribution of the drug into the tissue is governed by diffusion, and since the amount of dosage concentration on the struts is limiting due to over toxicity and side effects, spreading the drug in a more even manner is very helpful for obtaining better pharmacokinetics.

In an exemplary embodiment of the invention, pharmaceuticals to be administered to patient are located in and/or on the fibers of porous structure 104. Examples of where and how pharmaceuticals are optionally located in and/or on the fibers of porous structure 104 and/or eluted include:

1. depositing pharmaceutical in the apertures of porous structure;
2. mixing pharmaceutical particles into fibers of porous structure at fiber creation;
3. applying pharmaceutical topically to the porous structure, such as by spraying;
4. dipping porous structure into a solution containing a pharmaceutical additive, thereby depositing the additive on and/or in the fibers of the porous structure;
5. encapsulating a pharmaceutical additive on porous structure, optionally using a thermal process;
6. grafting a pharmaceutical additive onto porous structure using plasma treatment;
7. etching a pharmaceutical additive into porous structure, for example via spattering or coating;
8. transferring a pharmaceutical additive to porous structure using concentration differences between the porous structure and an additive containing substance, for example by adhering micro carriers containing to pharmaceutical additive to a porous structure allowing their migration into the porous structure;
9. any method known to those of ordinary skill in the art, such as shown in U.S. Pat. App. No. 2004/0030377 to Dubson et al., U.S. Pat. App No. 2005/0187140 to Hunter et al., U.S. Pat. App. No. 2004/0236407 to Fierens et al., U.S. Pat. No. 6,902,522, to Walsh, et al., U.S. Pat. No. 6,669,961 to Kim, et al., U.S. Pat. No. 6,447,796 to Vook et al., U.S. Pat. No. 6,369,039 to Palasis et al., U.S. Pat. No. 6,939,374 to Banik, et al., and U.S. Pat. No. 6,919,100 to Narayanan, the contents of which are incorporated herein by express reference thereto;
10. elution of the drug from a polymer coating the porous structure fibers;
11. elution of the drug from the polymer from which the porous structure is constructed; and,
12. incorporating the drug in a biodegradable polymer.

Optionally, embedding of the pharmaceutical occurs before (e.g. mixing pharmaceutical particles into fibers of porous structure at fiber creation), during (e.g. using the dipping method of FIG. 19) and/or after (e.g. a spray on pharmaceutical after apparatus is made) the manufacture of enhanced stent apparatus 100. In some exemplary embodiments of the invention, a pharmaceutically embedded porous structure 104 is placed on top of a pharmaceutically treated support element 102. In some exemplary embodiments of the invention, porous structure 104 is coated with at least a polymer. In some exemplary embodiments of the invention, a porous structure is provided with a polymer coating which contains a pharmaceutical which elutes from the coating.

Pharmaceuticals are optionally embedded into porous structure 104 such that they are released into the patient over an approximate predetermined amount of time. For example, pharmaceuticals are optionally embedded into porous structure 104 for release over the course of a week. Other pharmaceuticals are optionally embedded into porous structure 104 for release over the course of months. Factors which vary according to the release schedule of the pharmaceutical include the type of material used to construct porous structure 104, the type of pharmaceutical being used, the manner in which porous structure 104 is constructed, and/or the amount of coverage of support element 102 that porous structure 104 provides.

In some exemplary embodiments of the invention, 1 microgram of pharmaceutical per square centimeter of fiber surface coverage (not the area of the fiber themselves, but the area of the tissue it treats) area is embedded on the fibers. Optionally, up to 200 micrograms of pharmaceutical per square centimeter of fiber surface area is embedded on the fibers. Optionally, a higher or lower concentration of pharmaceutical is used depending on the therapeutic needs of the patient and depending on the type of drug used.

Large and/or Complicated Stereochemistry Molecule Pharmaceutical Usage

In some exemplary embodiments of the invention, usage of porous structure 104 for enhanced pharmaceutical delivery allows for effective dispersion and delivery of large molecule and complex stereochemistry pharmaceuticals. Traditionally, large molecule pharmaceuticals are not used with drug eluting stents because they don't diffuse very well and the widely spaced struts of traditional stents do not facilitate even and/or widespread diffusion of the large molecule, as described above. In contrast, use of a device with more extensive coverage of a vascular wall would make treatment using large molecule pharmaceuticals more feasible. This is optionally accomplished by providing porous structure 104 and/or support element 102 with large molecule pharmaceuticals for elution and taking advantage of the increased vascular wall coverage of porous structure 104, due to the smaller aperture sizes in some exemplary embodiments. Alternatively or additionally, due to the overgrowth of porous structure 104 by cells from the body, large molecule pharmaceuticals are more efficiently delivered to the patient as pharmaceuticals are delivered into tissue, rather than being washed away in the blood stream, for example. Optionally, pharmaceuticals larger than 700 Dalton, 1,000 Dalton, 3,000 Dalton or up to 50,000 Dalton are dispersed and delivered evenly into patient's vasculature.

Figure 3:
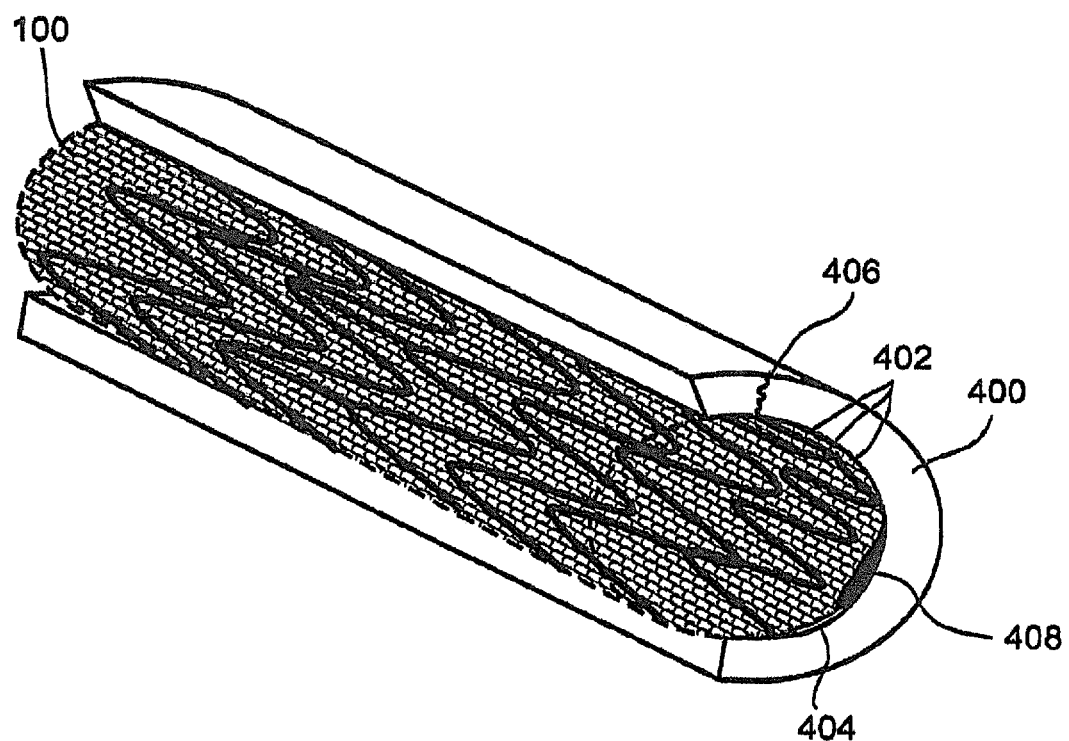
FIG. 3 is an illustration of an enhanced stent apparatus in an open mode in situ, in accordance with an exemplary embodiment of the invention.

Optionally, liposomes are eluted from at least one porous structure 104 and/or support element 102. Optionally, steroids, statins, anticoagulants, gemcitabine (Gemzar®), zolimus or zotarolimus (ABT-578®), sirolimus (e.g. Rapamycin®), taxol/paclitaxel, and/or other large or complex molecule pharmaceuticals are eluted from at least one porous structure 104 and/or support element 102. Referring to FIG. 3, pharmaceutical agents 406 are shown eluting from enhanced stent apparatus 100 into artery 400 from lumen wall 404. Optionally, agents 406 elute from porous structure after at least some growth of endothelial cells 408 through enhanced stent apparatus 100, for example the time determined by experimental endothelial cell growth data. As described elsewhere herein, porous structure 104 optionally acts to trap debris 402 between the exterior surface of enhanced stent apparatus 100 and lumen wall 404.

Timed Release Pharmaceutical Usage

In an exemplary embodiment of the invention, pharmaceuticals are eluted from an enhanced stent apparatus into overgrown endothelial tissue and not merely into the interior surface of the lumen being treated. In an exemplary embodiment of the invention, pharmaceutical release is thus optimized by ensuring that only a pre-defined amount of drug is lost into the bloodstream and/or into other non-therapeutic media. In some exemplary embodiments, including, for example, in conjunction with BBB treatment as described below, endothelial cell growth can assist with pharmaceutical therapy by providing a transfer medium for the pharmaceutical from an implanted stent to the body area being treated.

In some exemplary embodiments of the invention, pharmaceuticals are eluted depending on the extent of endothelial tissue growth. Optionally, pharmacological treatment commences after some endothelial cell growth is exhibited through and/or around the enhanced stent apparatus. Optionally, pharmacological treatment begins upon implantation without regard to endothelial cell growth. In some exemplary embodiments of the invention, the enhanced stent apparatus is adapted and constructed to time-release pharmaceuticals in accordance with a predetermined treatment schedule. Optionally, the predetermined treatment schedule accommodates anticipated and/or actual endothelial cell growth rates by utilizing a coating with a predetermined breakdown rate. Optionally, release of pharmaceuticals is determined by time in situ. For example, if it is estimated that it would take 8 hours for endothelial cell growth to completely encapsulate the implanted stent, pharmaceuticals located in the porous structure of the stent optionally have a predetermined 8 hour delay prior to release and/or elute at a low rate to prevent inefficient or undesirable (i.e. toxic overdose) use of the pharmaceutical. In an embodiment of the invention, it takes only few hours for the endothelial cells to cover the thin porous structure, therefore the time release delay is adapted to match. This may be achieved by coating porous structure 104 with a "diffusion barrier" layer that to inhibits the diffusion of drug for a predefined period. Optionally this may be achieved by using a controlled degradable matrix. Optionally, pharmaceutical release occurs after only partial growth of endothelial cells around and/or through porous structure and/or stent. Optionally, pharmaceuticals begin to elute immediately upon insertion and/or implantation into a body lumen. Optionally, it is sufficient for pharmaceutical therapy that porous structure 104 has any biological covering, such as mucus, etc. In some embodiments of the invention, delay is determined according to the material that is expected to overgrow porous structure 104.

In an exemplary embodiment of the invention, timed release of pharmaceuticals is accomplished by coating and/or constructing porous structure 104 and/or support element 102 of multiple biodegradable/resorbable layers. By using layers which offer different performance characteristics (e.g. different pharmaceutical, different degradation time, stickiness to the body lumen, surface treatment modifications (e.g. treatment to make it non-sticky to the lumen)), enhanced stent apparatus 100 can be tailored to perform a specific treatment schedule. For example, layer #1 (the external layer) is comprised of a material which degrades in 2 hours, layer #2 (an inner layer) includes a pharmaceutical for elution into the patient and which degrades in 10 hours minutes, layer #3 (an inner layer) includes a different pharmaceutical for elution into the patient which degrades in 6 hours, and so on. Naturally, depending on the therapy desired for the patient, the layers and/or performance characteristics of those layers are changed to provide the desired treatment. It should be noted that a biodegradable layer can be placed in the outermost position which is timed to the expected endothelial cell growth, as described above. In such an embodiment, the degradation of the outermost layer is completed at approximately the same time as the completion of the endothelial cell layer overgrowth of enhanced stent apparatus 100, enabling a pharmaceutical to be eluted directly into endothelial tissue from a second layer of enhanced stent apparatus 100.

In an exemplary embodiment of the invention, support element 102 elutes pharmaceuticals, but treatment is assisted by porous structure 104 which encourages endothelial cell growth over support element 102. Optionally, the pharmaceutical located on support element 102 elutes slowly to allow for endothelial cell growth. In some embodiments of the invention, the rate of elution depends on the local concentration and the anticipated diffusion rate of the pharmaceutical through the surrounding body tissue.

In some embodiment of the invention, a first pharmaceutical agent is eluted, which is designed to encourage endothelial cell overgrowth, followed by a second pharmaceutical agent designed to treat a malady of the patient.

In some embodiments of the invention, at least porous structure 104 is attached to the lumen using an adhesive which is impermeable to the pharmaceutical in porous structure 104. However, timed release is achieved by allowing the endothelial layer to overgrow porous structure 104, such that the pharmaceutical will elute into the endothelial layer that is not proximal to the adhesive. Optionally, the adhesive is biodegradable and/or bioresorbable and merely delays elution.

Blood Brain Barrier (BBB) Therapy

The BBB is the specialized system of capillary endothelial cells that protects the brain from harmful substances in the blood stream, while supplying the brain with the required nutrients for proper function. Unlike peripheral capillaries that allow relatively free exchange of substance across/between cells, the BBB strictly limits transport into the brain through both physical (tight junctions) and metabolic (enzyme) barriers. Thus the BBB is often the rate-limiting factor in determining permeation of therapeutic drugs into the brain.

In some exemplary embodiments of the invention, a pharmaceutical eluting porous structure is used to enable treatments through the BBB. As described herein, pharmaceutical therapy is often enhanced by endothelial cell growth through and/or around an implanted drug eluting stent. Use of porous structure 104 in brain arteries, allows the endothelium cells to grow over the porous structure 104, thus embedding porous structure 104 into the arterial tissue. The end result, after the previous endothelial cell layer has been absorbed by the body is that porous structure 104, which contains a brain treating pharmaceutical, is on the other side of the endothelium layer, thus on the other side of the BBB, with no significant impediment between porous structure 104 and the brain tissue. In addition, some exemplary embodiments of porous structure 104 are suitably sized to be used in the narrow lumens found in the brain. Exemplary pharmaceuticals suitable for use with porous structure 104 in treating through the BBB include gemcitabine (Gemzar®), and enzastamin, dopamine and dopamine derivatives, and anti-cancer drugs. In some embodiments of the invention, porous structure 104 elutes anti-BBB materials for lowering resistance to transmission of substances through the BBB.

Pharmaceutical Treatment of Small Lumens

Currently, small lumens such as small coronary or brain arteries are treated only with a balloon type catheter. These treatments are short term and do not lend themselves to rendering pharmaceutical treatment to the lumen, as is sometimes desired. Traditional stenting is not often performed at the very least due to the difficulty of navigating a stent into the small spaces of these arteries. In an exemplary embodiment of the invention, lumens smaller than 2 mm in diameter are treated with pharmaceuticals using at least a pharmaceutical eluting porous structure 104, and optionally a support element. Optionally, the support element is a stent. Optionally, the support element is a balloon on which porous structure 104 is placed. In an exemplary embodiment of the invention, a balloon-type catheter is used to insert porous structure 104 in a small lumen. The balloon is expanded to cause porous structure 104 expansion and to instigate contact between porous structure 104 and the lumen wall to be treated. In an embodiment of the invention, porous structure 104 at least partially adheres to the lumen wall. Optionally, a biocompatible adhesive is used to adhere porous structure 104 to the lumen wall. In some embodiments of the invention, porous structure 104 is self-expandable and does not need, or only partially relies on the balloon for expansion. In an embodiment of the invention, the balloon is removed once porous structure has been deployed within the small lumen.

In some embodiments of the invention, small lumens are treated long term, which is not performed currently. For example, by implanting at least the porous structure of an enhanced stent apparatus 100, treatment can last on the order of months (e.g. a month or more). Optionally, treatment can last on the order of weeks (e.g. a week or more).

Exemplary Treatment Methods

In an exemplary embodiment of the invention, enhanced stent apparatus 100 is used for treating, dilating, drugging and/or supporting body lumens, such as blood vessels. In some exemplary embodiments of the invention, enhanced stent apparatus 100 is used for treatment of disorders in the carotid arteries. In some embodiments of the invention, enhanced stent apparatus 100 is used for treatment of disorders in the coronary arteries. As described above, treatment can be rendered through the BBB. Stent apparatus 100 can be either a balloon expandable stent or a self-expandable stent, or use any other expansion method. Optionally, support element 102 and/or porous structure 104 are self-expandable. Optionally, pharmaceuticals are used to treat a patient via body lumens, for example, as described herein. In some embodiments of the invention, enhanced stent apparatus 100 is used for treatment of aneurisms (described below), for example in the brain. In some embodiments of the invention, enhanced stent apparatus 100 is used for preventative treatment of vulnerable plaque.

In operation, enhanced stent apparatus 100 is navigated to the area in a body lumen 400, as shown in FIG. 3, where the enhanced stent apparatus 100 is to be emplaced, using techniques known in the art. In some exemplary embodiments of the invention, enhanced stent apparatus 100 can be expanded within body lumen 400 using a balloon. Optionally, enhanced stent apparatus 100 can be expanded within body lumen 400 using self-expandable techniques known in the art. Optionally, support element 102 and/or porous structure 104 are constructed of a thermo-sensitive, shape memory alloy which, when exposed to a patient's natural body temperature, assumes an expanded shape within body lumen 400 at some time after situation in the appropriate location to render treatment. Alternatively, super-elastic or elastic release is used for placing a stent in a treatment area. In some exemplary embodiments of the invention, a balloon is used to pre-dilate body lumen 400 at a treatment area prior to implantation of enhanced stent apparatus 100 at that area, in an at least a two-step (1. pre-dilate, 2. implant apparatus 100) procedure. Optionally, only porous structure 104 is implanted and not the whole enhanced stent apparatus 100. In some exemplary embodiments of the invention, a balloon is used to post-dilate body lumen 400 at a treatment area after implantation of enhanced stent apparatus 100 at that area, in an at least a two-step (1. implant apparatus 100, 2. post-dilate) procedure. This kind of procedure is commonly used when implant apparatus 100 is a self-expandable stent, such as for carotid applications.

In some exemplary embodiments of the invention, the porous structure mesh is filled with a material which improves the stiffness of the porous structure temporarily until it arrives at a treatment site in a lumen. In some embodiments of the invention, the material is dissolved by naturally occurring substances in the body, such as enzymes. Optionally, the dissolving is timed to the anticipated overgrowth of porous structure 104 by the endothelial cell layer. Optionally the material is fibrogane. Optionally, the material is albumin fibrogane helonic acid laminin.

Exemplary Treatment of Embolic Showers at Insertion and/or Deployment

It is commonplace in stenting procedures to use an embolic shower protection device which is situated only during the stenting procedure downstream from the treatment area, the idea being that the protection device will trap debris which falls from the blood vessel walls during the stenting procedure. In an exemplary embodiment of the invention, usage of enhanced stent apparatus 100 with porous structure 104 obviates the need for an embolic shower protection device. The small aperture size of porous structure 104 is designed to trap arterial wall plaque 402 and other debris of a particular size that becomes dislodged during and/or after the stenting procedure, between porous structure 104 and the lumen wall 404. In an exemplary embodiment of the invention, debris greater than the size of the apertures in diameter is prevented from entering the bloodstream in this manner.

An additional advantage of using implanted porous structure 104 instead of a conventional embolic shower protection device is that it remains in place after the procedure. That is, debris which becomes dislodged at some time after the stenting is performed still becomes trapped by porous structure 104. This is an improvement over the embolic shower protection device conventionally used, which is removed at the conclusion of the stenting procedure. Optionally, enhanced stent apparatus 100 is used with an embolic shower protection device as reassurance during the stenting procedure. Optionally, porous structure 104 filters a particular type or types of debris while support element 102 filters another type or types.

It should be noted further that in an exemplary embodiment of the invention the aperture sizes of the porous structure 104 are designed and constructed to permit the passage of blood therethrough. This prevents the "jailing" of branching blood vessels which prevents the passage of critical blood components, such as red blood cells from passing into the branching vessel. In an exemplary embodiment of the invention, the aperture size of porous structure 104 is larger than the average size of a red blood cell, or about 7 microns, allowing throughput of red blood cells without the risk of producing significant hemolysis. In some exemplary embodiments of the invention, the approximate aperture diameters are greater than 20 microns. In some exemplary embodiments of the invention, the approximate aperture diameters are smaller than 100 microns thus allowing blood to flow through while holding large debris (>100 microns) in place.

Carotid stenting is rarely performed currently, due to the high risk of debris becoming dislodged during the stenting procedure. This dislodged debris then travels to the brain where it often causes serious injury to the patient. In order to combat this problem of dislodged debris, enhanced stent apparatus 100, which includes porous structure 104, is used for stenting in the carotid arteries in some exemplary embodiments of the invention.

Exemplary Treatment of Aneurisms

Figure 20A:
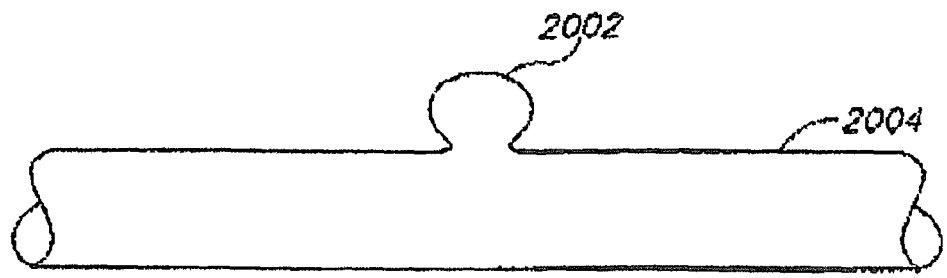
FIG. 20A is an illustration of a typical aneurism.
Figure 20B:
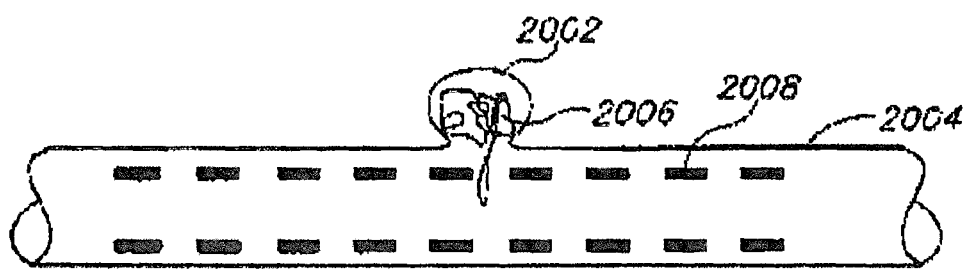
FIG. 20B is an illustration of a prior art technique for treating an aneurism.

Referring to FIG. 20A, a typical aneurism volume 2002 is depicted promulgating from a body lumen 2004. FIG. 20B shows a current method of treating an aneurism called coil embolization. Coil embolization is particularly indicated for treatment of cerebral aneurisms. Coil embolization of cerebral aneurisms involves the insertion of a catheter through the groin with a small microcatheter navigated to the aneurism itself through the cerebral arteries. A coil 2006 is then deployed into the aneurism filling it from within and thus disturbing the blood flow in the aneurism volume. This effect that leads to the creation of blood clot, which is trapped in aneurism volume 2002 and which eventually turns into a more solid structure, thus reducing the risk of rupture of the aneurism. In some treatments, a stent 2008 is also used in order to keep coil 2006 from falling out of aneurism volume 2002 and into the blood stream. However, in some cases parts of coil 2006 protrude through stent 2008 and are therefore exposed to the blood flow within the lumen 2004. Additionally, safe insertion of coil 2006 into aneurism volume 2002 can be a complicated procedure. Additionally, the blood clot produced might grow through the stent struts into the blood vessel lumen, narrowing it possibly to the point of complete occlusion.

Figure 20C:
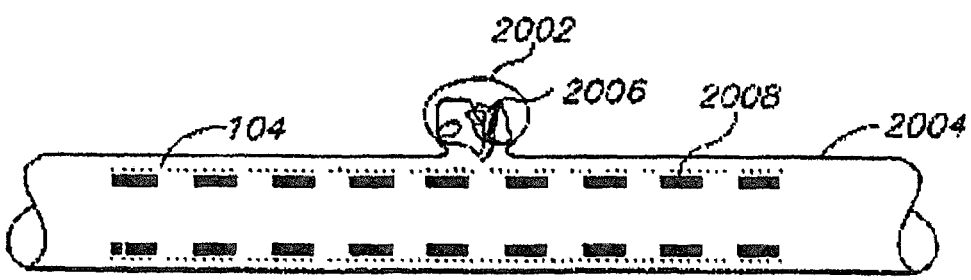
FIG. 20C is an illustration of a technique for treating an aneurism, in accordance with an exemplary embodiment of the invention.

Referring to FIG. 20C, an embodiment of the invention is shown in which porous structure 104 located on enhanced stent apparatus 100 is used to treat an aneurism while preventing coil 2006 from protruding into lumen 2004. Optionally, a cerebral aneurism is treated by this method. Porous structure 104 is adapted to have aperture sizes which are small enough to prevent coil 2006 from protruding into lumen 2004, in accordance with an embodiment of the invention. Optionally, a plurality of porous structures are used at least slightly out of phase in order to prevent at least a portion of coil 2006 from protruding into lumen 2004. In some exemplary embodiments of the invention, coil 2006 is covered with a porous structure (separate from porous structure 104), thereby creating more surface area for the blood to stick to, enhancing the creation of a blood clot within the aneurism volume 2002. In some embodiments of the invention, porous structure 104 is manufactured using an electrospinning technique.

In an exemplary embodiment of the invention, enhanced stent apparatus 100 is used to treat an aneurism without the need for coil 2006. In some embodiments of the invention, porous structure 104 is adapted to restrict blood flow into aneurism volume 2002, thus causing the trapped blood in aneurism volume 2002 to clot, which in time will solidify and create a solid tissue structure thus reducing the likelihood of aneurism rupture or expansion as a result of increased blood flow thereto. For example, the aperture sizes in porous structure 104 may be small or spaced widely apart. Optionally, a plurality of "out of phase" porous structures are used together to restrict blood flow into aneurism volume 2002. Optionally, porous structure 104 has apertures smaller than 20 microns. Eliminating the need of coil 2006 is advantageous, as it makes the procedure faster, safer, and simplifies the delivery catheter that can be used to perform the procedure.

In some exemplary embodiments of the invention, porous structure 104 is shorter than support element 102. A shorter porous structure 104 is optionally used so that only the aneurism is treated and not a healthy portion of the lumen. Optionally, a shorter porous structure 104 is used to avoid restricting blood flow to a branching vessel. Optionally, porous structure 104 has small aperture sizes on the aneurism side for restricting flow therethrough, while the other side has larger apertures to avoid restricting blood flow to a branching vessel.

In some exemplary embodiments of the invention, porous structure 104 is comprised of a self-expanding material, such as nitinol, having enough radial force to hold itself in place within the lumen. Optionally, a support element 102 is not used at all and porous structure 104 provides the necessary treatment to the aneurism. Optionally, the radial pressure applied by porous structure 104 is equivalent to about 1 atmosphere. Optionally, the aperture diameters for aneurism treatments are smaller than 30 microns.

In some embodiments of the invention, porous structure 104 also prevents blood clots and/or other embolism-causing debris from entering the lumen 2004 from aneurism volume 2002.

Exemplary Treatment of Vulnerable Plaque

Identification of vulnerable plaque areas allows prophylactic treatment of these areas before they can create problems for the patient. In an embodiment of the invention, an enhanced stent apparatus 100 is used to preemptively treat lumen areas expected to trigger problematic conditions for the patient in the future. For example, plaque often builds up in blood vessels which in some cases breaks off in a clump or partially tears, causing a thrombosis. The downstream movement of the plaque or thrombosis is a potential cause of a heart attack, stroke or other malady in the patient. In some embodiments of the invention, an enhanced stent apparatus, including at least porous structure 104 is implanted at a potentially problematic location within a lumen, preventing the plaque from rupturing and, thus, from entering the bloodstream. In some embodiments of the invention, porous structure 104 elutes at least one pharmaceutical used for treating the condition affecting the lumen, such as those described herein. In some embodiments of the invention, porous structure 104 is made of nitinol as a self-expandable stent, having enough radial force to hold itself in place, without the supportive element 102.

Exemplary Method of Implantation

In some exemplary embodiments of the invention, porous structure 104 is positioned on a catheter, such as an expandable balloon, for implantation in a lumen separately from or without support element 102. Treatment with a catheter is optionally provided by using the catheter to implant porous structure 104 adapted and constructed for rendering treatment to a lumen over time. Optionally, pharmaceuticals or other therapeutic agents are embedded within porous structure 104, such as described herein. Positioning, in an exemplary embodiment of the invention, entails inserting the catheter at least partially through the interior of porous structure 104 along central axis 106. In some embodiments of the invention, a balloon is deflated prior to positioning of porous structure 104 thereon. Optionally, the balloon is at least partially inflated prior to positioning of porous structure 104 thereon and then deflated and/or folded prior to insertion into the patient.

During delivery of porous structure 104 to a treatment site within a lumen, a balance is optionally struck between securing porous structure 104 to the catheter during delivery, but not so securely as to prevent implantation of porous structure 104 at the treatment site, and allowing deflation of a balloon and/or pulling the catheter out while leaving the porous structure 104 inside the lumen intact. For example, porous structure 104 is optionally adhered to catheter at selected points using an adhesive such as loctite instant adhesive number 40340, 40840, 46040 or 3411-UV curable. The adhesive is strong enough to prevent porous structure 104 from slipping off the catheter during delivery, however upon self-expansion or expansion of balloon the bonds between porous structure 104 and the catheter are broken, allowing for implantation of porous structure 104 at a treatment site within a lumen. In some embodiments of the invention, delivery lasts for 6 hours or less. Optionally, delivery lasts for 3 hours or less. Optionally, delivery lasts for 1 hour or less.

In some exemplary embodiments of the invention, the catheter is treated with an anti-sticking agent such as Parylene-c, silicon coating and/or Teflon® (PTFE) coating, to help prevent porous structure 104 from staying fastened to catheter after deployment at treatment site. Optionally, a thin film is coated onto the catheter which secures porous structure 104 to the catheter during the delivery, but dissolves upon an approximate lapsing of time, allowing porous structure 104 to be removed from the catheter. Optionally, the thin film is comprised of albumin fibrogane helonic acid laminin. Optionally, the thin film layer is up to a few microns thick. Alternatively, the thin film layer is 0.1 microns in thickness.

In some exemplary embodiments of the invention, the mesh-like structure of porous structure 104 is filled and/or encapsulated with a gel type material, such as fibrogane, fibrinogen and/or hyaluronic acid and/or laminin. The gel material stiffens porous structure 104 for delivery, however, upon extended exposure to intra-lumen conditions, the gel dissolves leaving only porous structure 104 after some period of time, for example a few hours or days.

In an embodiment of the invention, an adhesive material which is sensitive to a certain threshold (e.g. 1 atm. up to 20 atm.) of pressure is placed on porous structure 104 such that when the balloon pressures porous structure 104 against the lumen, porous structure 104 adheres to the lumen. In an exemplary embodiment of the invention, when porous structure 104 is coated with the pressure sensitive adhesive it is only coated on the lumen side of porous structure 104. Optionally, porous structure 104 is covered with a selectively adhesive material which has a high affinity for adhering to body tissue, for example fibrin sealant, biological glue, collagen, hydrogel, hydrocolloid, or collagen algirate, but limited affinity for adhesion to other substances, such as a delivery catheter or balloon.

Upon arrival at a lumen treatment site, the balloon is expanded in order to place porous structure 104, in accordance with an exemplary embodiment of the invention. As described above, porous structure 104 is optionally placed on the balloon such that when the balloon is expanded, porous structure 104 is expanded correspondingly. In some exemplary embodiments of the invention, the balloon is expanded until it begins to apply pressure to the internal surface of the lumen being treated. The amount of pressure exerted by the balloon is variable depending on the purpose and technique used to carry out the treatment. In some exemplary embodiments of the invention, the balloon is expanded to press porous structure 104 against an interior surface of the lumen being treated. Optionally, the expansion pressure is used to overcome a stenosis being treated. Optionally, porous structure 104 is at least temporarily fastened to the interior surface of the lumen with the assistance of an adhesive. In some exemplary embodiments of the invention, porous structure 104 is at least temporarily attached using at least one barb or pin located on an exterior surface of porous structure 104 facing the inside surface of the blood vessel. Optionally, the adhesive is applied to the exterior surfaces of porous structure 104 prior to insertion into the lumen. In some exemplary embodiments of the invention, once porous structure 104 is placed at the treatment site within the lumen, a support element 102 is implanted at the same site interior of porous structure 104 in relation to the interior surface of the lumen, thus sandwiching porous structure 104 between support element 102 and the lumen.

In some exemplary embodiments of the invention, porous structure 104 provides mechanical support to a blood vessel wall. Optionally, porous structure 104 support is in addition to support rendered by support element 102. Alternatively, porous structure support 104 is in lieu of support rendered by support element 102. In some exemplary embodiments of the invention, support element 102 provides no or minimal support to the blood vessel wall while supporting porous structure 104. Optionally, porous structure 104 provides pharmacological treatment to blood vessel while providing no or minimal support to blood vessel. Optionally, porous structure 104 is implanted along with support element 102, however support element 102 degrades in situ, leaving porous structure 104. Optionally, porous structure 104 prevents support structure 102 from falling apart in large pieces, permitting release of piece of support structure 102 only when below a certain threshold size, for example under 20 microns in diameter. Optionally, porous structure 104 is implanted along with support element 102, however porous structure 102 degrades in situ, leaving support element 102. This last configuration is sometimes indicated when porous structure 104 is made of a polymer containing a pharmaceutical. Eliminating the polymer and the pharmaceutical after period of time has an advantage because it reduces the likelihood of long term side effects such as thrombosis associated with the presence of the polymer and the pharmaceutical.

Stent assemblies, with or without jackets, are used in opening vessel lumens in a variety of vascular tissue including, inter alia, stenotic coronary arteries, stenotic carotid arteries and stenotic organ vasculature.

Prior Art Stent and Jacket Configurations

Figure 24A:
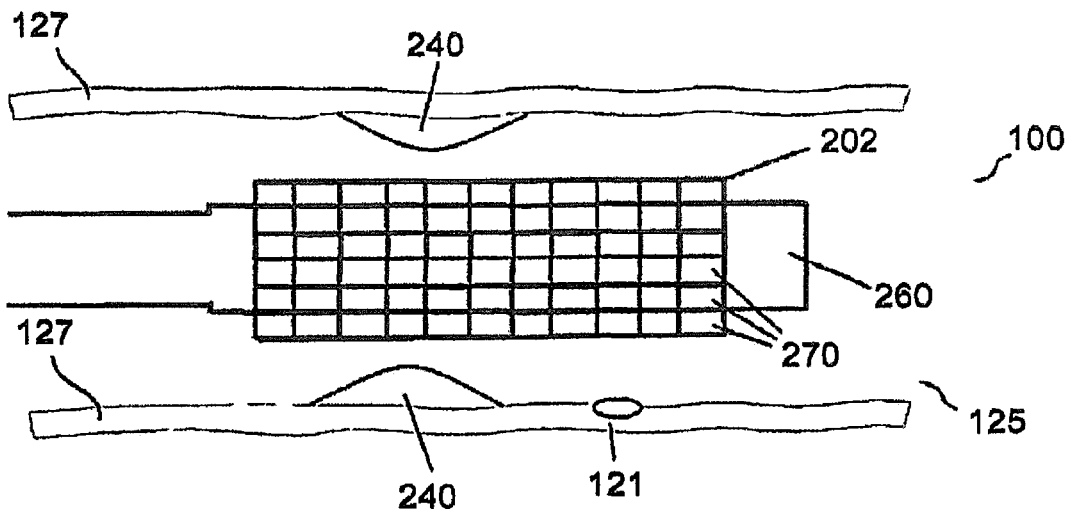
FIGS. 24a-24d show deployment of a self-expanding stent, according to embodiments of the invention.

Referring to FIG. 24a, a stent assembly 100 comprises a stand-alone tubular stent 202, without a jacket, herein bare stent 202. Bare stent 202 typically comprises a metal or polymer tubular structure having large, mesh-like, apertures 270. Bare stent 202 is shown encircling a balloon 260 and, upon expansion of balloon 260, bare stent 202 expands radially outward.

Figure 24B:
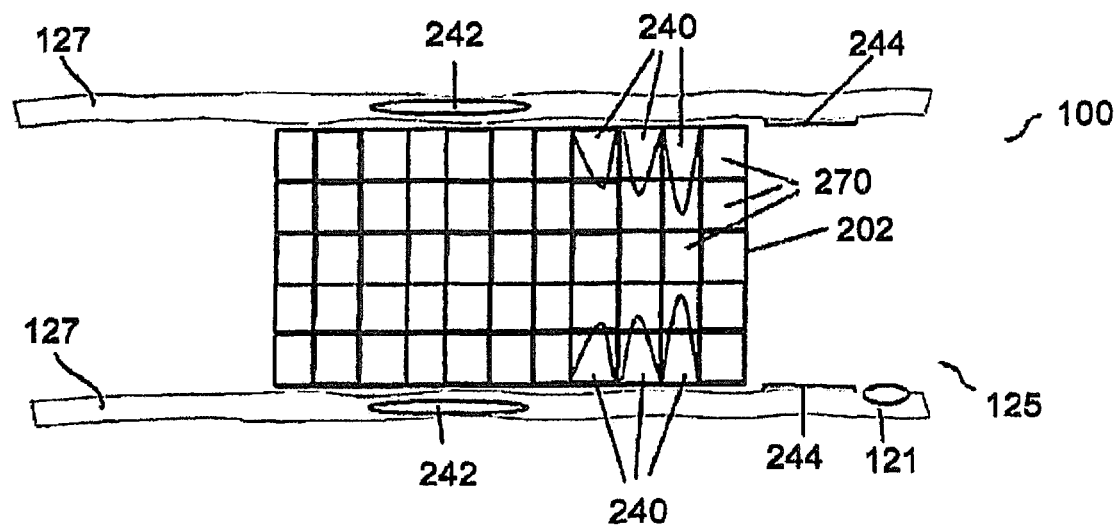

As seen in FIG. 24b, bare stent 202 has expanded radially in vessel lumen 125 to press against a stenotic area of tissue 240, thereby compressing and cracking stenotic area 240 radially outward. Following deployment of stent assembly 100, vessel lumen 125 expands, allowing better circulation through lumen 125.

Deployment of bare stent 202, however, causes damage to a basalamina intimal layer 127 resulting in the formation of scars 242, plaques 244 and new stenotic lesions 240 that protrude through apertures 270. Over the long-term, a large percentage of the recipients of bare stents 202 will develop significant stenotic lesions 240 that block vessel lumen 125, causing what is known as restenosis.

Figure 24C:
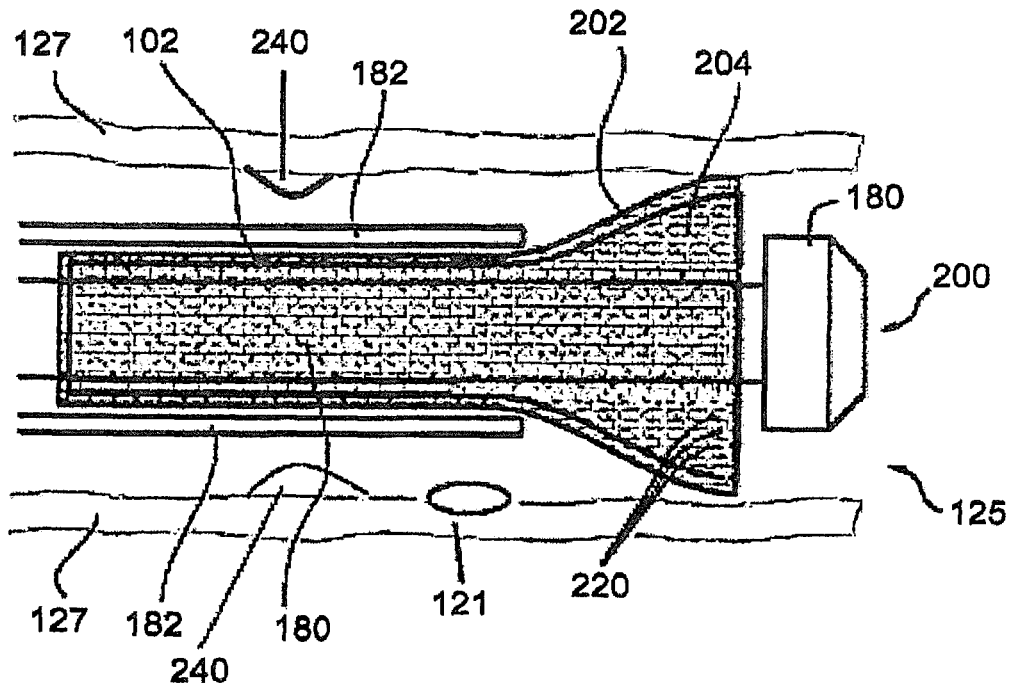

To prevent restenosis, (FIG. 24c), stent assemblies 200 have been developed comprising stents 202 with an internal or external jacket 204 having small apertures. Stent assembly 200 is shown in position around a spindle holder 180, emerging from a compression sheath 182, with stent 202 and stent jacket 204 in substantial tubular alignment. Typically, the jacket is formed of a polymer.

During expansion, jacket 204 prevents embolitic debris 121 generated from plaques along basalamina intimal layer 127 from entering vessel lumen 125.

Figure 24D:
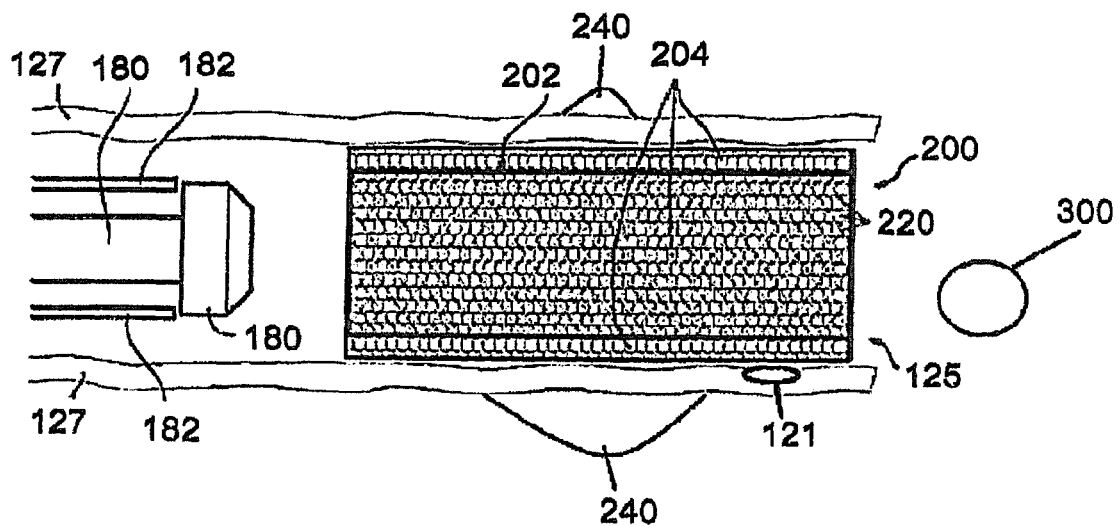

In FIG. 24d, stent assembly 200 is expanded radially in vessel lumen 125 so that jacket 204 presses stenotic tissue 240 radially outward. Following deployment of the stent assembly 200, stent jacket substantially prevents scars 242, plaques 244 and stenotic lesions 240 from protruding through apertures 270. In spite of substantially preventing restenosis, stent jacket 204 creates its own set of problems related to formation of an embolism 300.

Figure 25:
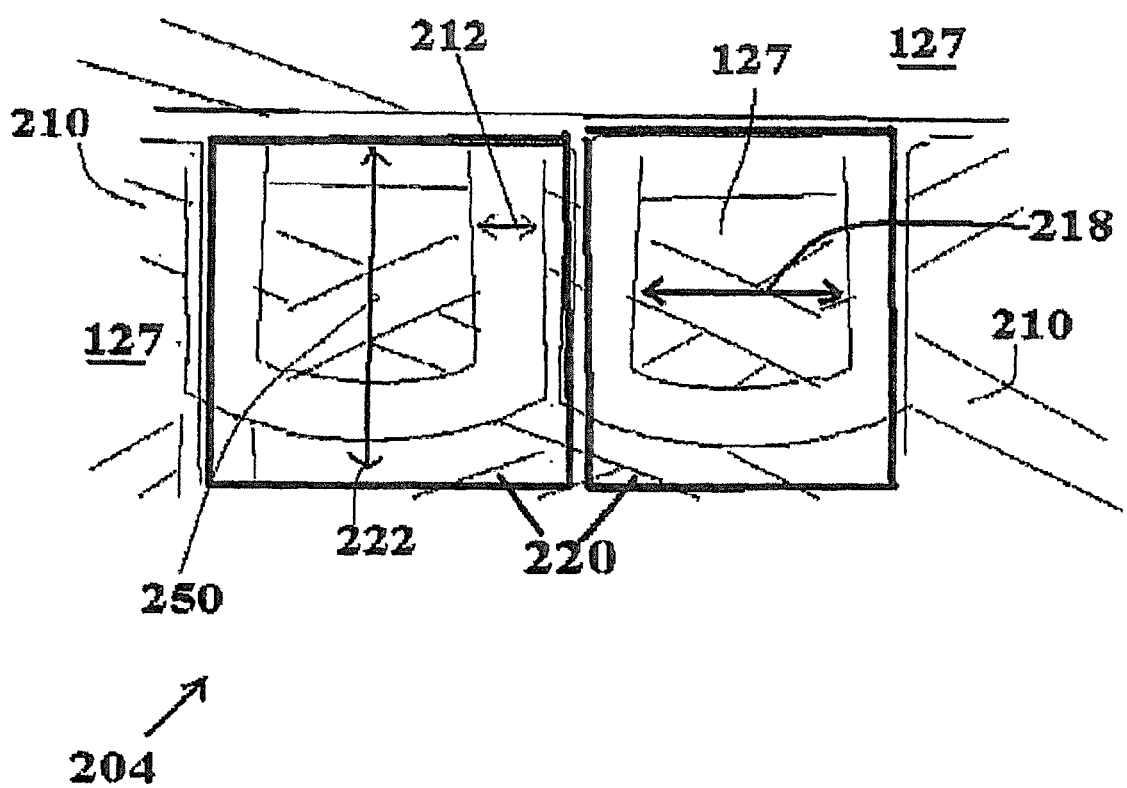
FIGS. 25-28 show in situ details of a typical stent jacket material in the art, in situ.

As noted above, to provide sufficient strength, stent jacket 204 may be made of interlacing knitted fibers, and/or fibers subject to chemical or heat treatments, all of which tend to increase the thickness of fibers 210 and bulk of jacket 204, seen in FIG. 25.

Within 48 hours following implantation of stent assembly 200 a layer of endothelial cells 220 coat stent jacket fibers 210 and basalamina intimal layer 127, as seen in FIG. 25.

Endothelial cells 220 have a diameter 222 of approximately 20 micrometers and maintain adherence to basalamina intimal layer 127 but generally do not substantially adhere to jacket fibers 210.

Fibers 210 in stent jacket typically have a thickness 212 of 20 micrometers so that endothelial cell 220 that straddles fiber 210, will have no attachment to basalamina intimal layer 127 and will easily dislodge from fiber 210.

Additionally, fibers 210 are typically spaced a distance 218 of less than 20 micrometers so that endothelial cell 220 that straddles between two fibers 210, will attach to the two adjacent fibers 210 and will have a marginal attachment to basalamina intimal layer 127 therebetween; again resulting in a cell 220 that is easily dislodged from fibers 210.

Figure 26:
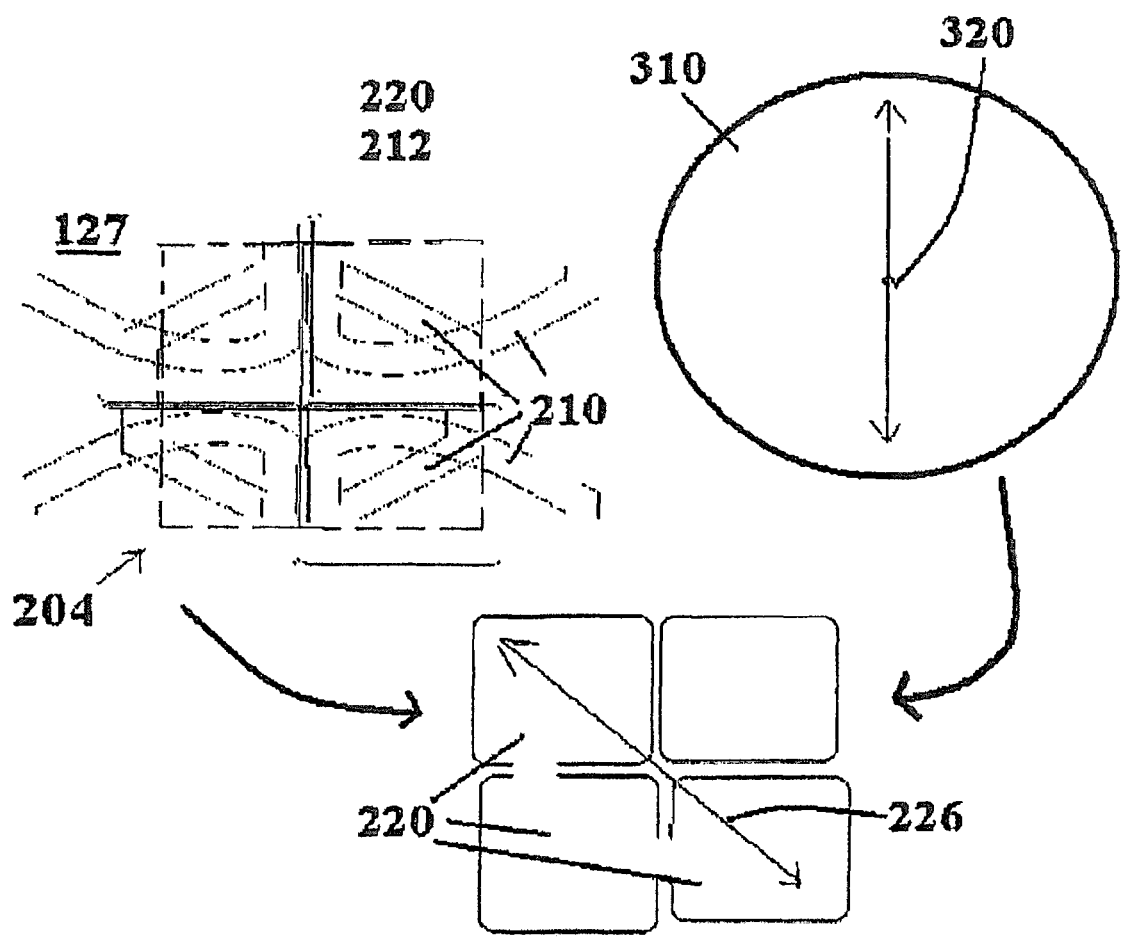

Single endothelial cells 220 that become detached from basalamina intimal layer 127, are not large enough to be recognized by platelets as foreign bodies around which to aggregate. However, as seen in FIG. 26, during natural movement of fibers 210, for example during regular pulsation of blood in circulation, a release of multiple interconnected cells 220 occurs.

In this case four endothelial cells 220, have broken loose from basalamina intimal layer 127, and are freely floating in vessel lumen. A platelet 310, having a diameter 320 of between four to ten times the diameter of endothelial cells 220, is attracted to masses that comprise at least two endothelia cells 220 and endothelial cells 220 provide an excellent attractive target for platelet 310.

Figure 27:
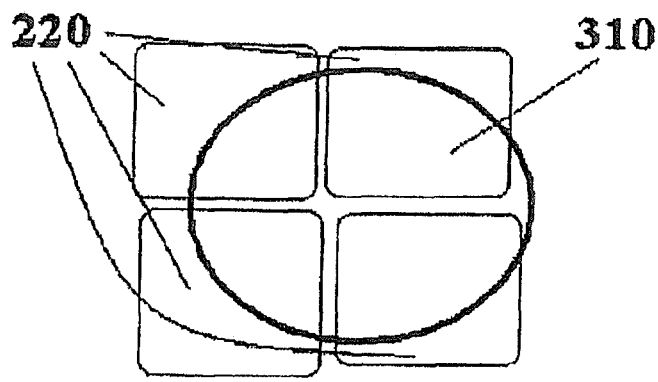
Figure 28:
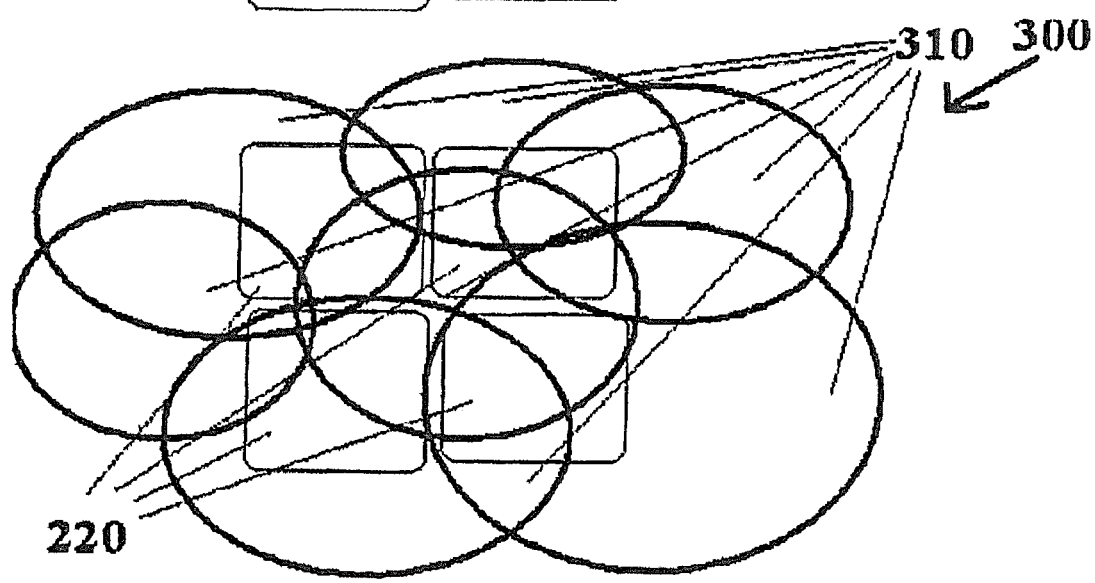

As seen in FIG. 27, a single platelet 310 has adhered to dislodged endothelial cells 220. As seen in FIG. 28, as a result of chemotaxis, additional platelets 310 have aggregated around endothelial cells 220 to form an embolism 300.

As noted above, embolism 300, comprising aggregated platelets 310, presents a health threat that can form at any time following implantation of stent jacket 204 causing an estimated 2% of all recipients of jacketed stents 204 to eventually develop necrosis of vital organs and/or die.

The tremendous and constant threat of emboli 300 from stent-and-jacket assembly 204 (FIG. 26) has resulted in lifetime administration of platelet aggregation reduction APIs. There are many life-threatening sequelae associated with Clopidogrel and there are many clinical trials being conducted on alternative platelet aggregation reducing APIs, including: Ticlopidine, Cangrelor, ARMYDA-2, and Prasugrel.

(Journal of Interventional Cardiology "TCT Annual Meeting: Antiplatelet Agents"; Volume 19 Page 193-April 2006.)

As noted above, lifetime administration of platelet aggregation reducing APIs, herein Clopidogrel, present problems to many sectors of the population.

For example, many jacketed stent recipients develop reactions that require cessation of Clopidogrel, such reactions include: ulcers, skin rashes, and syncope. With high bulk jacketed stents, Cessation of Clopidogrel puts the patient at risk for developing a life threatening embolus 300.

In addition to the hazards of embolus 300, there are patients who, not only must cease taking Clopidogrel and its accompanying risks, but may also develop conditions that are life threatening of themselves, including myelotoxicity, acquired hemophilia and TTP.

Additionally, there are the conditions that the patient may have that prevent the administration of Clopidogrel, including unresponsiveness to a platelet aggregate reducing API, an antithrombin deficiency, hereditary antithrombin deficiency (HD), immune depression, low CCR5 Delta 32 homozygous genotype (CCR5), acquired hemophilia, AIDS, HIV.

Moreover, there are risks presented to virtually every person receiving a jacketed stent. To prevent excessive bleeding in conjunction with virtually any surgery, Clopidogrel administration must be ceased for a significant period of time both pre-operatively and post-operatively. As a result, a patient who has received a stent and is a candidate for an elective surgery, for example prostate removal, is presented with a Hobson's choice of ceasing Clopidogrel administration and risking death from emboli, or taking Clopidogrel and risking embolism-free bleeding, hemorrhage and death.

Optimized Stent Assemblies

It has been found that specific configurations of the above-noted stents and jackets appear to provide advantages as is explained in the "Experimental Data" section. The specific features of these configurations will now be addressed.

Single fiber knits have been used in pantyhose since 1939, and comprise a plurality of interconnected loops known for strength, elastic qualities and thinness. Single fiber knit fabrics would be desirable as low bulk jackets 600 were it not from the problem that any loop along the edge of the nylon material can flip 180 degrees and form a run.

Figure 29:
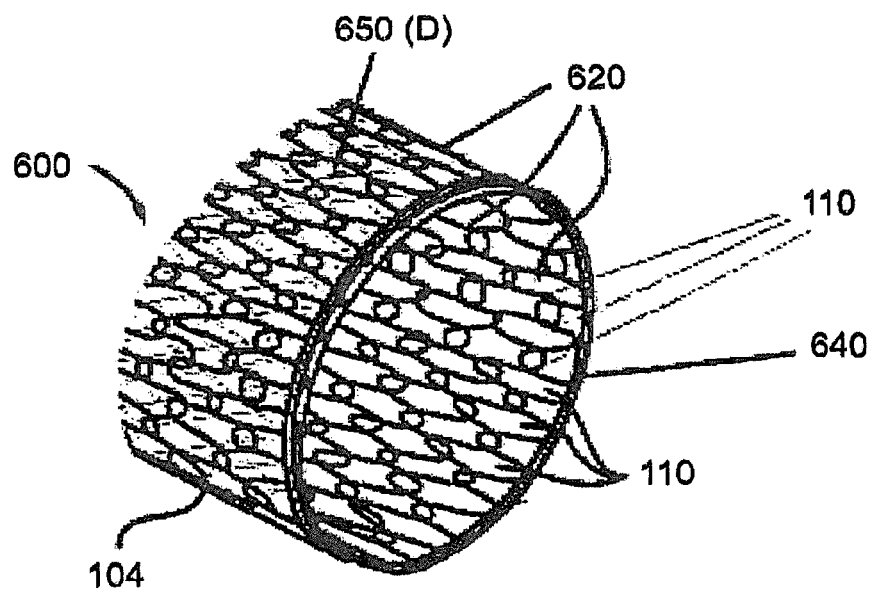
FIG. 29 shows a portion of the knitted stent jacket, according to embodiments of the invention.

FIG. 29 shows a knitted stent jacket 600 comprising knitted fibers 620 forming apertures 110. To prevent flipping in fibers 620, an elastomeric belt 640 has been passed through apertures 110 at the distal end of stent jacket 600. Optionally, an elastomeric belt 640 is similarly passed through loops at the proximal end of stent jacket 600 (not shown).

As used herein, any reference to a "knitted material" includes any material that is manufactured by a knitting process, including, inter alia: a material knitted from a single fiber, comprising either monofilament or multifilament fiber. The single fiber may comprise, inter alia, polyethylene, polyvinyl chloride, polyurethane, nylon, stainless steel, nitinol, or any other metal.

The biostable polymer comprises, inter alia, any one of a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, an aromatic polyester, a polyether (ether keto), a polysulfone, a silicone rubber, a thermoset, and a polyester (ester imide).

The natural polymer comprises, inter alia, a polyolefin, a polyurethane, a Mylar, a silicone, a polyester and a fluorinated polyolefin.

Figure 30:
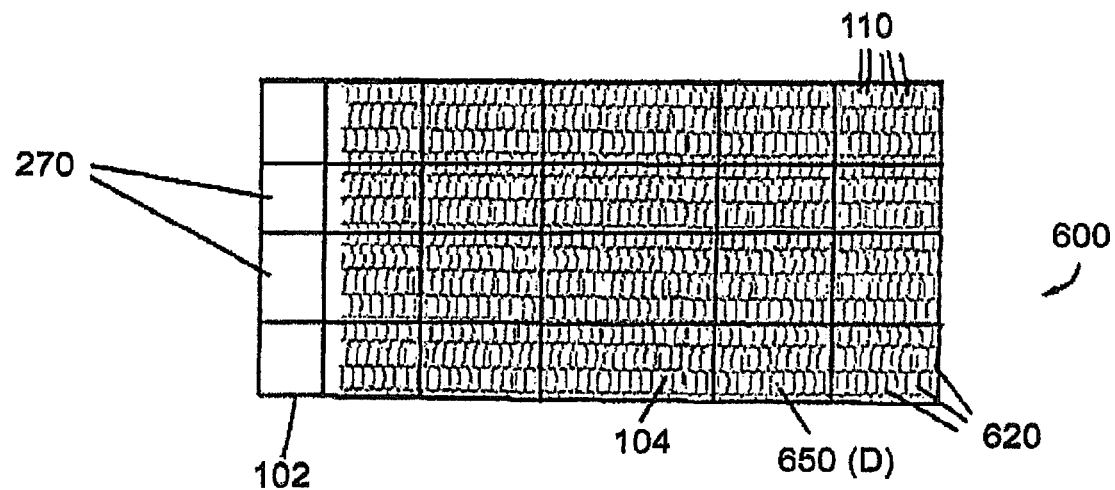
FIG. 30 shows a plan view of the knitted stent jacket of FIG. 29, according to embodiments of the invention.

As seen in FIG. 30, knitted stent jacket 104 includes apertures 110 that are maximized so that fibers 620 provide a small total coverage area in which stent jacket 104 covers a stent 102.

In accordance with some embodiments of the present invention, in an expanded state, the area of aperture 110 is between about 50,000 square micrometers and about 70,000 square micrometers. In alternative embodiments, aperture 110 has an area of between about 40,000 square micrometers and about 60,000 square micrometers. In other embodiments, aperture 110 has an area of between about 30,000 square micrometers and about 50,000 square micrometers.

With knitted stent jacket 104 having fibers 620 presenting a small total coverage, crimping stent 102 for insertion into compression sheath, 182 (FIG. 24*c*) for example, is relatively simple.

Additionally, a small total coverage allows crimped stent 102 to have a small profile, allowing easy maneuverability through lumen 125.

Moreover, with knitted stent jacket 104 having minimal thickness of fibers 620, stent jacket 104 substantially has a minimal influence on the mechanical properties of the stent during the delivery and expansion.

The location of jacket 104 externally on stent 102 protects basalamina intimal layer 127 from damage during expansion of stent 102. Additionally, the location of jacket 104 externally on stent 102 provides substantial protection against debris 121, seen in FIG. 24*d*, entering vessel lumen 125 during expansion of stent 102.

In accordance with some embodiments of the present invention, a proximal portion of jacket 104 is attached to a proximal aspect of stent 102 using a process selected from the group consisting of: sewing, adhesion, gluing, folding, suturing, riveting and welding. Such an attachment, for example, allows stent 102 to expand with a typically different coefficient of expansion than that of jacket 104 without causing damage to basalamina intimal layer 127.

As seen in a plan view of knitted stent jacket 600 in FIG. 30, knitted stent jacket 104 comprises a small coverage area noted in Appendix I, for example about 9%, or about 10%, or about 11%, or about 12% of the surface area of associated self-expanding stent 102. In general, the coverage area is less than 16%. Hence, in spite of crimping stent 102 prior to deployment, there is no need to fold knitted jacket 104 to fit into sheath 182 (FIG. 24*c*) prior to deployment; thereby reducing bulk and increasing maneuverability of stent assembly 200.

Chart 1 the attached Appendix provides support that the above-noted parameters of a knitted jacket on a self-expanding stent can be easily attained in the present invention using a fiber diameter of about 12.5 micrometers.

Figure 31:
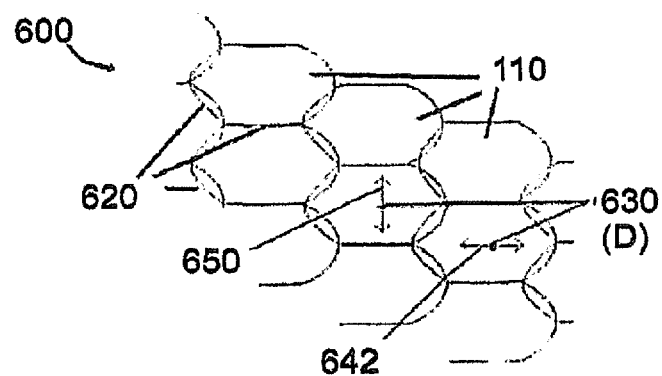
FIGS. 31-32 show details of the material including the knitted stent jacket of FIG. 29, according to embodiments of the invention.

FIG. 31 shows details of knitted jacket 600 in which apertures 110 have a longitudinal length 650 of greater than about 160 micrometers. In other embodiments, longitudinal length 650 is greater than about 180 micrometers. In other embodiments, longitudinal length 650 is greater than about 200 micrometers.

In accordance with some embodiments of the present invention, apertures 110 have a transverse length 642 of greater than about 250 micrometers. In other embodiments, transverse length 642 is greater than about 240 micrometers. In other embodiments, transverse length 642 is greater than about 230 micrometers.

It will be appreciated that the shorter one of the longitudinal length 650 and the transverse length 642 defines the minimum center dimension 630 (D) which must be greater than about 230 micrometers, and preferably, greater than 240 micrometers, and still more preferably, greater than 250 micrometers.

Figure 32:
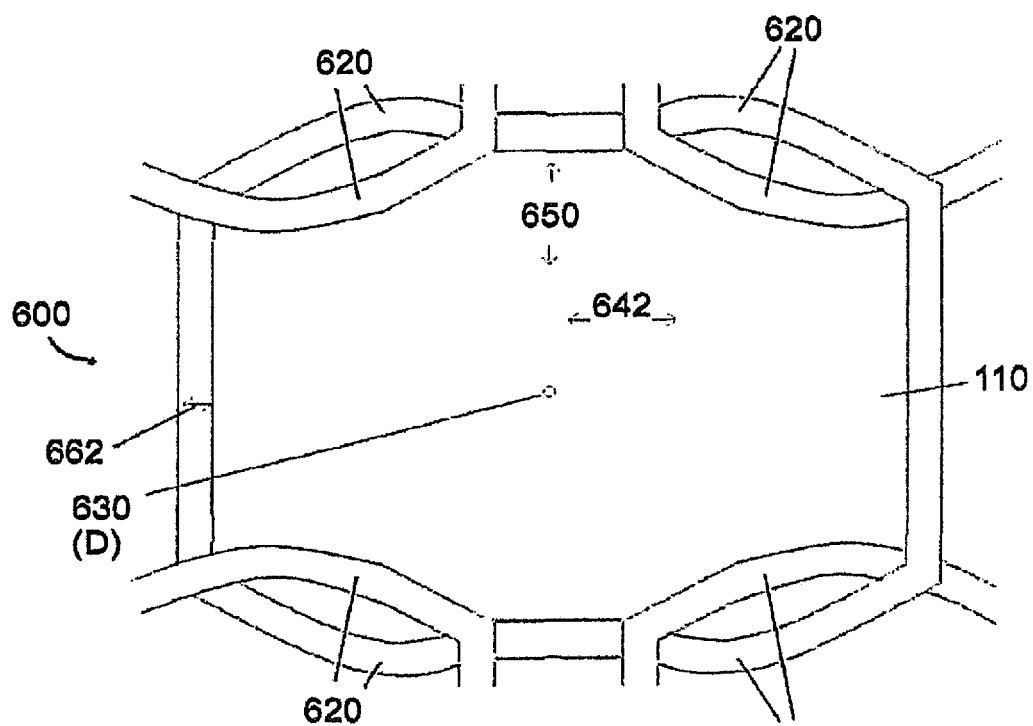

FIG. 32 shows that fibers 620 have a diameter 662, optionally in a range of between about 7 micrometers and about 18 micrometers. In other embodiments, diameter 662 is in a range of between about 10 micrometers and about 15 micrometers. In still other embodiments, diameter 662 is in a range of between about 11 micrometers and about 14 micrometers. In still other embodiments, diameter 662 is in a range of between about 12 micrometers and about 13 micrometers. In still other embodiments, diameter 662 is in a range of between about 12.25 micrometers and about 12.75 micrometers. In still other embodiments, diameter 662 of about 12.5 micrometers.

Figure 33:
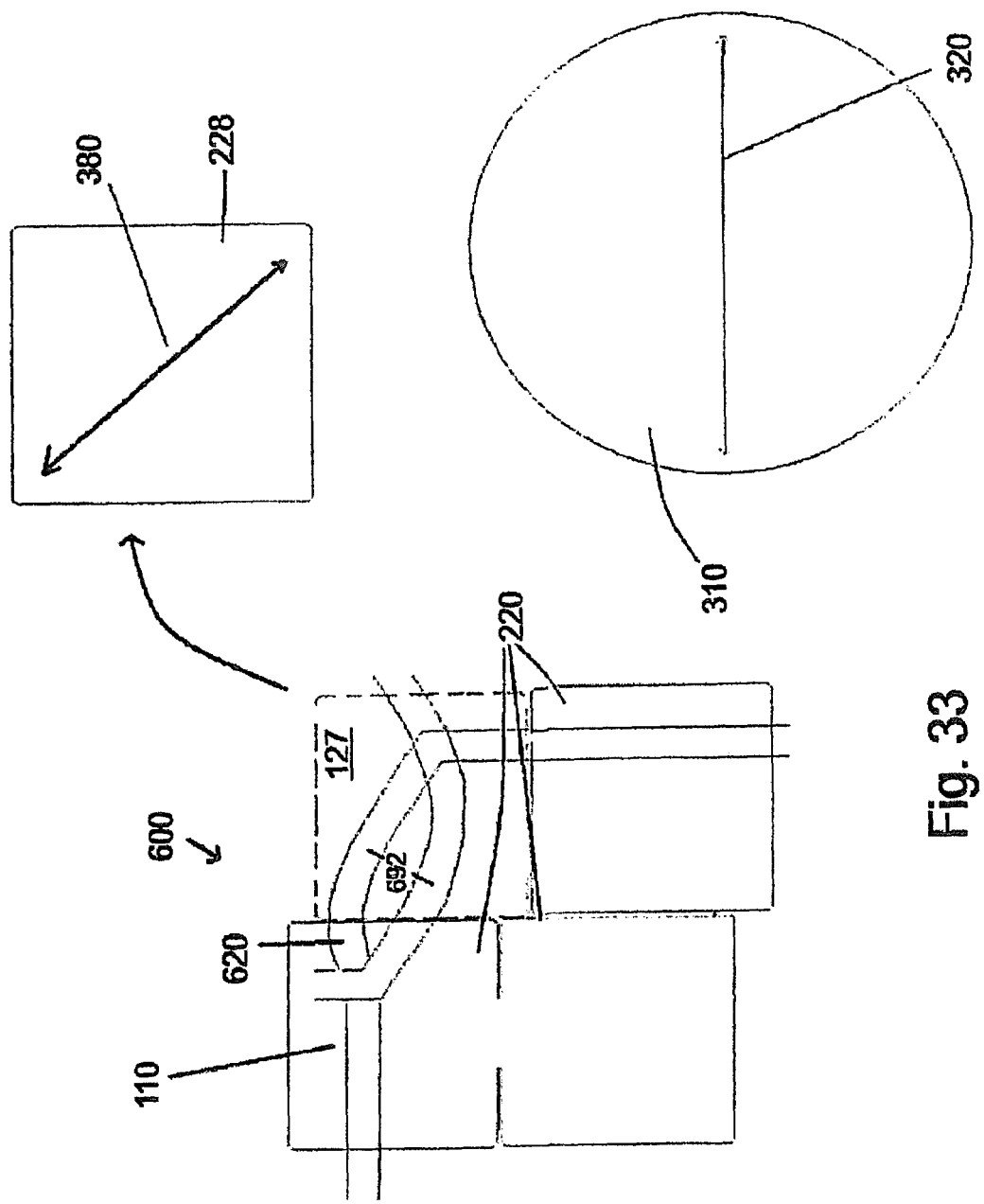
FIG. 33 shows in situ details of the material shown in FIGS. 8-9, according to embodiments of the invention.

Substantially inherent advantages of the measurements of knitted jacket 600 become readily apparent in FIG. 33 in which endothelial cells 220 are well adhered and stable against basalamina intimal layer 127 due to the thinness of fibers 620.

As a result of such spacing, a typical endothelial cell 220 will have substantial contact with basalamina intimal layer 127 as endothelial cell 220 is prevented from adhering to more than one column of fibers 620 due to the distance therebetween.

A group of three endothelial cells 220 is seen adhering to a portion of knitted stent jacket 600. Endothelial cells 220 have an amoeba-like movement so that at a fiber junction 692, cell 220 will typically touch down on junction 692 and move until a substantial portion of cell 220 is in substantial contact with basalamina intimal layer 127. In rare cases where a cell 228 fails to properly anchor into basalamina intimal layer 127, that specific single cell 228, alone, may have a tendency to dislodge due to movement of fibers 620 during normal pulsation in the blood circulation cycle. Due to the stability of adjacent cells 220 resulting from substantial contact with basalamina intimal layer 127, multiple cells 220 will not dislodge together with single cell 228.

As shown, single endothelial cell 228 has separated from basalamina intimal layer 127. However, single cell 228 does not have the necessary mass to be recognized by platelet 310 as a body worthy of adherence. As a result, there is no formation of the above-noted life-threatening embolism 300 associated with aggregation of platelets 310.

Typically, to ensure stability of endothelial cells 220, a patient receiving stent jacket 100 will be given a platelet aggregation reducing API, for example Clopidogrel, for no more than six months, and possibly less. For example, the patient may receive Clopidogrel for no more than for five months, no more than for four months, no more than for three months, no more than for two months, or no more than for one month.

At times, the patient receiving stent jacket 100 will not be given a platelet aggregation reducing API, the unique property of the fiber diameter, as illustrated in FIG. 32, and the advantage of the aperture minimum center dimension D, alone or in combination, relieving the need for the platelet aggregation reducing API, altogether. Thus, if the patient is scheduled to undergo elective surgery during the six-month administration, Clopidogrel may be discontinued without substantial fear of platelet aggregation.

Further, if, during a six-month administration period, the recipient of stent jacket 600 has any reaction, including ulcers, skin rashes, syncope, myelotoxicity, and TTP, Clopidogrel may be immediately ceased without substantial fear of embolism generation.

Further, Clopidogrel administration may be ceased or not initiated in the face of patient unresponsiveness to Clopidogrel, an antithrombin deficiency, HD, immune depression, low CCR5, acquired hemophilia, AIDS, and HIV.

Experimental Data

Reference is now made to the chart below showing experimental data, which together with the above description, illustrate the invention in a non-limiting fashion.

Optimization of jacket stent fiber thickness and aperture square area reduces the need for an anti-coagulation agent, for example Clopidogrel.

Maintaining small total coverage areas provides several additional advantages:

1. crimping the stent for insertion is relatively simple;
2. profile of the crimped stent is small;
3. stent jacket substantially has a minimal influence on the mechanical to properties of the stent during the delivery and expansion; and
4. jacket does not require folding during crimping when the coverage area of the stent is about 9%, or about 10%, or about 11%, or about 12% in self-expanding stent. In general the coverage area is less than 16%.

The chart below provides support that the above-noted parameters of jacket coverage on a stent can be easily attained in the present invention using a fiber diameter of about 12.5 micrometers.

TABLE-US-00002

| Stent Size [mm] | Fiber size [μ] | Head Needle No. | Aperture No. | Apertures Size Transverse [μ] | Longitudinal [μ] | Covered area [%] |
|---|---|---|---|---|---|---|
| 2.5 | 12.5 | 22 | 44 | 166 | 291 | 11% |
| 2.75 | 12.5 | 22 | 44 | 184 | 291 | 10% |
| 3 | 12.5 | 22 | 44 | 202 | 291 | 10% |
| 3.5 | 12.5 | 22 | 44 | 237 | 291 | 9% |
| 4 | 12.5 | 35 | 70 | 167 | 291 | 11% |
| 4.5 | 12.5 | 35 | 70 | 189 | 291 | 10% |
| 5 | 12.5 | 35 | 70 | 212 | 291 | 9& |
| 5.5 | 12.5 | 35 | 70 | 234 | 291 | 9% |

It is understood that the phraseology and terminology employed herein is for descriptive purpose and should not be regarded as limiting.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

As used herein, "a" or "an" mean "at least one" or "one or more". The use of the phrase "one or more" herein does not alter this intended meaning of "a" or "an".

It is expected that during the life of this patent many relevant stent jacket materials will be developed and the scope of the term stent jacket is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those of ordinary skill in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An intravascular device configured to treat an aneurysm, which comprises:
   a support structure configured to be positioned in a body lumen and defining a central fluid passage that extends axially along the support structure, wherein the support structure comprises a plurality of metal struts distributed along the support structure from a first outermost strut on a proximal end of the support structure to a second outermost strut on a distal end of the support structure; and
   a knitted mesh cover disposed over an exterior of the support structure, wherein the cover extends across a radial arc and along an entire axial length of the support structure sufficient to exceed an opening of an aneurysm to be treated and the cover comprises a polymer fiber having a diameter of at least 40 nanometers to 30 microns arranged to provide apertures through the cover which apertures are at least 20 microns to 300 microns and the knitted mesh cover and the support structure are arranged to minimize or prevent an aneurysm-filling material from exiting the aneurysm therethrough into the central fluid passage,
   wherein loops of the knitted mesh cover are slidably attached to the first and second outermost struts of the support structure such that in expanding from a pre-expanded state to a deployed state, the cover is allowed to expand a different amount than the support structure, by having the loops of the cover attached to the first and second outermost struts slide along the first and second outermost struts.

2. The intravascular device of claim 1, wherein the knitted mesh cover is adapted to prevent the aneurysm-filling material from exiting the aneurysm.

3. The intravascular device of claim 2, wherein a second knitted mesh cover is disposed out of phase over the knitted mesh cover to further minimize or prevent the aneurysm-filling material from protruding from the aneurysm.

4. The intravascular device of claim 1, wherein the apertures have a diameter of more than 100 microns to below 300 microns.

5. The intravascular device of claim 1, wherein the apertures have a minimum center dimension of approximately 150 microns by 200 microns.

6. The intravascular device of claim 1, wherein the nominal aperture size is no greater than 200 microns.

7. The intravascular device of claim 1, wherein the aperture diameter is smaller than 100 microns.

8. The intravascular device of claim 1, wherein the nominal aperture size is no greater than 50 microns.

9. The intravascular device of claim 1, wherein the device further minimizes or prevents embolism-causing debris from entering the central fluid passage.

10. A method of treating an aneurysm which comprises positioning the intravascular device of claim 1 adjacent to an aneurysm in a body lumen of a patient in need of aneurysm therapy.

11. The method of claim 10, wherein the aneurysm is a cerebral aneurysm.

12. The intravascular device of claim 1, wherein the first and second outermost struts include most outlying positions and innermost positions along the support structure, and wherein in the pre-expanded state, one or more loops of the knitted mesh cover are attached to most-outlying positions of the first outermost strut.

13. The intravascular device of claim 12, wherein in the pre-expanded state, one or more loops of the knitted mesh cover are attached to most-outlying positions of the second outermost strut.

14. The intravascular device of claim 12, wherein in expanding to the deployed state, the one or more loops of the knitted mesh cover slide from the most outlying positions of the first outermost strut to the innermost position of the first outermost strut.

15. The intravascular device of claim 1, wherein in expanding to the deployed state, the one or more loops of the knitted mesh cover slide a distance of between 1-6 millimeters.

16. The intravascular device of claim 1, wherein the loops of the knitted mesh cover are slidably attached to the first and second outermost struts by stitches.

17. The intravascular device of claim 1, wherein the stitches are biodegradable.

18. The intravascular device of claim 1, wherein the knitted mesh is attached only to the first and second outermost struts.

19. An intravascular device configured to treat an aneurysm, which comprises:
   a support structure configured to be positioned in a body lumen and defining a central fluid passage that extends axially along the support structure, wherein the support structure comprises a plurality of metal struts distributed along the support structure from a first outermost strut on a proximal end of the support structure to a second outermost strut on a distal end of the support structure; and
   a knitted mesh cover disposed over an exterior of the support structure, wherein the cover extends across a radial arc and along an axial length of the support structure sufficient to exceed an opening of an aneurysm to be treated and the cover comprises a polymer fiber having a diameter of at least 40 nanometers to 30 microns arranged to provide apertures through the knitted mesh cover, wherein the knitted mesh cover has smaller apertures on an aneurysm-facing side of the support structure to restrict blood flow therethrough, relative to larger apertures on an opposite side of the support structure to permit blood flow to a branching vessel,
   wherein loops of the knitted mesh cover are slidably attached to the first and second outermost struts of the support structure such that in expanding from a pre-expanded state to a deployed state, the cover is allowed to expand a different amount than the support structure, by having the loops of the cover attached to the first and second outermost struts slide along the first and second outermost struts.

20. The intravascular device of claim 19, wherein the device promotes clot formation within the aneurysm.

21. The intravascular device of claim 19, wherein the knitted mesh cover does not extend across the entire support structure to avoid restricting blood flow to a branching vessel.

22. The intravascular device of claim 19, wherein the knitted mesh cover prevents embolism-causing debris from entering the lumen from an aneurysm.

* * * * *